United States Patent [19]
Haynes et al.

[11] Patent Number: 5,998,172
[45] Date of Patent: Dec. 7, 1999

[54] ANTI-CD6 LIGAND ANTIBODIES

[75] Inventors: Barton F. Haynes, Durham, N.C.;
Alejandro Aruffo, Edmonds, Wash.;
Dhavalkumar D. Patel, Durham, N.C.;
Michael A. Bowen, Seattle, Wash.;
Hans Marquardt, Mercer Island, Wash.; Anthony W. Siadak, Seattle, Wash.

[73] Assignees: Duke University, Durham, N.C.;
Bristol-Myers Squibb Company, New York, N.Y.

[21] Appl. No.: 08/684,594

[22] Filed: Jul. 18, 1996

Related U.S. Application Data

[63] Continuation-in-part of application No. 08/432,016, May 1, 1995, which is a continuation-in-part of application No. 08/333,350, Nov. 2, 1994, Pat. No. 5,723,437, which is a continuation-in-part of application No. 08/143,903, Nov. 2, 1993, abandoned.

[51] Int. Cl.⁶ .............................. C12N 5/12; C07K 16/28
[52] U.S. Cl. .................................... 435/70.21; 530/388.1; 530/388.15; 530/388.22
[58] Field of Search ............................. 530/387.1, 388.1, 530/388.15, 388.22; 435/70.21

[56] References Cited

PUBLICATIONS

Hillier et al, Accession No. R14919, Wash U–Merck EST Project, Apr. 1995.

Hillier et al, Accession No. T68513, Wash U–Merck EST Project, Feb. 1995.

Pourquie et al, "BEN, a surface glycoprotein of the immunoglobulin superfamily, is expressed in a variety of developing systems", Proc. Natl. Acad. Sci. USA 89:5261–5263 (1992).

Sambrook et al, Molecular Cloning, A Lab. Manual, 2nd Edition, 16.2–16.30 and 17.2–17.28 (1989) Cold Spring Harbor Lab. Press, Cold Spring Harbor.

Swack et al, "Structural Characterization of CD6: Properties of Two Distinct Epitopes Involved in T Cell Activation", Molecular Immunology 26(11):1037–1049 (1989).

Patel et al, "Identification and Characterization of a 100–kD Ligand for CD6 on Human Thymic Epithelial Cells", J. Exp. Med. 181:1563–1568 (1995).

Bowen et al, "Cloning, Mapping, and Characterization of Activated Leukocyte–Cell Adhesion Molecule (ALCAM), a CD6 Ligand", J. Exp. Med. 181:2213–2220 (1995).

Wee et al, "Characterization of a CD6 Ligand(s) Expressed on Human–and Murine–Derived Cell Lines and Murine Lymphoid Tissues", Cellular Immunology 158:353–364 (1994).

Sims et al, "cDNA Expression Cloning of the IL–1 Receptor, a Member of the Immunoglobulin Superfamily", Science 241:585–589 (1988).

Aruffo et al, "The Lymphocyte Glycoprotein CD6 Contains a Repeated Domain Structure Characteristic of a New Family of Cell Surface and Secreted Proteins", J. Exp. Med. 174:949–952 (1991).

Kamoun et al, "A Novel Human T Cell Antigen Preferentially Expressed on Mature T Cells and Shared By Both Well and Poorly Differentiated B Cell Leukemias and Lymphomas", The Journal of Immunology 127(3):987–1991 (1981).

Gangemi et al, "Anti–T12, An Anti–CD6 Monoclonal Antibody, Can Activate Human T Lymphocytes", The Journal of Immunology 143:2439–2447 (1989).

Morimoto et al, "2H1—A Novel Antigen Involved in T Lymphocyte Triggering", The Journal of Immunology, 140:2165–2170 (1988).

Wee et al, "Tyrosine Phosphorylation of CD6 by Stimulation of CD3: Augmentation by the CD4 and CD2 Coreceptors", J. Exp. Med. 177:219–223 (1993).

Soiffer et al, Prevention of Graft–Versus–Host Disease by Selective Depletion of CD6–Positive T Lymphocytes from Donor Bone Marrow:, Journal of Clinical Oncology 19(7):1191–1200 (1992).

Vollger et al, "Thymocyte Binding to Human Thymic Epithelial Cells is Inhibited by Monoclonal Antibodies to CD–2 and LFA–3 Antigens", The Journal of Immunology 138:358–363 (1987).

Swack et al, "Biosynthesis and Post–translational Modification of CD6, a T Cell Signal–transducing Molecule", The Journal of Biological Chemistry 266(11):7137–7143 (1991).

Pawelec and Buhring, "Monoclonal Antibodies to CD6 Preferentially Stimulate T–Cell Clones with γ/δ Rather Than α/β Antigen Receptors", Human Immunology 31:165–169 (1991).

Mayer et al, "Expression of the CD6 T lymphocyte differentiation antigen in normal human brain", Journal of Neuroimmunology 29:193–202 (1990).

Aruffo et al, "Granule membrane protein 140 (GMP140) binds to carcinomas and carcinoma–derived cell lines", Proc. Natl. Acad. Sci. USA 89:2292–2296 (1992).

Pesandro et al, Antibody–Induced Antigenic Modulation is Antigen Dependent: Characterization of 22 Proteins on a Malignant Human B Cell, The Journal of Immunology 137(11):3689–3695 (1986).

Patel et al, "Human Thymic Epithelial Cells Express a Ligand for CD6 which Mediates Binding to Mature Thymocytes", Clinical Research 41(2):220A (1993).

Burns et al., Neuron, 7, 209–220, Aug. 1991.

Tanaka et al., Neuron 7, 535–545, Oct. 1991.

*Primary Examiner*—Sally Teng
*Attorney, Agent, or Firm*—Nixon & Vanderhye P.C.

[57] ABSTRACT

The present invention relates, in general, to CD6 and, in particular, to a CD6 ligand present on the surface of thymic epithelial cells, monocytes, activated T cells and a variety of other cell types. The invention further relates to methods of inhibiting the interaction of CD6 and the CD6 ligand, and to methods of screening compounds for their ability to inhibit that interaction. The invention also relates to antibodies, and binding fragments thereof, specific for CD6 ligand.

3 Claims, 31 Drawing Sheets

CHARACTERIZATION OF THE CD6 LIGAND(S)

FIG. 26A

```
            1                                                                                                  *       100
hALCAM      YGDTIIIPCR LDV..PQNLM FGKWKYEKPD GSPVFIAFRS STKKSVQYDD VPEYKDRLNL SE.NYTLSIS NARISDEKRF VCMLVTEDNV FEAPTI.VKV
cBEN        YGDTITMPCR LEV..PDGLM FGKWKYEMPN GSPVFIAFRS STKKNVQYDD VPDYKDRLSL SE.NYTLSIK NARISDEKRF VCMLVTEDDV SEEPTV.VKV
fNeurolin   YGETIVVPCN DGTKKPDGLI FTKWKYVKDD GSPGDLLVKQ AQKDEATVSA TDGYKSRVSI AA.NSSLLIA RGSLADQRVF TCMVVSFTNL EEYSVE.VKV
hRAGE       IGEPLVLKCK GAPKKPPQRL EWKLNTGRTE AWKVLSP... ........QG GGPWDSVARV LP.NGSLFLP AVGIQDEGIF RCRAMNRNGK ETKSNYRVRV
hMuc18      VGSTALLKCG LSQSQGNLSH VDWFSVHKEK RTSSSVCARA RAR...... AN LGSTSKRLSL QDRGATLALT QVTPQDERIF LCQGKRLGPR STASSSASTK
Consensus   YG-TI--PC- L-----P--L- F-KWKY-K-- GSPV-----R- ---------- ---YK-RLSL ---N-TL-I- ---I-DE--F --CM-V---- -E-S---VKV 101                                                                                                *       200
hALCAM      FKQPSKPEIV SKALFLETEQ LKKLGDCISE DSYPDGNITW YRNGKVLHPL EGAVVIIFKK EMDPVTQLYT MTSTLEYKTT K.ADIQMPFT CSVTYYGP..
cBEN        FKQPSQPEIL HQADFLETEK LKMLGECVVR DSYPEGNVTW YKNGRVLQPV EEVVVINLRK VENRSTGLFT MTSSLQYMPT K.EDANAKFT CIVTYHGP..
fNeurolin   HKKPSAPVIK NNAKELENGK LTQLGECVVE NANPPADLIW KKNNQTLVDD GKTIIITSTI TKDKITGLSS TSSRLQYTAR K.EDVESQFT CTAKHVMG..
hRAGE       YQIPGKPEIV DSASELTAGV PNKVGTCVSE GSYPAGTLSW HLDGKPLVPN EKGVSVKEQT RRHPETGLFT LQSELMVTPA RGGDPRPTFS CSFSPGLPRH
hMuc18      LRMPNI.QVN PLGIPVNSKE PEEVATCVGR NGYPIPQVIW YKNGRPLKEE KNRVHIQSSQ TVE.SSGLYT LQSILKAQLV K.EDKDAQFY CELNYRLP..
Consensus   -K-PS-PEI- --A--LE--- L--LG-CV-E -SYP-G---W YKNG------ E--V-I---- ----TGL-T- ---S-L-Y-- -K-ED----FT C---Y--P--

201                                                                                     *                 300
hALCAM      SGQKTIHSEQ AVFDIYYPTE QVTIQVLPPK SAIKEGDNIT LKCLGNGNPP PE.....EFL FYLPGQPEGI VRRNATGDYK C....SLIDK.
cBEN        SGQKTIQSEP VVFDVHYPTE KVTIRVLSQS STIKEGDNVT LKCSGNGNPP PQ.....EFL FYIPGETEGI VRRNATGEYK C....SLID..
fNeurolin   PDQV...SEP ESFPIHYPTE KVSLQVVSQ. SPIREGEDVT LKCQADGNPP PT.....SFN FNIKGKKVTV TDKDVYTLTG VTRADSGIYK C....SLLDN.
hRAGE       RALRTAPIQP RVWEP.VPLE EVQLVEPEG GAVAPGTVT LTCEVPAQPS PQ......IH WMKDGVPLPL PPSPVLILPE IGPQDQGTYS C....VATHSS
hMuc18      SGNHMKESRE VTVPVFYPTE KVWLEVEP.V GMLKEGDRVE IRCLADGNPP PHFSISKQNP STREAEEETT NDNGVLVLEP ARKEHSGRYE CQAWNLDTMI
Consensus   SGQ-T---SEP -VFD--YPTE KV-L-V-P-- S-IKEGD-VT LKC---GNPP P-------F- F---G--E-- ---S-VY-LT- VRR---G-YK C----SL-D--

301                                                                                     *                 400
hALCAM      KSMIASTAIT VHYLDLSLNP SGEVTRQIGD ALPVSCTISA SRNATVVWMK DNIRLRSSPS ...FSSLHY QDAGNYVCET ALQEVEGLKK RESLTLIVEG
cBEN        KSMMDTTTIT VHYLDLQLTP SGEVTKQIGE ALPVSCTISS SRNATVFWIK DNTRMKTSPS ...FSSLQY QDAGNYICET THKEVEGLKK RKTLKLIVEG
fNeurolin   DVMESTQFVT VSFLDVSLTP TGKVLKNVGE NLIVSLDKNA SSEAKVTWTK DNRKLDKLPD ...FSKLTY SDAGLYVCDV S...IEGIKR SLSFELTVEG
hRAGE       SLLSEPQELL VNYVSDVRVS PAAPERQEGS SLTLTCEAES SQDLEFQWLR EETDQVLERG PVLQLHDLKR EAGGYRCVA SVPSIPGLNR TQLVKLAIFG
hMuc18      --M-----T V-YLD--L-P -G-V----Q- -L-VSC---- -L-VSC---- S-A-V-W-K DN------P- ----FS-L-Y -DAG-Y-C-- ------EGLK- ------L-VEG 401                                                                                                       500
hALCAM      KPQI..KMTK KTDPSGLSKT IICHVEGFPK PAIQWTITGS GSVINQTEES PYINGRYYSK IIISPEENVT LTCTAENQLE RTVNSLNVSA ISIPEHDEAD
cBEN        KPQI..KMTK KTNTNKMSKT IVCHVEGFPK PAVQWTVTGS GSLINKTEET KYVNGKFSSK IIIAPEENVT LTCIAENELE RTVTSLNVSA ISIPEYDEPE
fNeurolin   IPKIT.SLTK HRSSDGKHKV LTCEAEGSPK PDVQWSVNGT .....NDEV SYNNGKATYK LTVVPSKNLT VSCLVTNKLG EDTK..EISV FSQKNEDGTE
hRAGE       PPWMAFKERK VWVKENMVLN LSCEASGHPR PTISWNVNGT ASEQDQDPQR VLSTLNV... -Y-NG----K LVTPELLETG VECTASNDLG KNTSILFLEL VNLTTLTPDS
Consensus   -P-I--K-TK ------------K- --C--EG-PK P--QW-V-G- -S-------- -Y-NG----K ----P-N-T --C-A-N-L- ------L-S- ------D---
```

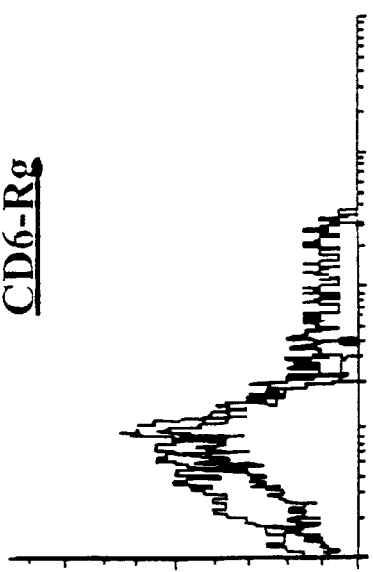
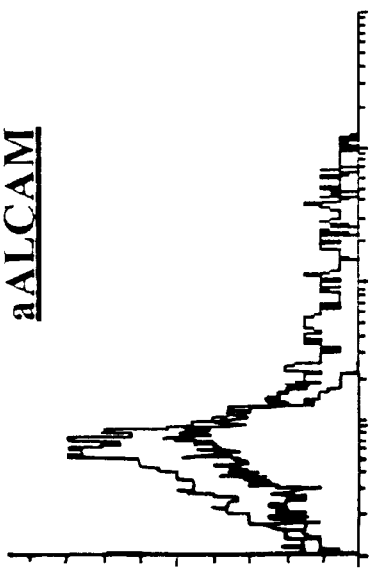
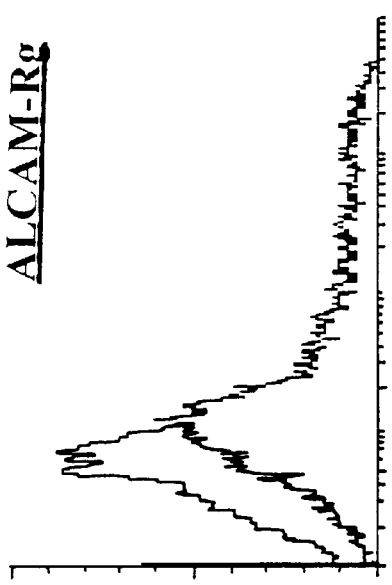
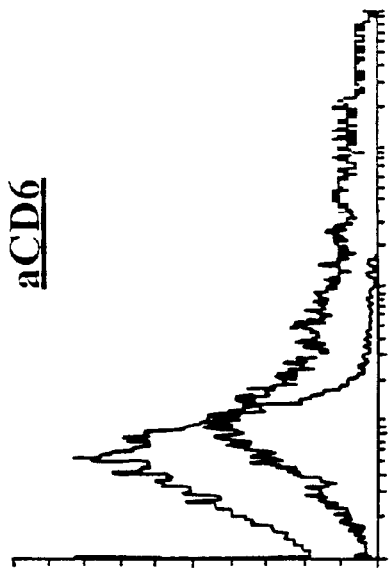
FIG. 28A
FIG. 28B

Fig. 29A

```
1123  TGCACAATATCTGCTAGCAGGAATGCAACTGTGGTATGGATGAAAGATAACATCAGGCTTCGATCTAGCCCGTCATTTTCTAGTCTTCATTATCAGGATGCT
 327    C   T   I   S   A   S   R  [N]  A   T   V   V   W   M   K   D   N   I   R   L   R   S   S   P   S   F   S   S   L   H   Y   Q   D   A
1225  GGAAACTATGTCTGCGAAACTGCAGCTTCTGCAGGAGGTTGAAGGACTAAAGAAAGAGAGTCATTGTGACTGTGAAGGCAAACCTCAAATAAAATGACA
 361    G   N   Y   V   C   E   T   A   L   Q   E   V   E   G   L   K   K   R   E   S   L   T   L   I   V   E   G   K   P   Q   I   K   M   T
1327  AAGAAAACTGATCCCAGTGGACTATCTAAAACAATAATCTGCCATGTGGAAGGTTTTCCAAAGCCAGCCATTCAaTGGACAATTACTGGCAGTGGAAGCGTC
 395    K   K   T   D   P   S   G   L   S   K   T   I   I   C   H   V   E   G   F   F   P   K   P   A   I   Q gRaW T   I   T   G   S   G   S   V
1429  ATAAACCAAACAGAGAGAACAGTAAACTCCTTGAATGTCTCTGCTATAAGTATTCCAGAACACGAGATAAGTGATGAAAACAGAGAAAAGGTGAAT
 429    I  [N]  Q   T   E   E   S   P   Y   I   N   G   R   Y   Y   S   K   I   I   I   S   P   E   E  [N]  V   T   L   T   C   T   A   E   N
1531  CAACTGGAGAGAACAGTAAACTCCTTGAATGTCTCTGCTATAAGTATTCCAGAACACGAGATAAGTGATGAAAACAGAGAAAAGGTGAAT
 463    Q   L   E   R   T   V   N   S   L  [N]  V   S   A   I   S   I   P   E   H   D   E   A   D   E   I   S   D   E   N   R   E   K   V   N
1633  GACCAGGCAAAACTAATTGTGGGAATCGTTGTTGGTCTTCTGCTCGCCCTTGTTGCTGCCGTGTCGTCTACTGGCTGTCATGGCTGTAAGAAGTCAAAGACTGCA
 497    D   Q   A   K   L   I   V   G   I   V   V   G   L   L   L   A   A   L   V   A   G   V   V   Y   W   L   Y   M   K   K   S   K   T   A
1735  TCAAAACATGTAAACAAGGACCTCGGTAATATGGAAGAAAACAAAAAGTTAGAAGAACAATCACAAAACTGAAGCTAAGACAAACTGTCCTAGTTGT
 531    S   K   H   V   N   K   D   L   G   N   M   E   E   N   N   K   K   L   E   E   N   N   H   K   T   E   A   *   556
1837  CCAGAGATAAAAATCATATAGACCAATTGAAGCATGAACGTGATTGTATTTAAGACATAAGACATTGACAGCAATTCATGGTTCAAGTATTAAGCA
1939  GTTCATTCTACCAAGCTGTCTCCAAGGTTTTCAGAGAATTATCTCAAGTAAATCTCGCACTGAGGATTTCTTTGGTTTGCCTTTTATGTTTATTTTTACGTAGTATT
2041  ATAGGTCATATGTGTGTTGGTTGTTCTTGTTCTGGGAGTTGCTGTTAATCTGATGTATAAGACACCTAAAACCCCAAAGTGGCAGCTTGTGAAGATTGGGACACTCATATTGCCCTAA
2143  TTTATACACTGTAAGCTTGCTATCAGCAATGCCCCCAAACTTTCTCATAAGCACCCTAAAACCCCAAAGTGGCAGCTTGTGAAGATTGGGACACTCATATTGCCCTAA
2245  TCTGATTCTGATTGTTTATCACAAGGGAGGGAGGCCGAGAGTCAGACTGCGAAGAGCCGACTCTTTGATATGCCACCAGCGAACTCTCAGA
2347  TTAAAACTGTGATTTTATCACAAGGGAGGGAGGCCGAGAGTCAGACTGCGAAGAGCCGACTCTTTGATATGCCACCAGCGAACTCTCAGA
2449  AATAAATCACAGATGCATATAGACACACATAAGTACTCCCAAACTGACAATTTACCTATTCTGAAAAGACATAAAACAGAATT  2539
```

*Fig. 29B*

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
       (A) LENGTH: 2539 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:1:

```
CGGGACGACG CCCCCTCCTG CGGCGTGGAC TCCGTCAGTG GCCCACCAAG AAGGAGGAGG      60

AATATGGAAT CCAAGGGGGC CAGTTCCTGC CGTCTGCTCT TCTGCCTCTT GATCTCCGCC     120

ACCGTCTTCA GGCCAGGCCT TGGATGGTAT ACTGTAAATT CAGCATATGG AGATACCATT     180

ATCATACCTT GCCGACTTGA CGTACCTCAG AATCTCATGT TTGGCAAATG GAAATATGAA     240

AAGCCCGATG GCTCCCCAGT ATTTATTGCC TTCAGATCCT CTACAAAGAA AGTGTGCAG      300

TACGACGATG TACCAGAATA CAAAGACAGA TTGAACCTCT CAGAAAACTA CACTTTGTCT     360

ATCAGTAATG CAAGGATCAG TGATGAAAAG AGATTTGTGT GCATGCTAGT AACTGAGGAC     420

AACGTGTTTG AGGCACCTAC AATAGTCAAG GTGTTCAAGC AACCATCTAA ACCTGAAATT     480

GTAAGCAAAG CACTGTTTCT CGAAACAGAG CAGCTAAAAA AGTTGGGTGA CTGCATTTCA     540

GAAGACAGTT ATCCAGATGG CAATATCACA TGGTACAGGA ATGAAAAAGT GCTACATCCC     600

CTTGAAGGAG CGGTGGTCAT AATTTTTAAA AAGGAAATGG ACCCAGTGAC TCAGCTCTAT     660

ACCATGACTT CCACCCTGGA GTACAAGACA ACCAAGGCTG ACATACAAAT GCCATTCACC     720

TGCTCGGTGA CATATTATGG ACCATCTGGC CAGAAAACAA TTCATTCTGA ACAGGCAGTA     780

TTTGATATTT ACTATCCTAC AGAGCAGGTG ACAATACAAG TGCTGCCACC AAAAARTGCC     840

ATCAAAGAAG GGGATAACAT CACTCTTAAA TGCTTAGGGA ATGGCAACCC TCCCCCAGAG     900

GAATTTTTGT TTTACTTACC AGGACAGCCC AAGGAATAA  GAAGCTCAAA TACTTACACA     960

CTGAYGGATG TGAGGCGCAA TGCAACAGGA GACTACAAGT GTTCCCTGAT AGACAAAAAA    1020

AGCATGATTG CTTCAACAGC CATCACAGTT CACTATTTGG ATTTGTCCTT AAACCCAAGT    1080

GGAGAAGTGA CTAGACAGAT TGGTGATGCC CTACCCGTGT CATGCACAAT ATCTGCTAGC    1140

AGGAATGCAA CTGTGGTATG GATGAAAGAT AACATCAGGC TTCGATCTAG CCCGTCATTT    1200

TCTAGTCTTC ATTATCAGGA TGCTGGAAAC TATGTCTGCG AAACTGCTCT GCAGGAGGTT    1260

GAAGGACTAA AGAAAAGAGA GTCATTGACT CTCATTGTAG AAGGCAAACC TCAAATAAAA    1320

ATGACAAAGA AAACTGATCC CAGTGGACTA TCTAAAACAA TAATCTGCCA TGTGGAAGGT    1380

TTTCCAAAGC CAGCCATTCA RTGGACAATT ACTGGCAGTG GAAGCGTCAT AAACCAAACA    1440

GAGGAATCTC CTTATATTAA TGGCAGGTAT TATAGTAAAA TTATCATTTC CCCTGAAGAG    1500

AATGTTACAT TAACTTGCAC AGCAGAAAAC CAACTGGAGA GAACAGTAAA CTCCTTGAAT    1560

GTCTCTGCTA TAAGTATTCC AGAACACGAT GAGGCAGACG AGATAAGTGA TGAAAACAGA    1620

GAAAAGGTGA ATGACCAGGC AAAACTAATT GTGGGAATCG TTGTTGGTCT CCTCCTTGCT    1680

GCCCTTGTTG CTGGTGTCGT CTACTGGCTG TACATGAAGA AGTCAAAGAC TGCATCAAAA    1740

CATGTAAACA AGGACCTCGG TAATATGGAA GAAAACAAAA AGTTAGAAGA AAACAATCAC    1800
```

-continued

```
AAAACTGAAG CCTAAGAGAG AAACTGTCCT AGTTGTCCAG AGATAAAAAT CATATAGACC      1860

AATTGAAGCA TGAACGTGGA TTGTATTTAA GACATAAACA AAGACATTGA CAGCAATTCA      1920

TGGTTCAAGT ATTAAGCAGT TCATTCTACC AAGCTGTCAC AGGTTTTCAG AGAATTATCT      1980

CAAGTAAAAC AAATGAAATT TAATTACAAA CAATAAGAAC AAGTTTTGGC AGCCATGATA      2040

ATAGGTCATA TGTTGTGTTT GGTTCAATTT TTTTTCCGTA AATGTCTGCA CTGAGGATTT      2100

CTTTTTGGTT TGCCTTTTAT GTAAATTTTT TACGTAGCTA TTTTTATACA CTGTAAGCTT      2160

TGTTCTGGGA GTTGCTGTTA ATCTGATGTA TAATGTAATG TTTTTATTTC AATTGTTTAT      2220

ATGGATAATC TGAGCAGGTA CATTTCTGAT TCTGATTGCT ATCAGCAATG CCCCAAACTT      2280

TCTCATAAGC ACCTAAAACC CAAAGGTGGC AGCTTGTGAA GATTGGGGAC ACTCATATTG      2340

CCCTAATTAA AAACTGTGAT TTTTATCACA AGGGAGGGGA GGCCGAGAGT CAGACTGATA      2400

GACACCATAG GAGCCGACTC TTTGATATGC CACCAGCGAA CTCTCAGAAA TAAATCACAG      2460

ATGCATATAG ACACACATAC ATAATGGTAC TCCCAAACTG ACAATTTTAC CTATTCTGAA      2520

AAAGACATAA AACAGAATT                                                  2539
```

(2) INFORMATION FOR SEQ ID NO:2:

(i) SEQUENCE CHARACTERISTICS:
        (A) LENGTH: 583 amino acids
        (B) TYPE: amino acid
        (D) TOPOLOGY: linear (ii) MOLECULE TYPE: protein (ix) FEATURE:
        (D) OTHER INFORMATION: Xaa = M/S
            Xaa = M/T (xi) SEQUENCE DESCRIPTION: SEQ ID NO:2:

```
Met Glu Ser Lys Gly Ala Ser Ser Cys Arg Leu Leu Phe Cys Leu Leu
 1               5                  10                  15

Ile Ser Ala Thr Val Phe Arg Pro Gly Leu Gly Trp Tyr Thr Val Asn
            20                  25                  30

Ser Ala Tyr Gly Asp Thr Ile Ile Pro Cys Arg Leu Asp Val Pro
        35                  40                  45

Gln Asn Leu Met Phe Gly Lys Trp Lys Tyr Glu Lys Pro Asp Gly Ser
    50                  55                  60

Pro Val Phe Ile Ala Phe Arg Ser Ser Thr Lys Lys Ser Val Gln Tyr
65                  70                  75                  80

Asp Asp Val Pro Glu Tyr Lys Asp Arg Leu Asn Leu Ser Glu Asn Tyr
                85                  90                  95

Thr Leu Ser Ile Ser Asn Ala Arg Ile Ser Asp Glu Lys Arg Phe Val
            100                 105                 110

Cys Met Leu Val Thr Glu Asp Asn Val Phe Glu Ala Pro Thr Ile Val
        115                 120                 125

Lys Val Phe Lys Gln Pro Ser Lys Pro Glu Ile Val Ser Lys Ala Leu
    130                 135                 140

Phe Leu Glu Thr Glu Gln Leu Lys Lys Leu Gly Asp Cys Ile Ser Glu
145                 150                 155                 160

Asp Ser Tyr Pro Asp Gly Asn Ile Thr Trp Tyr Arg Asn Gly Lys Val
                165                 170                 175

Leu His Pro Leu Glu Gly Ala Val Val Ile Phe Lys Lys Glu Met
            180                 185                 190

Asp Pro Val Thr Gln Leu Tyr Thr Met Thr Ser Thr Leu Glu Tyr Lys
        195                 200                 205
```

```
Thr Thr Lys Ala Asp Ile Gln Met Pro Phe Thr Cys Ser Val Thr Tyr
    210                 215                 220

Tyr Gly Pro Ser Gly Gln Lys Thr Ile His Ser Glu Gln Ala Val Phe
225                 230                 235                 240

Asp Ile Tyr Tyr Pro Thr Glu Gln Val Thr Ile Gln Val Leu Pro Pro
            245                 250                 255

Lys Xaa Ala Ile Lys Glu Gly Asp Asn Ile Thr Leu Lys Cys Leu Gly
        260                 265                 270

Asn Gly Asn Pro Pro Pro Glu Glu Phe Leu Phe Tyr Leu Pro Gly Gln
    275                 280                 285

Pro Glu Gly Ile Arg Ser Ser Asn Thr Tyr Thr Leu Xaa Asp Val Arg
290                 295                 300

Arg Asn Ala Thr Gly Asp Tyr Lys Cys Ser Leu Ile Asp Lys Lys Ser
305                 310                 315                 320

Met Ile Ala Ser Thr Ala Ile Thr Val His Tyr Leu Asp Leu Ser Leu
                325                 330                 335

Asn Pro Ser Gly Glu Val Thr Arg Gln Ile Gly Asp Ala Leu Pro Val
            340                 345                 350

Ser Cys Thr Ile Ser Ala Ser Arg Asn Ala Thr Val Val Trp Met Lys
    355                 360                 365

Asp Asn Ile Arg Leu Arg Ser Ser Pro Ser Phe Ser Ser Leu His Tyr
    370                 375                 380

Gln Asp Ala Gly Asn Tyr Val Cys Glu Thr Ala Leu Gln Glu Val Glu
385                 390                 395                 400

Gly Leu Lys Lys Arg Glu Ser Leu Thr Leu Ile Val Glu Gly Lys Pro
                405                 410                 415

Gln Ile Lys Met Thr Lys Lys Thr Asp Pro Ser Gly Leu Ser Lys Thr
                420                 425                 430

Ile Ile Cys His Val Glu Gly Phe Pro Lys Pro Ala Ile Gln Trp Thr
            435                 440                 445

Ile Thr Gly Ser Gly Ser Val Ile Asn Gln Thr Glu Glu Ser Pro Tyr
450                 455                 460

Ile Asn Gly Arg Tyr Tyr Ser Lys Ile Ile Ile Ser Pro Glu Glu Asn
465                 470                 475                 480

Val Thr Leu Thr Cys Thr Ala Glu Asn Gln Leu Glu Arg Thr Val Asn
                485                 490                 495

Ser Leu Asn Val Ser Ala Ile Ser Ile Pro Glu His Asp Glu Ala Asp
            500                 505                 510

Glu Ile Ser Asp Glu Asn Arg Glu Lys Val Asn Asp Gln Ala Lys Leu
    515                 520                 525

Ile Val Gly Ile Val Val Gly Leu Leu Leu Ala Ala Leu Val Ala Gly
    530                 535                 540

Val Val Tyr Trp Leu Tyr Met Lys Lys Ser Lys Thr Ala Ser Lys His
545                 550                 555                 560

Val Asn Lys Asp Leu Gly Asn Met Glu Glu Asn Lys Lys Leu Glu Glu
            565                 570                 575

Asn Asn His Lys Thr Glu Ala
            580
```

(2) INFORMATION FOR SEQ ID NO:3:

(i) SEQUENCE CHARACTERISTICS:
        (A) LENGTH: 477 amino acids
        (B) TYPE: amino acid
        (C) STRANDEDNESS:

(D) TOPOLOGY: linear (ii) MOLECULE TYPE: protein (xi) SEQUENCE DESCRIPTION: SEQ ID NO:3:

Tyr Gly Asp Thr Ile Thr Met Pro Cys Arg Leu Glu Val Pro Asp Gly
1               5                   10                  15

Leu Met Phe Gly Lys Trp Lys Tyr Glu Met Pro Asn Gly Ser Pro Val
                20                  25                  30

Phe Ile Ala Phe Arg Ser Ser Thr Lys Lys Asn Val Gln Tyr Asp Asp
                35                  40                  45

Val Pro Asp Tyr Lys Asp Arg Leu Ser Leu Ser Glu Asn Tyr Thr Leu
            50                  55                  60

Ser Ile Lys Asn Ala Arg Ile Ser Asp Glu Lys Arg Phe Val Cys Met
65                  70                  75                  80

Leu Val Thr Glu Asp Asp Val Ser Glu Glu Pro Thr Val Val Lys Val
                85                  90                  95

Phe Lys Gln Pro Ser Gln Pro Glu Ile Leu His Gln Ala Asp Phe Leu
                100                 105                 110

Glu Thr Glu Lys Leu Lys Met Leu Gly Glu Cys Val Val Arg Asp Ser
                115                 120                 125

Tyr Pro Glu Gly Asn Val Thr Trp Tyr Lys Asn Gly Arg Val Leu Gln
            130                 135                 140

Pro Val Glu Glu Val Val Val Ile Asn Leu Arg Lys Val Glu Asn Arg
145                 150                 155                 160

Ser Thr Gly Leu Phe Thr Met Thr Ser Ser Leu Gln Tyr Met Pro Thr
                165                 170                 175

Lys Glu Asp Ala Asn Ala Lys Phe Thr Cys Ile Val Thr Tyr His Gly
                180                 185                 190

Pro Ser Gly Gln Lys Thr Ile Gln Ser Glu Pro Val Val Phe Asp Val
            195                 200                 205

His Tyr Pro Thr Glu Lys Val Thr Ile Arg Val Leu Ser Gln Ser Ser
            210                 215                 220

Thr Ile Lys Glu Gly Asp Asn Val Thr Leu Lys Cys Ser Gly Asn Gly
225                 230                 235                 240

Asn Pro Pro Gln Glu Phe Leu Phe Tyr Ile Pro Gly Glu Thr Glu
                245                 250                 255

Gly Ile Arg Ser Ser Asp Thr Tyr Val Met Thr Asp Val Arg Arg Asn
                260                 265                 270

Ala Thr Gly Glu Tyr Lys Cys Ser Leu Ile Asp Lys Ser Met Met Asp
            275                 280                 285

Thr Thr Thr Ile Thr Val His Tyr Leu Asp Leu Gln Leu Thr Pro Ser
            290                 295                 300

Gly Glu Val Thr Lys Gln Ile Gly Glu Ala Leu Pro Val Ser Cys Thr
305                 310                 315                 320

Ile Ser Ser Arg Asn Ala Thr Val Phe Trp Ile Lys Asp Asn Thr
                325                 330                 335

Arg Met Lys Thr Ser Pro Ser Phe Ser Ser Leu Gln Tyr Gln Asp Ala
                340                 345                 350

Gly Asn Tyr Ile Cys Glu Thr Thr His Lys Glu Val Glu Gly Leu Lys
            355                 360                 365

Lys Arg Lys Thr Leu Lys Leu Ile Val Glu Gly Lys Pro Gln Ile Lys
            370                 375                 380

Met Thr Lys Lys Thr Asn Thr Asn Lys Met Ser Lys Thr Ile Val Cys
385                 390                 395                 400

```
His Val Glu Gly Phe Pro Lys Pro Ala Val Gln Trp Thr Val Thr Gly
                405                 410                 415

Ser Gly Ser Leu Ile Asn Lys Thr Glu Glu Thr Lys Tyr Val Asn Gly
                420                 425                 430

Lys Phe Ser Ser Lys Ile Ile Ile Ala Pro Glu Glu Asn Val Thr Leu
                435                 440                 445

Thr Cys Ile Ala Glu Asn Glu Leu Glu Arg Thr Val Thr Ser Leu Asn
                450                 455                 460

Val Ser Ala Ile Ser Ile Pro Glu Tyr Asp Glu Pro Glu
465                 470                 475

(2) INFORMATION FOR SEQ ID NO:4:

(i) SEQUENCE CHARACTERISTICS:
        (A) LENGTH: 466 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

Tyr Gly Glu Thr Ile Val Val Pro Cys Asn Asp Gly Thr Lys Lys Pro
1               5                   10                  15

Asp Gly Leu Ile Phe Thr Lys Trp Lys Tyr Val Lys Asp Asp Gly Ser
                20                  25                  30

Pro Gly Asp Leu Leu Val Lys Gln Ala Gln Lys Asp Glu Ala Thr Val
                35                  40                  45

Ser Ala Thr Asp Gly Tyr Lys Ser Arg Val Ser Ile Ala Ala Asn Ser
50                  55                  60

Ser Leu Leu Ile Ala Arg Gly Ser Leu Ala Asp Gln Arg Val Phe Thr
65                  70                  75                  80

Cys Met Val Val Ser Phe Thr Asn Leu Glu Glu Tyr Ser Val Glu Val
                85                  90                  95

Lys Val His Lys Lys Pro Ser Ala Pro Val Ile Lys Asn Asn Ala Lys
                100                 105                 110

Glu Leu Glu Asn Gly Lys Leu Thr Gln Leu Gly Glu Cys Val Val Glu
                115                 120                 125

Asn Ala Asn Pro Pro Ala Asp Leu Ile Trp Lys Lys Asn Asn Gln Thr
                130                 135                 140

Leu Val Asp Asp Gly Lys Thr Ile Ile Ile Thr Ser Thr Ile Thr Lys
145                 150                 155                 160

Asp Lys Ile Thr Gly Leu Ser Ser Thr Ser Ser Arg Leu Gln Tyr Thr
                165                 170                 175

Ala Arg Lys Glu Asp Val Glu Ser Gln Phe Thr Cys Thr Ala Lys His
                180                 185                 190

Val Met Gly Pro Asp Gln Val Ser Glu Pro Glu Ser Phe Pro Ile His
                195                 200                 205

Tyr Pro Thr Glu Lys Val Ser Leu Gln Val Val Ser Gln Ser Pro Ile
                210                 215                 220

Arg Glu Gly Glu Asp Val Thr Leu Lys Cys Gln Ala Asp Gly Asn Pro
225                 230                 235                 240

Pro Pro Thr Ser Phe Asn Phe Asn Ile Lys Gly Lys Lys Val Thr Val
                245                 250                 255

Thr Asp Lys Asp Val Tyr Thr Leu Thr Gly Val Thr Arg Ala Asp Ser
                260                 265                 270
```

```
Gly Ile Tyr Lys Cys Ser Leu Leu Asp Asn Asp Val Met Glu Ser Thr
            275                 280                 285

Gln Phe Val Thr Val Ser Phe Leu Asp Val Ser Leu Thr Pro Thr Gly
    290                 295                 300

Lys Val Leu Lys Asn Val Gly Glu Asn Leu Ile Val Ser Leu Asp Lys
305                 310                 315                 320

Asn Ala Ser Ser Glu Ala Lys Val Thr Trp Thr Lys Asp Asn Arg Lys
                325                 330                 335

Leu Asp Lys Leu Pro Asp Phe Ser Lys Leu Thr Tyr Ser Asp Ala Gly
            340                 345                 350

Leu Tyr Val Cys Asp Val Ser Ile Glu Gly Ile Lys Arg Ser Leu Ser
        355                 360                 365

Phe Glu Leu Thr Val Glu Gly Ile Pro Lys Ile Thr Ser Leu Thr Lys
    370                 375                 380

His Arg Ser Ser Asp Gly Lys His Lys Val Leu Thr Cys Glu Ala Glu
385                 390                 395                 400

Gly Ser Pro Lys Pro Asp Val Gln Trp Ser Val Asn Gly Thr Asn Asp
                405                 410                 415

Glu Val Ser Tyr Asn Asn Gly Lys Ala Thr Tyr Lys Leu Thr Val Val
            420                 425                 430

Pro Ser Lys Asn Leu Thr Val Ser Cys Leu Val Thr Asn Lys Leu Gly
        435                 440                 445

Glu Asp Thr Lys Glu Ile Ser Val Phe Ser Gln Lys Asn Glu Asp Gly
    450                 455                 460

Thr Glu
465

(2) INFORMATION FOR SEQ ID NO:5:

(i) SEQUENCE CHARACTERISTICS:
        (A) LENGTH: 278 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:5:

Ile Gly Glu Pro Leu Val Leu Lys Cys Lys Gly Ala Pro Lys Lys Pro
1               5                   10                  15

Pro Gln Arg Leu Glu Trp Lys Leu Asn Thr Gly Arg Thr Glu Ala Trp
            20                  25                  30

Lys Val Leu Ser Pro Gln Gly Gly Pro Trp Asp Ser Val Ala Arg
        35                  40                  45

Val Leu Pro Asn Gly Ser Leu Phe Leu Pro Ala Val Gly Ile Gln Asp
    50                  55                  60

Glu Gly Ile Phe Arg Cys Arg Ala Met Asn Arg Asn Gly Lys Glu Thr
65                  70                  75                  80

Lys Ser Asn Tyr Arg Val Arg Val Tyr Gln Ile Pro Gly Lys Pro Glu
                85                  90                  95

Ile Val Asp Ser Ala Ser Glu Leu Thr Ala Gly Val Pro Asn Lys Val
            100                 105                 110

Gly Thr Cys Val Ser Glu Gly Ser Tyr Pro Ala Gly Thr Leu Ser Trp
        115                 120                 125

His Leu Asp Gly Lys Pro Leu Val Pro Asn Glu Lys Gly Val Ser Val
    130                 135                 140

Lys Glu Gln Thr Arg Arg His Pro Glu Thr Gly Leu Phe Thr Leu Gln
```

```
                145                 150                 155                 160
Ser Glu Leu Met Val Thr Pro Ala Arg Gly Gly Asp Pro Arg Pro Thr
                165                 170                 175

Phe Ser Cys Ser Phe Ser Pro Gly Leu Pro Arg His Arg Ala Leu Arg
            180                 185                 190

Thr Ala Pro Ile Gln Pro Arg Val Trp Glu Pro Val Pro Leu Glu Glu
        195                 200                 205

Val Gln Leu Val Val Glu Pro Gly Gly Ala Val Ala Pro Gly Gly
    210                 215                 220

Thr Val Thr Leu Thr Cys Glu Val Pro Ala Gln Pro Ser Pro Gln Ile
225                 230                 235                 240

His Trp Met Lys Asp Gly Val Pro Leu Pro Leu Pro Ser Pro Val
                245                 250                 255

Leu Ile Leu Pro Glu Ile Gly Pro Gln Asp Gln Gly Thr Tyr Ser Cys
            260                 265                 270

Val Ala Thr His Ser Ser
            275

(2) INFORMATION FOR SEQ ID NO:6:

(i) SEQUENCE CHARACTERISTICS:
        (A) LENGTH: 486 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:6:

Val Gly Ser Thr Ala Leu Leu Lys Cys Gly Leu Ser Gln Ser Gln Gly
1               5                   10                  15

Asn Leu Ser His Val Asp Trp Phe Ser Val His Lys Glu Lys Arg Thr
                20                  25                  30

Ser Ser Ser Val Cys Ala Arg Ala Arg Ala Arg Ala Asn Leu Gly Ser
            35                  40                  45

Thr Ser Lys Arg Leu Ser Leu Gln Asp Arg Gly Ala Thr Leu Ala Leu
    50                  55                  60

Thr Gln Val Thr Pro Gln Asp Glu Arg Ile Phe Leu Cys Gln Gly Lys
65                  70                  75                  80

Arg Leu Gly Pro Arg Ser Thr Ala Ser Ser Ala Ser Thr Lys Leu
                85                  90                  95

Arg Met Pro Asn Ile Gln Val Asn Pro Leu Gly Ile Pro Val Asn Ser
                100                 105                 110

Lys Glu Pro Glu Glu Val Ala Thr Cys Val Gly Arg Asn Gly Tyr Pro
            115                 120                 125

Ile Pro Gln Val Ile Trp Tyr Lys Asn Gly Arg Pro Leu Lys Glu Glu
        130                 135                 140

Lys Asn Arg Val His Ile Gln Ser Ser Gln Thr Val Glu Ser Ser Gly
145                 150                 155                 160

Leu Tyr Thr Leu Gln Ser Ile Leu Lys Ala Gln Leu Val Lys Glu Asp
                165                 170                 175

Lys Asp Ala Gln Phe Tyr Cys Glu Leu Asn Tyr Arg Leu Pro Ser Gly
            180                 185                 190

Asn His Met Lys Glu Ser Arg Glu Val Thr Val Pro Val Phe Tyr Pro
        195                 200                 205

Thr Glu Lys Val Trp Leu Glu Val Glu Pro Val Gly Met Leu Lys Glu
    210                 215                 220
```

```
Gly Asp Arg Val Glu Ile Arg Cys Leu Ala Asp Gly Asn Pro Pro Pro
225                 230                 235                 240

His Phe Ser Ile Ser Lys Gln Asn Pro Ser Thr Arg Glu Ala Glu Glu
            245                 250                 255

Glu Thr Thr Asn Asp Asn Gly Val Leu Val Leu Glu Pro Ala Arg Lys
            260                 265                 270

Glu His Ser Gly Arg Tyr Glu Cys Gln Ala Trp Asn Leu Asp Thr Met
        275                 280                 285

Ile Ser Leu Leu Ser Glu Pro Gln Glu Leu Leu Val Asn Tyr Val Ser
290                 295                 300

Asp Val Arg Val Ser Pro Ala Ala Pro Glu Arg Gln Glu Gly Ser Ser
305                 310                 315                 320

Leu Thr Leu Thr Cys Glu Ala Glu Ser Ser Gln Asp Leu Glu Phe Gln
                325                 330                 335

Trp Leu Arg Glu Glu Thr Asp Gln Val Leu Glu Arg Gly Pro Val Leu
            340                 345                 350

Gln Leu His Asp Leu Lys Arg Glu Ala Gly Gly Gly Tyr Arg Cys Val
        355                 360                 365

Ala Ser Val Pro Ser Ile Pro Gly Leu Asn Arg Thr Gln Leu Val Lys
370                 375                 380

Leu Ala Ile Phe Gly Pro Pro Trp Met Ala Phe Lys Glu Arg Lys Val
385                 390                 395                 400

Trp Val Lys Glu Asn Met Val Leu Asn Leu Ser Cys Glu Ala Ser Gly
            405                 410                 415

His Pro Arg Pro Thr Ile Ser Trp Asn Val Asn Gly Thr Ala Ser Glu
            420                 425                 430

Gln Asp Gln Asp Pro Gln Arg Val Leu Ser Thr Leu Asn Val Leu Val
            435                 440                 445

Thr Pro Glu Leu Leu Glu Thr Gly Val Glu Cys Thr Ala Ser Asn Asp
        450                 455                 460

Leu Gly Lys Asn Thr Ser Ile Leu Phe Leu Glu Leu Val Asn Leu Thr
465                 470                 475                 480

Thr Leu Thr Pro Asp Ser
                485

(2) INFORMATION FOR SEQ ID NO:7:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:7:

Ile Lys Glu Gly Asp
1               5

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:
```

GGCCAGATAT ACGCGTTGAC ATT                                                23

(2) INFORMATION FOR SEQ ID NO:9:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

TGTATCATGT GGATCCGCCT GGTCATTCAC CTTTTCTCT                                39

(2) INFORMATION FOR SEQ ID NO:10:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

GTACGGGCCA GATATACGCG TTGACATTGA TTA                                     33

(2) INFORMATION FOR SEQ ID NO:11:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

AGTGTCTATA GGATCCTTGC CTTCTACAAT GAGAGT                                  36

(2) INFORMATION FOR SEQ ID NO:12:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

AGTGTCTATA GGATCCAAAT CCAAATAGTG AACTGT                                  36

(2) INFORMATION FOR SEQ ID NO:13:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

AGTGTCTATA GGATCCTCTG TAGGATAGTA AATATC                                  36

(2) INFORMATION FOR SEQ ID NO:14:

```
(i) SEQUENCE CHARACTERISTICS:
    (A) LENGTH: 39 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:14:

AGTGTCTATA GGATCCAGTG CTTTGCTTAC AATTTCAGG                              39
```

ANTI-CD6 LIGAND ANTIBODIES

This is a continuation-in-part of application Ser. No. 08/432,016 filed May 1, 1995, which is a continuation-in-part of application Ser. No. 08/333,350, filed Nov. 2, 1994, U.S. Pat. No. 5,723,437, which is a continuation-in-part of application Ser. No. 08/143,903, filed Nov. 2, 1993, now abandoned, the entirety of these applications being incorporated herein by reference.

This invention was made with Government support under Grant Nos. CA-28936 and AI-07217 awarded by the National Institutes of Health. The Government has certain rights in the invention.

FIELD OF THE INVENTION

The present invention relates, in general, to CD6 and, in particular, to a CD6 ligand present on the surface of thymic epithelial cells, monocytes, activated T cells and a variety of other cell types. The invention also relates to a nucleic acid sequence encoding the CD6 ligand and to vectors and host cells comprising same. The invention further relates to methods of inhibiting the interaction of CD6 and the CD6 ligand, and to methods of screening compounds for their ability to inhibit that interaction.

BACKGROUND

CD6 is a 130 kDa glycoprotein that is homologous to CD5 and the macrophage scavenger receptor (Aruffo et al, J. Exp. Med. 174:949 (1991)). CD6 is expressed on the surface of mature thymocytes, peripheral T cells and a subset of B cells (Kamoun et al, J. Immunol. 127:987 (1981)). CD6 appears to be involved in T cell activation since monoclonal antibodies (mabs) to CD6 augment T cell receptor (TCR) mediated activation of T cells (Gangemi et al, J. Immunol. 143:2439 (1989)), and the CD6 molecule is tyrosine phosphorylated during TCR-mediated T cell triggering (Wee et al, J. Exp. Med. 177:219 (1993)). Mabs to CD6 have been shown to be clinically useful for the deletion of T cells for allogeneic bone marrow transplantation (Soiffer et al, J. Clin. Oncol. 10:1191 (1992)).

Results obtained by screening a panel of mabs to T cell surface antigens for their ability to inhibit the binding of thymocytes to human thymic epithelial cells (TEC) suggested that CD6 is involved in the binding of thymocytes to TEC (Vollger et al, J. Immunol. 138:358 (1987)). The present invention relates to a ligand for CD6 involved in that binding and to a nucleic acid sequence encoding same.

OBJECTS AND SUMMARY OF THE INVENTION

It is the general object of the invention to provide a CD6 ligand.

It is a specific object of the invention to provide a CD6 ligand in isolated form and a nucleic acid sequence encoding that ligand.

It is a further object of the invention to provide a method of inhibiting the binding of CD6 to a CD6 ligand.

It is yet another object of the invention to provide a method of screening compounds for their ability to inhibit CD6/CD6 ligand binding.

It is a further object of the invention to provide a monoclonal antibody specific for a CD6 ligand.

In one embodiment, the present invention relates to an isolated CD6 ligand, including both divalent cation dependent and divalent cation independent forms thereof. The invention further relates to mimetopes of such a ligand.

In another embodiment, the present invention relates to a nucleic acid sequence encoding a CD6 ligand and to a vector and host cell comprising same. The invention also relates to a method of producing a CD6 ligand or a portion thereof that comprises culturing a host cell comprising a CD6 ligand encoding sequence or a portion thereof under conditions such that the sequence is expressed and the CD6 ligand or portion thereof is thereby produced.

In a further embodiment, the present invention relates to a method of inhibiting binding of CD6 present on the surface of a first cell to CD6 ligand present on the surface of a second cell. The method comprises contacting the CD6 present on the surface of the first cell with a soluble CD6 ligand, or mimetope thereof, under conditions such that the soluble CD6 ligand, or mimetope thereof, binds to the CD6 present on the surface of the first cell and thereby inhibits binding of the CD6 ligand present on the surface of the second cell to the CD6 present on the surface of the first cell. Alternatively, the method comprises contacting the CD6 ligand present on the surface of the second cell with soluble CD6, or mimetope thereof, under conditions such that the soluble CD6, or mimetope thereof, binds to the CD6 ligand present on the surface of the second cell and thereby inhibits binding of the CD6 present on the surface of the first cell to the CD6 ligand present on the surface of the second cell.

In another embodiment, the present invention relates to a method of screening a test compound for the ability to inhibit binding of CD6 to CD6 ligand. The method comprises: i) contacting the test compound with one of CD6 and CD6 ligand under conditions such that a complex between the test compound and the CD6 or CD6 ligand can form, ii) contacting the combination of CD6 or CD6 ligand and test compound resulting from step (i) with the other of CD6 and CD6 ligand under conditions such that complexation between the CD6 and the CD6 ligand can occur, and iii) determining the extent of complexation between the CD6 and the CD6 ligand and thereby the ability of the test compound to inhibit binding of the CD6 to the CD6 ligand.

In yet a further embodiment, the present invention relates to anti-CD6 ligand antibodies and antigen binding fragments thereof that can be produced enzymatically (eg Fab and $F(ab)_2$ fragments) and to CD6 ligand specific binding proteins that can be produced recombinantly (eg fusion proteins and chimeric antibodies).

Further objects and advantages of the present invention will be clear from the description that follows.

BRIEF DESCRIPTION OF THE DRAWINGS

FIG. 6A shows the pattern of reactivity to T12 and FIG. 6B shows the pattern of reactivity to mab J4-81. At least three different thymus tissues were analyzed with similar results. CD6 was expressed on thymocytes in the medulla (med) and moderately on thymocytes in the cortex (ctx). Mab J4-81 detected medullary thymic epithelial cells and Hassal's bodies (HB).

(FIG. 9A) The binding of increasing concentrations of CD6-Rg and CD5-Rg to the breast carcinoma cell line HBL-100 was examined by flow cytometry. The percentage binding (ordinate) was determined as described in FIG. 8. A total of $10^4$ cells were examined at each protein concentration. (FIG. 9B) The binding of CD6-Rg to HBL-100 cells which were pretreated with trypsin was compared to the binding of CD6-Rg and CD5-Rg to untreated HBL-100 cells by flow cytometry. This figure shows the results of a representative experiment out of three. Trypsin digests were carried out as described.

(FIG. 14A) CD6-Rg binding to skin. Scattered cells in the dermis are labeled. Nonspecific labeling of hair shafts is indicated by arrows. (FIG. 14B) Reactivity of human IgG1 with a serial skin section. Only weak labeling of hair shafts is evident (arrows). (FIG. 14C) Reactivity of CD6-Rg with thymus tissue. A delicate reticular labeling pattern is present in the cortex. (FIG. 14D) Reactivity of human IgG1 with thymus tissue. Only faint background labeling was detected. (FIG. 14E) Reactivity of CD6-Rg with lymph node. Cells in the intermediate or paracortical sinuses were labeled. (FIG. 14F) No binding of human IgG1 to lymph node tissue was observed.

FIG. 16A depicts the amount of rosette formation in the presence of specific antibodies and (FIG. 16B) depicts the amount of rosette formation in the presence of fusion proteins. Standard errors are indicated by bars. Both anti-CD6 antibody and CD6-Rg fusion protein partially inhibit TE-thymocyte binding: T12 inhibited rosette formation by 49±9% and CD6-Rg inhibited rosette formation by 35±9%. The differences in binding between control and 35.1 ($p<0.003$), T12 ($p<0.015$) and CD6-Rg ($p<0.05$) were statistically significant.

FIGS. 21G and 21H show composite summary histograms of CD6-Rg binding in the presence of either P3, J4-81 or J3-119. Data are representative of 10 experiments in the presence of divalent cations (FIG. 21G) and 2 experiments with no divalent cations (FIG. 21H).

FIG. 24A shows a section of thymus stained by indirect IF with mAb J4-81. FIG. 24A shows a section of thymus cortex and FIG. 24B shows a section of thymus medulla with Hassall's bodies (HB). The thymic capsule is indicated by dashed lines in FIG. 24A. Thymic epithelial cells (arrows), in both the cortex and in and around HB in medulla, reacted with mAb J4-81. Thymocytes did not react with mAb J4-81. An identical pattern was seen using mAb J3-119 (not shown) (400× magnification).

FIG. 25A. Histograms of CD6 expression on COS-neo (control) and COS-CD6 cells were determined by indirect immunofluorescence with the anti-CD6 mAb T12 (Gangemi et al, J. Immunol. 143:2439-2447 (1989)) (solid line) or a control antibody P3 (dotted line). FIG. 25B. The bar graph (FIG. 25C)depicts COS-neo and COS-CD6 binding to TE cells in the presence of either the T12, J4-81 or P3 mAbs. Shown are the mean and SEM of three separate experiments.

FIGS. 26A to 26C. Sequence analysis of the predicted amino acid sequence of the CD6 ligand designated ALCAM, Northern analysis of ALCAM mRNA expression, and ALCAM cell surface expression by activated T cells. FIG. 26A. Alignment of the immunoglobulin-like extracellular domains of ALCAM (residues 35–512) (residues 35 to 512 of SEQ ID NO:2), BEN (SEQ ID NO:3), neurolin (SEQ ID NO:4), RAGE (SEQ ID NO:5) and MUC18 (SEQ ID NO:6). The lower case letter in front of the protein name designates the species (human, h, chicken, c, and fish, f). Consensus residues are those shared by three or more proteins (SEQ ID NO:7). Invariant residues are shown shaded and Cys's are highlighted with an asterisk. The numbering of the peptide sequences shown, obtained from published manuscripts, are as follows: cBEN, 8-484 (Pourquie et al, Proc. Natl. Acad. Sci. USA 89:5261 (1992)); neurolin, 1–466 (Lawssing et al, Differentiation 56:21 (1994)); RAGE, which contains three Ig domains, 30–307 (Neeper et al, J. Biol. Chem. 267:14998 (1992)); MUC18, 40–525 (Lehmann et al, Proc. Natl. Acad. Sci. USA 86:9891 (1989)). FIG. 26B. 15 μg of total RNA from peripheral blood monocytes and 25 μg of total RNA from resting and PHA activated (72h) peripheral blood mononuclear cells, the T cell lymphomas CEM and MOLT4, the erythroleukemia cell line K562, the B cell lymphomas RAMOS, RAJI and DAUDI, the myelo-monocytic cell lines HL60 and U937, the large granular lymphoma YT, the human breast carcinoma HBL-100 and COS cells were used to prepare an RNA blot. Random primed $^{32}$P-labeled ALCAM or glyceraldehyde 3-phosphate dehydrogenase (GAPDH) cDNA's were used as probes. FIG. 26C. Peripheral blood mononuclear cells were activated in vitro with PHA and the ability of T cells to bind to either CD6-Rg or J4-81 was monitored for a period of ten days by two color immunofluorescence and flow cytometry. The mean channel fluorescence vs. day was plotted.

FIGS. 28A and 28B. Binding of ALCAM to CD6. FIG. 28A. Flow cytometry histograms showing the binding of the anti-ALCAM mAb J4-81 and the CD6-Rg fusion protein to COS cell transfectants expressing ALCAM. FIG. 28B. Flow cytometry histograms showing the binding of anti-CD6 mAb G3-6 and ALCAM-Rg to COS cell transfectants expressing CD6. The level of background binding of mAB's or fusion proteins to mock transfected COS cells is shown by shaded histograms.

FIGS. 29A and 29B. ALCAM encoding sequence and predicted amino acid sequence (SEQ ID NO:1 and SEQ ID NO:2).

DETAILED DESCRIPTION OF THE INVENTION

Figure 29A:
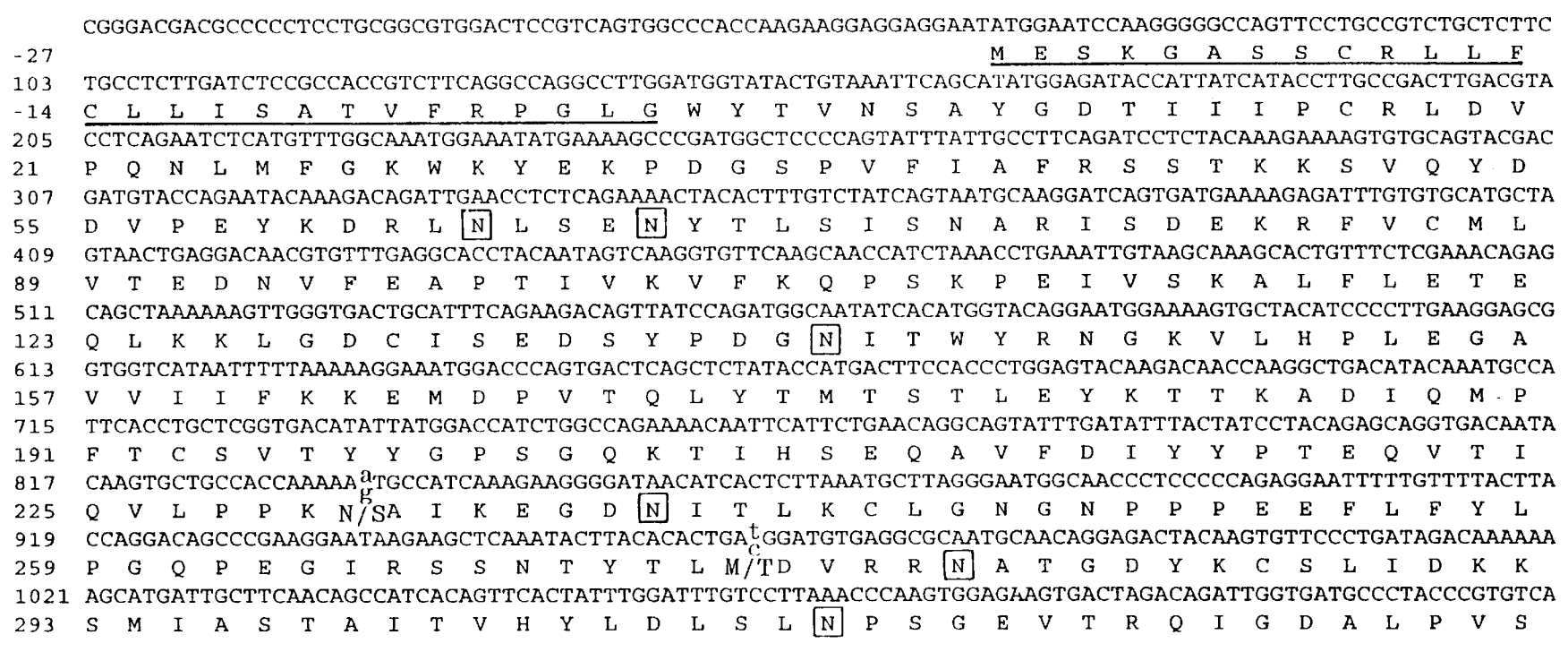

The present invention relates to a molecule that represents one member of a binding pair, the other member of that pair being the CD6 molecule present on the surface of mature thymocytes, peripheral T cells and a subset of B cells. The CD6 ligand, as it is referred to herein, occurs in two forms—one form is independent of divalent cations for CD6 binding, the other is divalent cation-dependent. The first of these forms (the cation-independent form) comprises a 105 kDa protein (as determined by SDS-PAGE under reducing conditions) and is termed activated leucocyte-cell adhesion molecule (ALCAM). The second form is divalent cation-dependent, is a distinct molecule separate from ALCAM, and comprises a 90 kDa protein (determined by SDS-PAGE under reducing conditions). The molecular weight of ALCAM based on the predicted amino acid sequence shown in FIG. 29 is about 65 kDa. The amino acid sequence of ALCAM shown in FIG. 29 includes 9 potential sites for N-linked glycosylation. Thus, the glycosylated form of the ALCAM CD6 ligand can be expected to have a molecular weight of 100–105 kDa.

Figure 30:
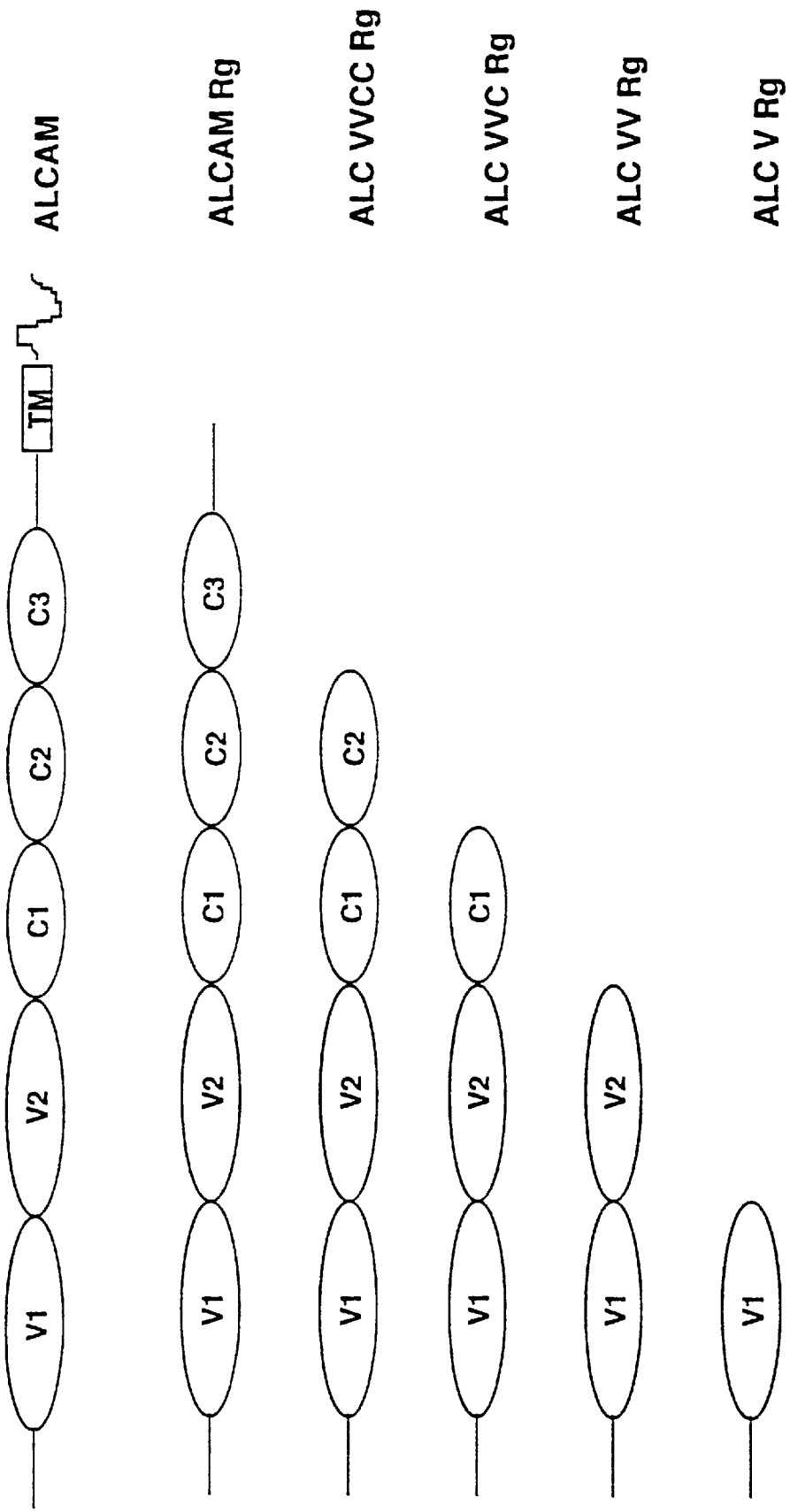
FIG. 30. Domains of ALCAM and truncated forms thereof.

ALCAM consists of an N-terminal hydrophobic signal peptide, which is cleaved from the mature protein, followed by an extracellular domain, a hydrophobic transmembrane domain and a cytoplasmic domain. Single domains or combinations of domains can be used to inhibit a variety of interactions. For example, extracellular domains, separately or in combination with each other or other sequences, can be expected to be useful products for inhibiting CD6-ALCAM interactions. The extracellular domain of ALCAM can be divided into 5 immunoglobulin (Ig)-like domains. The two N-terminal domains are of the V-set, the three Ig domains that follow are of the C2-set (Pourquie et al, Proc. Natl. Acad. Sci. USA 89:5261 (1992); Tanaka et al, Neuron 7:535 (1991); Burns et al, Neuron 7:209 (1991). (See FIG. 30.) These Ig-like domains can be used in isolation or in combination with other sequences.

The CD6 ligand (ALCAM) of the invention is present on a variety of tissue and cell types, including fibroblasts, skin epidermal keratinocytes, medullary TEC, gut epithelium, pancreas islet and acinar cells, as well as monocytes and activated T cells, hepatocytes and neurons of the brain cortex. The tissue distribution of the CD6 ligand indicates that the CD6/CD6 ligand system is important for mediation of T cell interactions with monocytes and other activated T cells as well as with epithelial cells, fibroblasts and specialized cells, such as pancreatic islet cells. The expression of CD6 and CD6 ligand in brain indicates that the CD6/CD6 ligand system is involved in interactions between cells of the nervous system.

The CD6 ligand of the invention can be isolated from natural sources (see above) by immunoprecipitation, for example, with a CD6 fusion protein as described in the Examples that follows. A suitable fusion protein, the CD6-Ig (=CD6-Rg) fusion protein, can be produced by ligating the coding sequence of the extracellular portion of CD6 (Aruffo et al, J. Exp. Med. 174:949 (1991)) to the coding sequence of the Fc portion of human IgG as described by Seed and Aruffo (Proc. Natl. Acad. Sci. USA 84:3365 (1987)). The CD6-Ig fusion protein can be expressed in COS cells by transient transfection as previously described (Seed and Aruffo, Proc. Natl. Acad. Sci. USA 84:3365 (1987)).

The availability of the CD6 ligand protein from cell sources, including those noted above, makes possible the cloning of the CD6 ligand gene(s). Sequencing of all or part of the CD6 ligand protein provides the information necessary for designing nucleic acid probes or primers suitable for use in isolating the CD6 ligand coding sequence(s), for example, from cDNA or genomic DNA libraries. The Unizap XR system from Stratagene can be used to prepare a suitable cDNA library from thymic epithelial cells. Other libraries that can be used include the brain frontal cortex and liver tumor Hep G2 cDNA libraries from Stratagene.

More specifically, the CD6 ligand can be purified by affinity chromatography. Anti-CD6 ligand mab (5–10 mg) (see, for example, Pesando et al, J. Immunol. 137:3689 (1986)) can be used to prepare an affinity column for CD6 ligand by immobilization of anti-CD6 ligand protein on Sepharose (Bowen et al, J. Immunol. 151:5891 (1993)) or CNBr-activated Sepharose 4B (Pharmacia), as described by Patel et al (Virology 149:174 (1986)). CD6 ligand from protein lysates of, for example, breast carcinoma cells (eg HBL-100), thymic epithelial cell or B lymphoma cell line lysates, can be affinity purified using the anti-CD6 ligand Sepharose column. CD6 ligand can be further purified over a $C_{18}$ reverse phase HPLC column (Vydac) using acetonitrile/$H_2O$ gradients containing trifluoroacetic acid with UV detection at 240nm. (Example IV includes a description of the J4-81 immunopurification of CD6 ligand from breast carcinoma cells. Examples V and VI include a description of the preparation of antibodies to four additional epitopes of ALCAM.) Once purity has been established, the N-terminal amino acid sequence of intact CD6 ligand, and peptides generated with V8-protease, trypsin or other proteases, can be determined. From the amino acid sequence, degenerate oligonucleotide primers can be designed that recognize cDNA for CD6 ligand, to PCR amplify CD6 ligand cDNA. To guard against errors in the PCR amplification, $^{32}$P-labelled PCR amplified CD6 ligand cDNA can be used as a probe to detect CD6 ligand cDNAs from an appropriate cDNA library. The nucleotide sequence of CD6 ligand cDNA can be determined using standard methodologies. (See generally, Sambrook, Fritsch and Maniatis, Molecular Cloning: A Laboratory Manual, 2nd Edition, Cold Spring Harbor Laboratory Press (1989).)

Example IV includes a description of the analysis of purified ALCAM and CNBr fragments thereof in a pulsed-liquid protein sequencer. The amino acid sequences from intact protein and internal fragments are homologous with the chicken neuronal adhesion molecule BEN/SC-1/DM-GRASP. Example IV describes the use of DNA fragments corresponding to chicken BEN to isolate CD6 ligand cDNA. The ALCAM cDNA sequence and predicted amino acid sequence are shown in FIG. 29.

Once cloned, the CD6 ligand encoding sequence can be introduced into a host cell, for example, in an expression construct (eg, wherein the vector is a viral or plasmid vector) in operable linkage with a promoter. The construct can be used to transform a procaryotic or eucaryotic host cell. Eucaryotic hosts are preferred since the CD6 ligand is a glycosylated protein. Mammalian cell systems are particularly advantageous (eg, the COS M6 system or the Chinese hamster ovary (CHO) cell system). The CD6 ligand can be produced in soluble form by culturing the host cells transfected with a gene encoding CD6 ligand protein (eg, an Ig fusion protein) under conditions such that the encoding sequence is transcribed and the transcript is translated into protein.

The present invention relates to the CD6 ligand in its entirety and also to portions thereof suitable, for example, for use as antigens that can be used in standard immunization protocols to generate antibodies (monoclonal (see Examples V and VI) or polyclonal) (or binding fragments thereof) specific for the CD6 ligand (the ligand and the portions can be synthesized chemically or recombinantly). Such portions represent at least 5 consecutive amino acids of the CD6 ligand (eg of the ALCAM sequence shown in FIG. 29), preferably, at least 10 or 12 amino acids, more preferably, at least 25 consecutive amino acids, most preferably at least 40, 45 or 50 amino acids. Larger portions can also be used, for example, portions of at least 100, 250 or 500 amino acids. The invention includes portions of the CD6 ligand corresponding to the signal sequence, or the extracellular, transmembrane or cytoplasmic domain (or subunits of these domains such as the immunoglobulin variable region-like domain (V) and immunoglobulin constant region-like domain (C) subunits of the extracellular domain), alone or in combination with other CD6 ligand domain sequences or non-CD6 ligand sequences.

The invention also relates to a CD6 ligand encoding sequence (DNA or RNA) in its entirety and to portions thereof suitable for use, for example, as probes or primers (hybridization conditions described as standard by Strategene and/or Gibco (eg for PCR) can be used). Such portions represent at least 15, 20, 30, 75 or 150 nucleotides of the CD6 ligand (for example, of the sequence given in FIG. 29). Larger portions can also be used, for example, portions of at least 300, 750 or 1500 nucleotides. The invention includes portions of the CD6 ligand encoding sequence corresponding to the signal sequence or the extracellular, transmembrane, or cytoplasmic domain. Such portions can be present in various combinations and in combination with non-CD6 ligand encoding sequences (eg, ALCAM-Rg).

Ligation of CD6 on T cells by anti-CD6 mab provides a potent co-mitogenic signal for unseparated T cells (Gangemi et al, J. Immunol. 143:2439 (1989); Morimoto et al, J. Immunol. 140:2165 (1988); Wee et al, J. Exp. Med. 177:219 (1993)), directly activates separated CD4+ T cell clones (Swack et al, J. Biol Chem. 266:7137 (1991)), and directly activates TCRγδ but not TCRαβ T cells (Pawlec et al, Hum. Immunol. 31:165 (1991)). Thus, CD6 is a molecule of mature T cells that is intimately involved in TCR mediated T cell triggering; ligation of the TCR complex leads to CD6 phosphorylation (Wee et al, J. Exp. Med. 177:219 (1993)). Methods of inhibiting CD6/CD6 ligand interactions in vivo provides a potent immunotherapeutic strategy.

Soluble CD6 ligand (isolated from natural sources or produced recombinantly) can be used, for example, to inhibit CD6-mediated T cell activation that is dependent on T cell CD6-CD6 ligand+accessory cell contact. A portion of the CD6 ligand can also be used; for example, a domain such as the extracellular domain can be used alone or in combination with other domains or other sequences. Such an immunotherapeutic regimen is useful in treating diseases caused by activated T cells such as multiple sclerosis, inflammatory uveitis, including Cogan's syndrome, rheumatoid arthritis, T cell mediated vasculitis syndromes, such as Wegener's granulomatosis and temporal arteritis, and organ allograft rejection. Indeed, it has been shown that CD6 mab depletion of bone marrow (BM) used for allogeneic EM transplant prevents graft versus host disease (Soiffer et al, J. Clin. Oncol. 10:1191 (1992)).

In addition to soluble CD6 ligand, soluble CD6, as well as mimetopes (mimics) of CD6 and CD6 ligand (prepared, for example, as described by Szostak (TIBS 17:89 (1992)) or Tsai et al (J. Immunol. 150:1137 (1993)), for example, from random RNA, DNA or peptide libraries), can be used as immunotherapeutic agents in regimens involving inhibiting CD6/CD6 ligand interaction. Anti-CD6 and anti-CD6 ligand antibodies (preferably monoclonal antibodies (see Examples V and VI)) can also be used in such regimens. These immunotherapeutic agents can be formulated with, for example, a pharmaceutically acceptable carrier, diluent, etc., as a pharmaceutical composition. The concentration of active agent in the composition and the amount of active agent adminstered will vary with the agent, the patient and the effect sought. Optimum doses can be readily determined.

The demonstration that CD6-CD6 ligand interactions mediate the adhesion of CD6 expressing cells to TE cells indicates that CD6-CD6 ligand binding plays a role in regulating T cell maturation. Other molecules including CD2/LFA-3, ICAM-1/LFA-1, VLA-3, -4, -6, and fibronectin can serve as adhesion molecules in thymocyte-stromal cell binding (Singer et al, J. Immunol. 144:2931–2939 (1990), Giunta et al, J. Exp. Med. 173:1537–1548 (1991), Utsumi et al, Proc. Natl. Acad. Sci. USA 88:5685–5689 (1991)). The identification of a CD6 ligand permits determination of the relative contribution of CD6 in thymocyte-TE cell binding and T cell maturation. CD6-ligand may also be involved in B cell development, since studies in the chicken showed that ALCAM (BEN) is expressed on endothelial cells in the bursa of Fabricius (Pourquie et al, Development 109:743–752 (1990)), which is an organ in birds where B cells develop. Presently, there is no information on the ability of CD6 ligand to transduce intracellular signals. The finding that the anti-CD6 mAB T12 can activate T cells in the presence of accessory cells and in the apparent absence of crosslinking FcR's, indicates that activation of T cells by signaling through CD6 is important in autoimmune reactivity (Gangemi et al, J. Immunol. 143:2439–2447 (1989)). In support of this, anti-CD6 mAB's can enhance or inhibit the autologous MLR (Gangemi et al, J. Immunol. 143:2439–2447 (1989), Bott et al, Int. Immunol. 7:783–792 (1994)) (Singer, N. G. et al, J. Immunol. (1994)). Since CD6 ligand is expressed by activated T cells and monocytes as well as by a number of T and B cell lines, CD6-CD6 ligand interactions would appear to play a role in functional interactions between CD6+T and B cells and activated leukocytes and CD6-CD6 ligand binding would appear to mediate adhesive interactions among activated leukocytes. Thus, while ALCAM may not affect the initiation of an inflammatory response, it may inhibit maintenance of a chronic inflammatory response, such as rheumatoid arthritis.

ALCAM (BEN) in the chicken is expressed predominantly during early embryonic development and in the brain (Pourquie et al, Development 109:743–752 (1990)). ALCAM functions as a homophilic adhesion molecule and supports neurite outgrowth (Tanaka et al, Neuron 7:535–545 (1991), Burns et al, Neuron 7:209–220 (1991)). Expression of human ALCAM by neurons in the brain has been reported (Patel et al, "Identification and characterization of an 100 kDa ligand for CD6 on human thymic epithelial cells", J. Exp. Med. (1994)). Interactions between the immune and nervous system are important in the pathology of certain chronic neurodegenerative diseases such as multiple sclerosis, Alzheimer's disease, and amyotrophic lateral sclerosis (Appel et al, Advances in Neurology 56:405–412 (1991), McGeer et al, Can. J. Neurol. Sci. 18:376–379 (1991), Rowland, L. P., Advances in Neurology 56:3–23 (1991)). The finding that CD6 and CD6 ligand are both expressed by cells in these systems indicate that this receptor/ligand pair functions in cellular interactions between the immune and nervous systems.

For example, since inflammation requires amplification of immune responses, blocking CD6 binding can be expected to prevent immune response amplification and inflammation. Further, inhibition of leukocyte interactions with cells of the brain can be used to treat chronic neurodegenerative diseases. Mutations in ALCAM can be expected to lead to disorders of the nervous and/or immune systems. When such disorders are identified, the CD6 ligand nucleotide sequence or RFLP's (restriction fragment length polymorphisms) identified for the CD6 ligand can be used as markers for candidate gene searches. For example, since ALCAM is expressed on motor neuron's and immune cells, candidate diseases to screen for ALCAM mutations are sporadic cases of amyotropic lateral sclerosis and multiple sclerosis.

In addition to the above, it will be appreciated from a reading of this disclosure that soluble ALCAM, for example, can be used to induce regeneration of damaged or severed nerves. Induction can be effected by administering soluble ALCAM at the site of nerve damage, for example, by injection.

The CD6 ligand gene is a potential candidate for mutations in Mendelian disorders affecting the nervous sytem and immune system. No disease suggestive for further testing has yet been mapped to that region of human chromosome 3 to which the CD6 ligand gene has been assigned. The polymorphisms identified in the CD6 ligand cDNA can be used for candidate gene exclusion studies. (Polymorphisms noted may result from the fact that cDNAs were obtained from a PHA activated cDNA library and HL60 cells. Different donor sources often show polymorphisms in genes.)

Certain aspects of the invention are described in greater detail in the non-limiting Examples that follows.

EXAMPLE I

Experimental details:

Cells and culture conditions. TEC were cultured by the explant technique in enriched media as previously described (Singer et al, Human Immunol. 13:161 (1985)). Human thymus tissue was obtained from the Department of Pathology, Duke University Medical Center, as discarded tissue from children undergoing corrective cardiovascular surgery. Contaminating thymic fibroblasts were removed by complement mediated lysis with mAb 1B10 which binds to a cell surface antigen on human fibroblasts (Singer et al, J. Invest. Dermatol. 92:166 (1989)) followed by treatment with 0.02% EDTA in PBS. 3T3 fibroblast feeder layers were removed by treatment with 0.02% EDTA in PBS prior to detachment of TEC from culture dishes with 0.05% trypsin in PBS containing 0.02% EDTA. Cells were washed 3 times prior to analysis. TEC were activated with 500 U/ml IFN-γ in DMEM containing 5% FCS, 1 mM sodium pyruvate (Gibco) 0.025 µg/ml amphotericin B (Gibco), 100 U/ml penicillin and 1000 µg/ml streptomycin for 48–72h at 37° C.

Thymocytes were obtained by teasing from thymus tissue, purified by centrifugation through ficoll-hypaque and washed with RPMI 1640. Thymocytes were used immediately or frozen in media containing 20% FCS, 7.5% DMSO and 10 µg/ml gentamicin (Scherring) in RPMI 1640. Frozen thymocytes were thawed by incubation in media containing 30% FCS, 10 µg/ml deoxyribonuclease I (Sigma), 10 µg/ml gentamicin and 20 U/ml heparin (Upjohn) in RPMI 1640 as described (Denning et al, J. Immunol. 138:680 (1987)). Viable thymocytes were purified by centrifugation through ficoll-hypaque.

COS-M6 cells (ATCC) were grown in DMEM containing 10% FCS, 1 mM sodium pyruvate (Gibco), 0.025 µg/ml amphotericin B (Gibco), 100 U/ml penicillin and 100 µg/ml streptomycin.

Human epidermal keratinocytes (EK) were cultured from neonatal foreskins. Foreskins were incubated at 4° C. overnight in 2.5 mg/ml trypsin type III (Sigma) in HBSS (GIBCO), the epidermis was removed, teased into a single cell suspension, seeded onto mitomycin C treated 3T3 fibroblast feeder layers and cultured as described (Hashimoto et al, J. Exp. Med. 157:259 (1983)).

Detection of cell surface antigens: Unfixed cultured cells were suspended in either PBS, TBS (0.9 M NaCl, 50 mM Tris-HCl, pH 7.3) or DMEM containing 2% BSA and 0.1% NaN$_3$. Cells were incubated with CD6-Rg, CD5-Rg or ELAM-Rg (from Sandro Aruffo, Bristol-Myers Squibb), recombinant fusion proteins (100 µg/ml) for 30 min at 4° C. and washed with PBS containing 2% BSA and 0.1% NaN$_3$. FITC conjugated goat anti-human IgG$_1$ was used as a secondary reagent. Cells were analyzed on a FACStar Plus flow cytometer (Becton-Dickinson, Inc., Mountain View, Calif.) and data was processed using the software program PC-Lysys (Becton-Dickinson).

TEC-thymocyte rosette binding assay: TEC-thymocyte rosette binding assays were performed as described (Singer et al, Proc. Natl. Acad. Sci. USA 83:6588 (1986)). Briefly, 10$^6$ thymocytes were mixed with 2×10$^5$ TEC in PBS or DME containing 2% BSA and 0.1% NaN$_3$, centrifuged for 3 min at 250 g, and incubated for 60 min at 4° C. Cells were gently resuspended and counted under light microscopy. TEC which bound 3 or more thymocytes were scored as positive. The thymocytes used in these experiments were either freshly isolated, thawed from liquid nitrogen, or separated into subpopulations. Thymocytes were separated into CD1$^+$ (immature, CD6$^{low}$) or CD1$^-$ (mature, CD6$^{hi}$) subpopulations by indirect immunofluorescent staining with Na1/34 (anti-CD1; from Andrew McMichael, Oxford, England) and goat anti-mouse IgG (KPL) followed by fluorescence activated cell sorting using a FACStar Plus. All thymocyte subpopulations were >95% pure on reanalysis of sorted cells. TEC-thymocyte binding was inhibited by pre-incubation of either thymocytes or TEC with antibodies or fusion proteins prior to binding. Antibodies used were: P3X63 (control mab) (ATCC), 35.1 (anti-CD2; from John Hansen, Seattle, Wash. (Martin et al, J. Immunol. 131:180 (1983)) and T12 (anti-CD6; from Ellis Reinherz, Boston, Mass. (Reinherz et al, *Cell* 30:735 (1982)).

COS cell transfection and binding studies: Stable lines of CD6-expressing COS cells were made by co-transfection of plasmids containing the CD6 gene under the control of the CMV promoter (A. Aruffo, Seattle, Wash., Aruffo et al, J. Exp. Med. 174:949 (1991)) and the pSVneo plasmid containing the bacterial neomycin resistance gene driven by an SV40 promter as described by Liao et al (J. Immunol. Dec 1, 1993). Cells expressing the neomycin resistance gene were selected by incubation in DME/10%FCS containing 60µg/ml G418 (GIBCO). Cells expressing CD6 were identified by indirect immunofluorescence using mab T12. CD6 positive and negative cells were cloned by single cell sorting using a Becton-Dickinson FACStar$^{Plus}$ flow cytometer.

CD6-expressing COS cells (COS-CD6D) and control COS cells (COS-Neo) were used in binding studies, with TE cells similar to those outlined above. To differentiate between COS cells and TE cells, TE cells were metabolically labelled with 1 µg/ml calcein AM (Molecular Probes, Eugene, Oreg.) for 15 min at 37° C. in PBS prior to harvest. Calcein AM-labelled cells are fluorescent and can be easily differentiated from other cells by fluorescence microscopy.

Construction of the CD6-Rg (CD6-Ig) chimeric gene and preparation of the fusion protein: The CD6 immunoglobulin fusion gene was constructed by digesting a plasmid containing the cDNA encoding the full-length CD6 (Aruffo et al, J. Exp. Med. 174:949 (1991)) with the restriction enzyme Esp1. The Esp1 digested plasmid was then flushed with DNA polymerase and the appropriate Bam HI linkers were added to it. The plasmid was then digested with Bam HI and Nde 1. The fragment that contained the extracellular domain of CD6 was then isolated and subcloned into a vector containing a cDNA fragment encoding the constant domain of a human IgG1 protein (Aruffo et al, Proc. Natl. Acad. Sci. USA 89:2292 (1992)). The constructions of CDS-Ig and CTLA4-Ig have been described elsewhere (Linsley et al, Science 257:792 (1992) and J. Exp. Med. 174:561 (1991)). 500 µg of DNA of the appropriate gene was transfected into COS cells by the DEAE-dextran chloroquine method. 18–24 hrs later, the 10% FBS Dulbeco's modified Eagle's medium was replaced by serum-free media after a rinse wash with PBS. The cell culture was maintained 7–10 days before it was harvested. Briefly, the supernatant containing the fusion protein was centrifuged at 2500 rpm for 20 min and filtered through a 0.45 µm Millipore filter. The supernatant was passed over a 2-ml packed Protein A column at a flowrate of 1.00 ml/min. The bound fusion protein was eluted with pH 3.5, 0.1 M citric acid and was immediately neutralized with pH 9.0, 1.0 M Tris. The eluted protein was then dialyzed overnight in PBS and protein determination was done using the Bradford method.

Screening of nabs for inhibition of CD6-Ig binding to TE cells: Mabs from the 5th International Workshop on Human Leukocyte Differentiation Antigens and a panel of anti-integrin mabs (see description of FIG. 4) were screened for reactivity to the surface of TE cells as outlined above, using fluorescein-conjugated goat anti-mouse IgG (KPL) as a secondary reagent. Of the 154 mabs that reacted to TE cells, 126 were used in this assay. TE cells (look) were incubated with ascites or purified mab at 1:100 for 15 min at 4° C. Either CD5-Ig or CD6-Ig (5 µg) was added to this mixture and allowed to react for 2 hr at 4° C. After washing with PBS-containing 2% BSA, CDS-Ig and CD6-Ig were labelled with a fluorescein conjugated goat antiserum specific for the Fc protein of human IgG (Sigma). This reagent did not cross react with most murine mabs. To account for any cross-reactivity that may have occurred, binding was determined to be the difference in fluorescence (ΔFL) between samples containing CD6-Ig and CD5-Ig. The ΔFL of samples pre-incubated with control mab P3 was considered to represent 100% binding.

Immunoprecipitation and protein labelling conditions: 120 µCi/ml glucosamine (NEN) was used in the labelling experiment. The cells were cultured in glucose-free media plus 10% dialyzed fetal calf serum for 48 hrs upon addition of the radiolabelled glucosamine. The cells were then lifted with EDTA, washed in HBSS and lysed in 20 mM Tris, pH 7.5 containing leupeptin, PMSF and pepstain (1 µg/ml), 0.05% sodium cholate, 2% NP-40. The lysate was pre-cleared with 100 µg/ml human IgG1 followed by 50 µl of Protein A beads. Pre-cleared lysates were then incubated with 50 µg/ml CD6-Rg or CTLA4-Ig or 2 µg/ml anti-EGF receptor antibody and Protein A Sepharose. 2 mM Ca$^{++}$ and Mg$^{++}$ were added to the lysates (this is the concentration of divalent cations contained in the HBSS binding buffer). The immunoprecipitates were washed 3× in lysis buffer, 2× in PBS, boiled in reducing SDS-PAGE loading buffer and loaded unto a 8–10.5% SDS-PAGE gel. The gels were fixed in 40% isopropanol, enhanced in m AMiAmplify$^R$ reagent (Amersham), dried and autoradiographed.

Results:

Anti-CD6 mabs and CD6-Ig fusion proteins inhibit TE-thymocyte binding: Using a suspension TE-thymocyte binding assay (Table 1), it was found that the CD6 mab T12 inhibited TE-thymocyte binding by 49±9% (N=5). Similarly, recombinant CD6-Ig fusion protein inhibited TE-thymocyte binding by 35±9% (N=5). This suggested that human TEC express a ligand for CD6.

TABLE 1

Effect of monoclonal antibodies and fusion protein
on thymocyte-thymic epithelial cell binding

| mab/fusion protein | % Binding[a] | % Inhibition[b] | |
|---|---|---|---|
| P3 | 32.8 ± 5.2 | 0 | |
| 35.1 (anti-CD2) | 8.2 ± 2.4 | 76.0 ± 5.4 | p < 0.003 |
| T12 (anti-CD6) | 17.2 ± 3.8 | 48.7 ± 9.2 | p < 0.015 |
| ELAM-IG | 29.7 ± 3.6 | 0 | |
| CD6-IG | 19.3 ± 3.2 | 34.5 ± 9.3 | p < 0.05 |

[a]Binding was determined to be the percentage of TE cells rosettes (≧3 bound thymocytes). Shown is the mean and standard error of 5 separate experiments.
[b]% Inhibition = 100 (Binding$_{control}$ − Binding exp)/Binding$_{control}$. The controls were P3 for mabs, and ELAM-Ig for CD6-Ig.

P values represent 2 tailed Student's t-test comparing binding in the presence of mabs or CD6-Ig to control binding.

Figure 1:
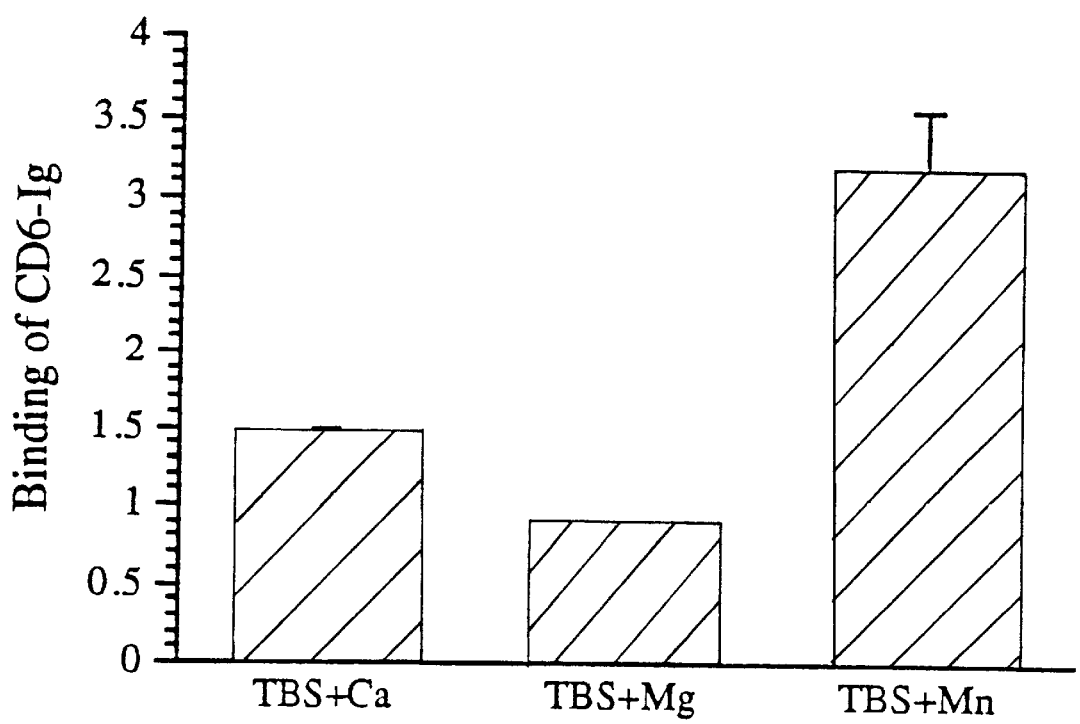
FIG. 1. Effect of divalent cations on binding of CD6-Ig (=CD6-Rg) to thymic epithelial cells (TEC). TEC were incubated with 5 μg of CD6-Ig or CD5-Ig in buffers containing 2% BSA, Tris-HCl buffered saline (TBS) and either 5 mM $CaCl_2$, 5 mM $MgCl_2$ or 5 mM $MnCl_2$, and assayed by indirect immunofluorescence and flow cytometry. Shown is the relative binding of CD6-Ig in the various buffers. Relative binding was determined as the ratio of specific binding of CD6-Ig (fluorescence of CD6-Ig-fluorescence of CD5-Ig) in sample buffer to the specific binding in TBS. Shown is a representative of three experiments (except for TBS+Mg which was performed only once). Both $CaCl_2$ and $MnCl_2$ were able to significantly enhance the binding of CD6-Ig to TEC ($p<0.1$).
Figure 2:
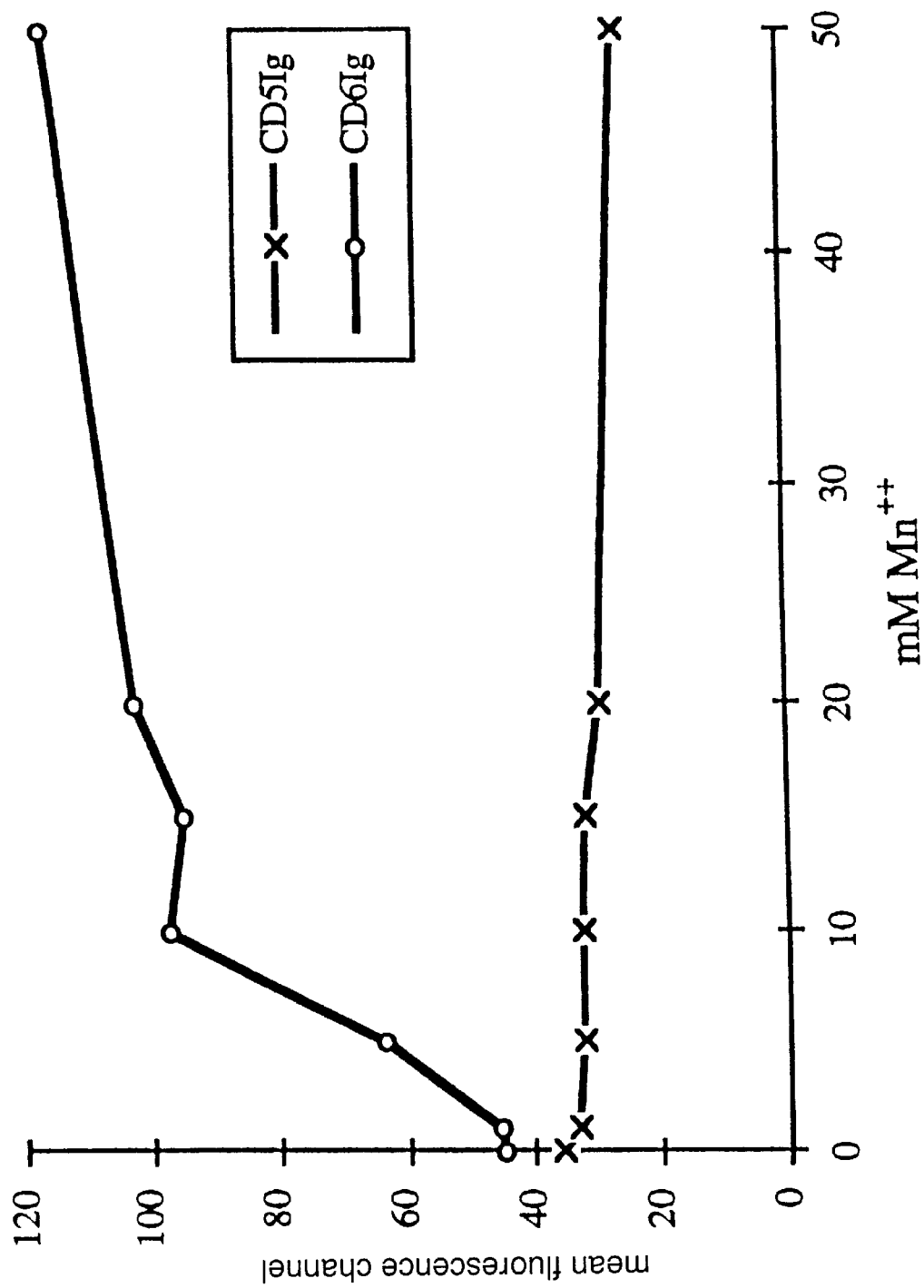
FIG. 2. CD6-Ig binding to TEC is enhanced by $Mn^{++}$. TEC were incubated with 5 μg of CD6-Ig or CD5-Ig in buffers containing 2% BSA, TBS and various concentrations of $MnCl_2$, and assayed by indirect immunofluorescence and flow cytometry. The graph shows the relative binding of CD6-Ig in buffers containing varying amounts of $MnCl_2$. Shown is a representative of three separate experiments.

Human TE cells express a ligand for CD6: To confirm that human TEC express a ligand for CD6, TEC were incubated with recombinant CD6-Ig fusion proteins and assayed for CD6-Ig binding to TEC by indirect immunofluorescence followed by flow cytometry. Neither of the negative controls (CD5-Ig and ELAM-Ig) bound to the surface of TEC while CD6-Ig did bind to TE cells (Table 2), indicating that there is a ligand for CD6 expressed on the surface of human TE cells. CD6-Ig binding to the CD6 ligand on TE cells was enhanced by divalent cations ($Ca^{++}$ and $Mn^{++}$) and partially inhibited by EDTA (FIGS. 1 and 2). The data suggest that there are at least two components to the binding of CD6-Ig to TEC—a component (or ligand) that is dependent upon divalent cations, and a component (or ligand) that is divalent cation-independent.

TABLE 2

Reactivity of fusion proteins on
human thymic epithelial cells[a]

| fusion protein | MFC[b] |
|---|---|
| IgG$_1$ | 72.9 |
| ELAM-Ig | 70.5 |
| CD5-Ig | 72.1 |
| CD6-Ig | 164.9 |

[a]Cultured TE cells were incubated with 2000 μg/ml fusion proteins. Fusion proteins were detected by indirect immunofluorescence followed by flow cytometry.
[b]Linear Mean Fluorescence Channel. Data are representative of 3 experiments.

Figure 3:
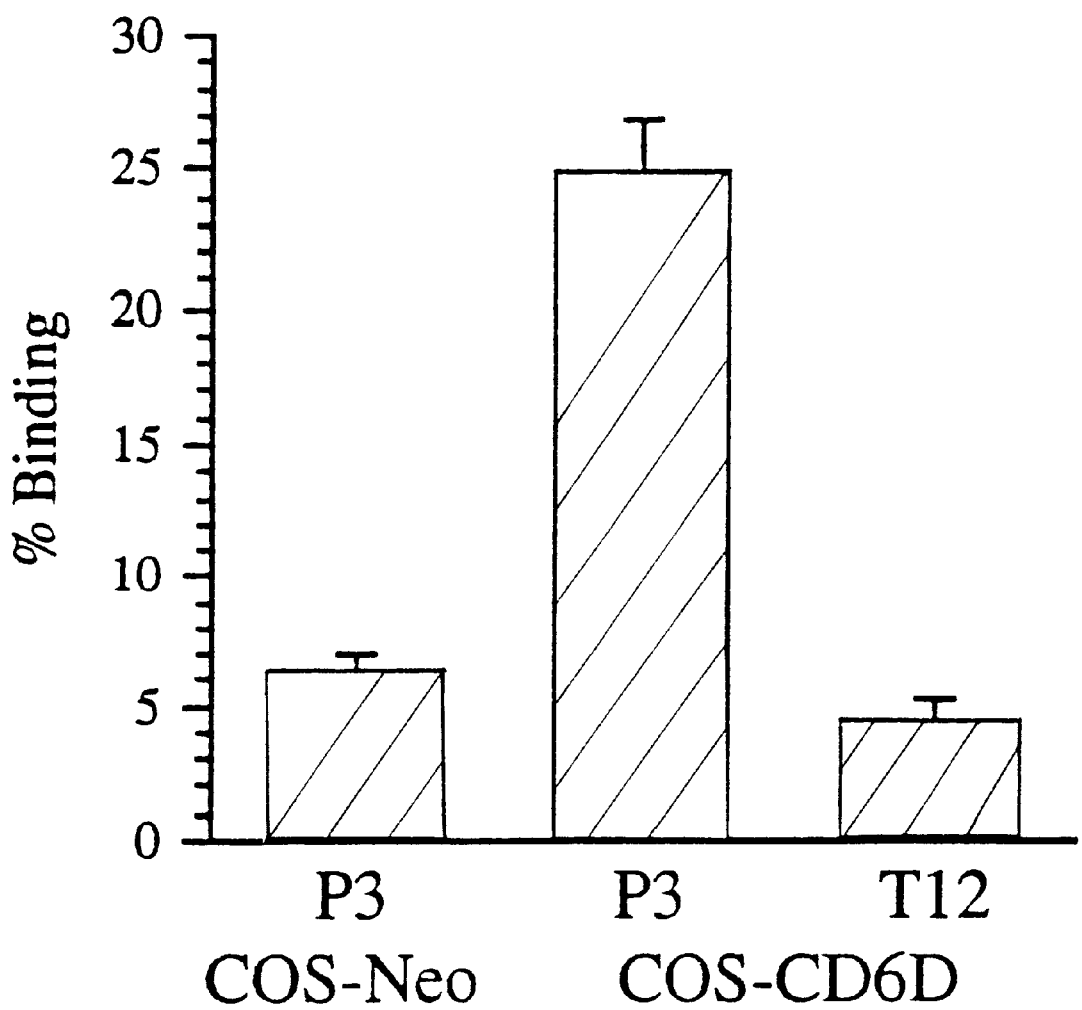
FIG. 3. Binding to TEC is enhanced by the expression of CD6 in COS cells. COS cells that express CD6 in a stable manner (COS-CD6D) or control COS cells (COS-Neo) were incubated with calcein-AM labelled TEC at a ratio of 1:5 for 60 min at 4° C. Binding was detected by using a combination of light and fluorescence microscopy. Binding was determined to be the percentage of COS cells with 3 or more bound TEC. The expression of CD6 in COS cells enhanced the binding of COS cells to TEC, and this binding was inhibited by anti-CD6 antibody.

CD6 is an adhesion molecule: The fact that T12 and CD6-Ig both partially inhibit the binding of thymocytes to TEC strongly suggested that CD6 was an adhesion molecule. The TE rosette studies, however, did not rule out the possibility that T12 and CD6-Ig inhibited TE-thymocyte binding because of steric hinderance. To determine if CD6 was indeed an adhesion molecule, a COS cell line (COS-CD6D) was made that expressed high levels of transfected CD6. COS cells without CD6 (CS-Neo) did not bind to TEC, whereas COS-CD6D cells did bind TEC (FIG. 3). Furthermore, this COS-CD6D:TE cell binding was CD6-dependent as binding was inhibited by mab to CD6 (T12).

Figure 4:
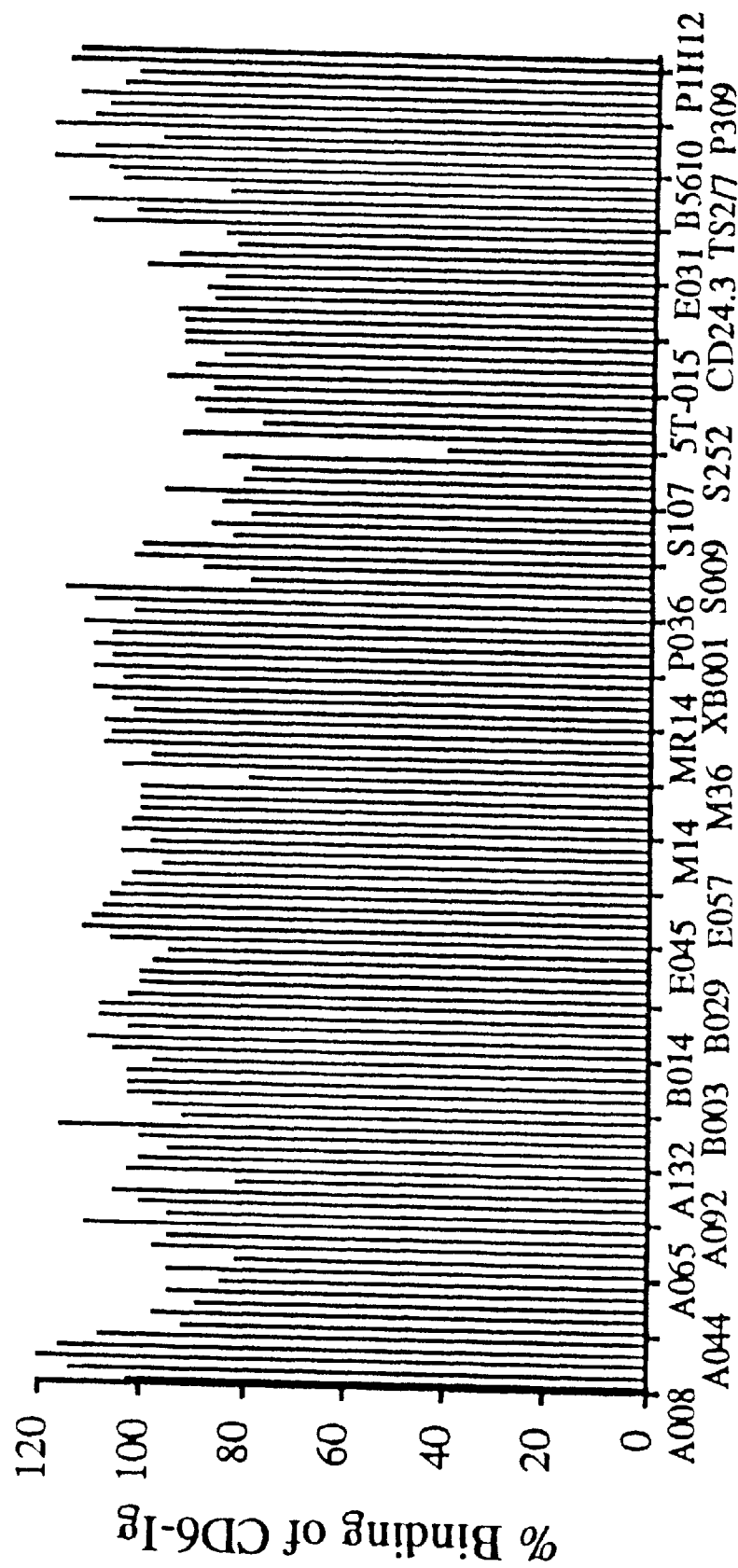
FIG. 4. Monoclonal antibody J4-81 inhibits the binding of human CD6-Ig fusion protein to human TEC. The binding panel of 470 mabs from the V International Workshop on Human Leukocyte Differentiation Antigens and a panel of anti-integrin mabs was screened for reactivity to TE cells. Of the 154 mabs that reacted with TE cells, 126 were used in assays to inhibit the binding of CD6-Ig to TE cells. The workshop mabs that reacted with TE cells and were used in this study were: A008, A014, A023-4, A036-7, A044, A047-9, A063, A065, A070, A074, A080, A090, A092, A107, A110, A113, A124, A132, A139, A141, A145, B002, B003, B005-6, B011-2, B014, B019, B025, B027-9, B031, B046, B049, B052, B055-7, B059, B068, CB10, CB22, CB27, E001, E015, E031, E045, E050, E053-4, E056-7, M01-2, M09, M14-5, M25, M32, M35-8, M43-4, MR1, MR4, MR6, MR9, MR12, MR14, XB001, NK32, P005, P012, P023, P036, P044, P098, P107-8, S009, S013, S023-4, S031, S075, S107, S188, S201, S241, S245, S252, S263, S271, S273-4, 5T-015, 5T-076, 5T-080, 5T-084, CD24.3, CD40.2, CD73.1, CD74.1 and CD77.1. Anti-integrin mabs used were: TS2/7, P1H6, 12F1, P1B5, P4G9, B5610, P3010, EA-1-6, 135-13C, P502, P309, K20, β4, P3G8, P3G2, P1H12 and TS2/16. The cells were pre-incubated with mabs at a dilution of 1:100 for 15 min at 4° C. followed by incubation with 5 μg of either CD5-Ig or CD6-Ig. Cells were washed and fusion proteins detected by reaction with fluorescein conjugated antiserum specific to the Fc portion of human IgG and flow cytometry. Specific binding was determined to be the difference in fluorescence of CD6-Ig binding and CD5-Ig binding. The binding compared to control mab (P3) is shown. There were four instances where goat anti-human IgG-Fc cross reacted with the test mab (A024, B049, 5T-084 and CD73.1). Mab J4-81 (S252) inhibited CD6-Ig binding by 56±5% (N=2).
Figure 5:
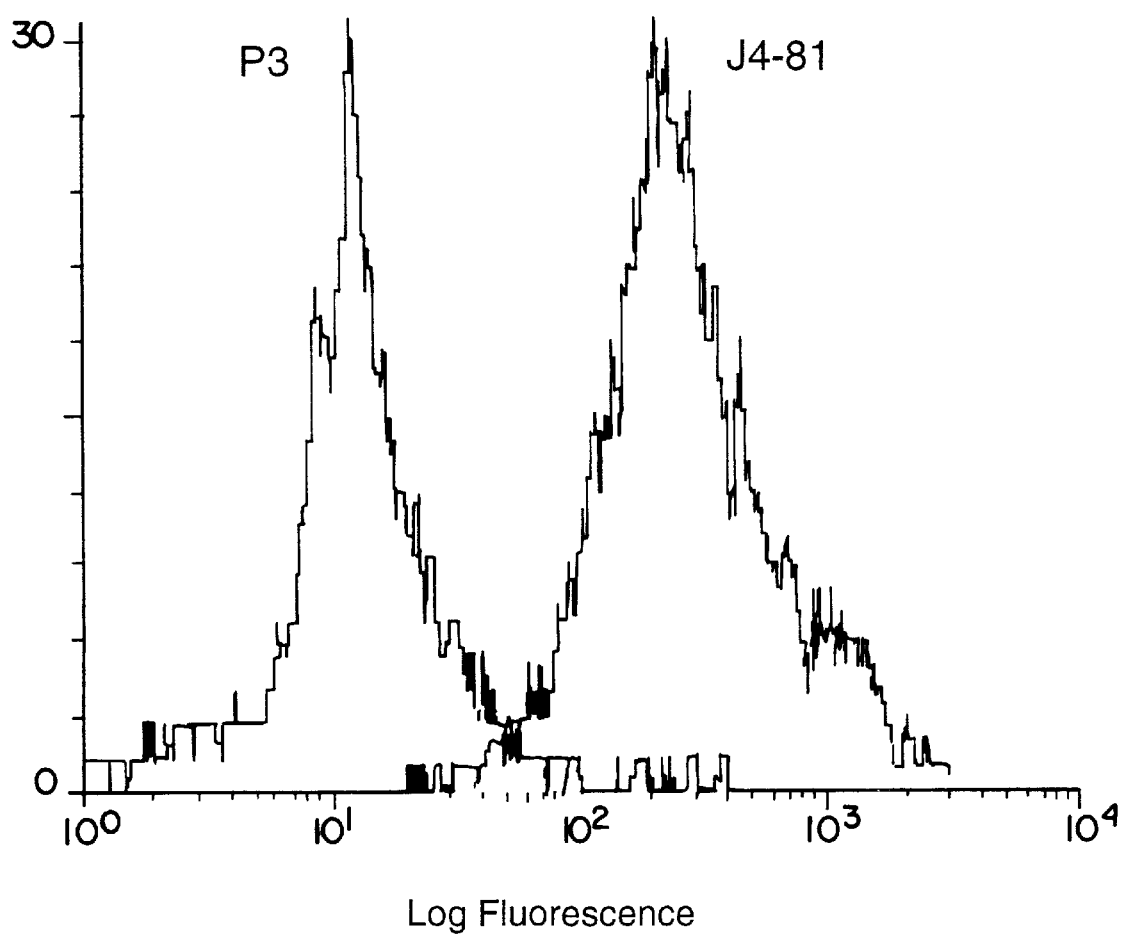
FIG. 5. Mab J4-81 reacts strongly with the surface of all cultured TEC. Cultured TEC were incubated with mab J4-81 (S252 from the Vth International Workshop on Human Leukocyte Differentiation Antigens) and control mab (P3) for 30 min at 4° C. Following a wash with PBS containing 2% BSA, bound antibodies were detected by reaction with fluorescein conjugated goat anti-mouse IgG followed by flow cytometry. Shown are the fluorescence profiles of control mab (P3) and the mab against a CD6 ligand (J4-81).
Figure 6A:
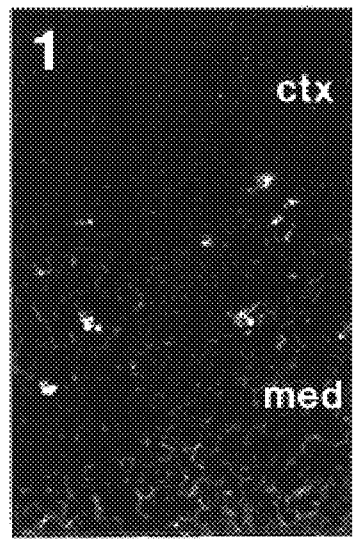
FIGS. 6A and 6B. Expression of CD6 and its ligand in postnatal human thymus. CD6 and its ligand in frozen human thymus sections (4 μm) were labelled by indirect immunofluorescence using mabs T12 and S252 (J4-81), respectively.
Figure 6B:
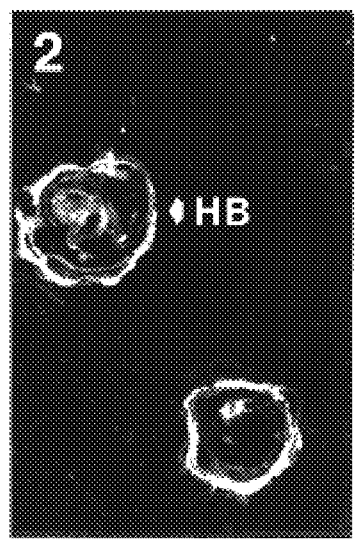

Mab J4-81 reacts with a ligand for CD6: To identify the CD6 ligand, a large panel of anti-integrin mabs and a blind panel of 479 mabs from the Vth International Workshop on Human Leukocyte Differentiation Antigens were screened for reactivity to TE cells. Of the 154 mabs that reacted with TEC, 126 mabs were used in assays to inhibit the binding of CD6-Ig to TEC. As shown in FIG. 4, only Workshop mab S252 (J4-81) was able to inhibit the binding of CD6-Ig to TEC. Mab J4-81, which was raised against B cell surface antigens, recognizes a 105 kDa protein on B cells (Pesando et al, J. Immunol. 137:3689 (1986)) and reacts strongly with the surface on all cultured TEC (FIG. 5) and with medullary TEC in frozen sections of human thymus (FIG. 6).

Figure 7:
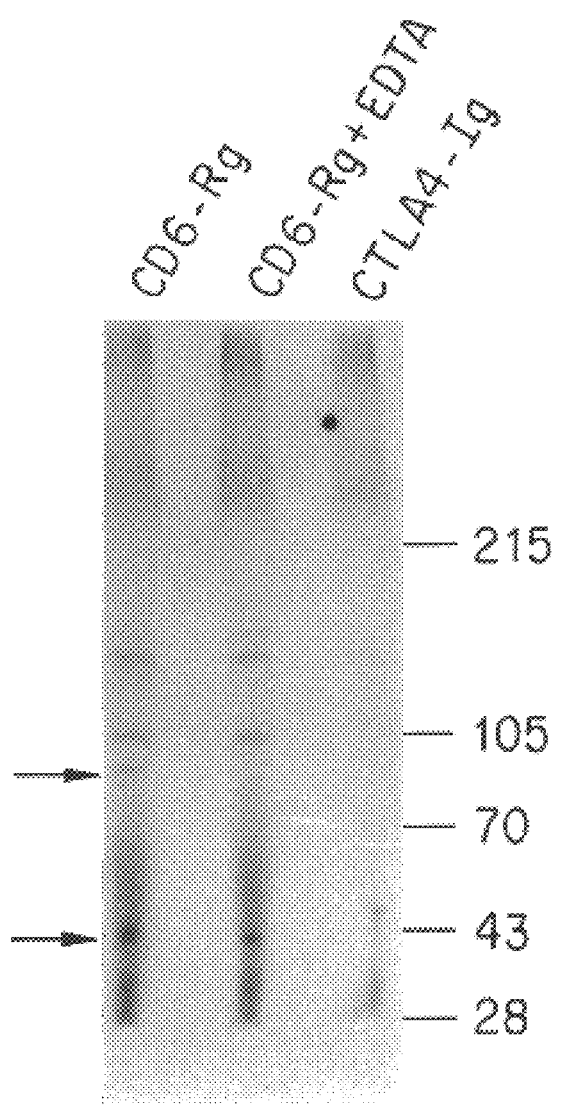
FIG. 7. Immunoprecipitation of radioactively labelled glycoproteins from metabolically labelled TEC with CD6-Ig. Cells were labelled with 6-$^3$H-glucosamine for 48 hours, lysed and lysates were immunoprecipated with CD6-Ig and with CTLA4-Ig as a control. CD6-Ig immunoprecipitation of TEC lysates was carried out with and without inclusion of 15 mM EDTA. The immunoprecipitation of a 105 kDa molecule and a 35 kDa molecule by CD6-Ig was divalent cation independent and the immunoprecipitation of an additional 90 kDa molecule by CD6-Ig was divalent cation dependent.

Immunoprecipitation of 105 kDa, 90 kDa and 35 kDa molecules from TEC with CD6-Ig: In the absence of EDTA, CD6-Ig fusion protein immunoprecipitated protein species with molecular weights of 105, 90 and 35 kDa (FIG. 7, lane 1) (note approximately 150 kDa band). In the presence of EDTA, CD6-Ig immunoprecipitated only the 105 and 35 kDa species (FIG. 7, lane 2) (note approximately 150 kDa band). In lane 3, in the absence of EDTA, the control fusion protein, CTLA4-Ig, did not immunoprecipitate the 105, 90 or 35 kDa protein species.

Mab J4-81 inhibits the binding of TE cells to COS-CD6D cells: A third approach has been used to define that the 105/35 kDa protein molecules detected by mab J4-81 is a ligand for CD6. As shown above, COS-CD6D:TEC binding is CD6-specific. To further demonstrate that CD6 and the 105/35 kDa molecules recognized by J4-81 form an adhesion molecule pair, COS-CD6D:TEC binding with mab J4-81 was inhibited (Table 3).

TABLE 3

Effect of monoclonal antibodies COS-CD6D:TEC binding

| mab | % Binding[a] | % Inhibition[b] | |
|---|---|---|---|
| P3 | 25.0 ± 1.8 | 0 | |
| T12 (anti-CD6) | 4.5 ± 0.7 | 82.7 ± 2.1 | p < 0.0007 |
| S252 (J4-81) | 8.7 ± 0.7 | 65.3 ± 1.8 | p < 0.0008 |

[a]Binding was determined to be the percentage of COS cells rosettes (≧3 bound TEC). Shown is the mean and standard error of 3 separate experiments.
[b]% Inhibition = 100 (Binding$_{P3}$ − Binding$_{exp}$)/Binding$_{P3}$.

P values represent 2 tailed Student's t-test comparing inhibition in the presence of T12 or J4-81 inhibition in the presence of P3.

Reactivity of J4-81 mab with human tissue in indirect IF assay: Mab J4-81 reacted with TEC, epidermal keratinocytes, fibroblasts, acinar cells and islet cells of pancreas, gut epithelium, monocytes (10%) and activated PB T cells (21). B cells are also positive for J4-81 (Pesando et al, J. Immunol. 137:3689 (1986)). Taken together, these data demonstrate that the CD6-CD6 ligand system is involved in TEC-thymocyte interactions, that CD6 is an adhesion molecule and that 105/35 kDa proteins detected by mab J4-81 comprise a ligand for CD6. Moreover, that the CD6-divalent cation-independent ligand defined by mab J4-81 is expressed on a wide variety of immune and epithelial cell types suggests that the CD6/CD6 ligand system is important in immune cell interactions with other immune cells and with a wide variety of epithelial microenvironments.

EXAMPLE II

Experimental details:

Cell lines, fusion protein, and antibodies. The colon carcinoma-derived cell line H3719 and the melanoma-derived cell line H3606 were from Drs. K. E. and I. Hellström (Bristol-Myers Squibb, Seattle, Wash.). The human breast epithelial cell line HBL-100, the EBV-transformed human B cell line LCL, the human lung fibroblast IMR90, the adult T cell leukemia Jurkat, the cutaneous T cell lymphoma HUT78, the human peripheral blood acute leukocytic leukemia derived cell line HPB-All, the human T cell lymphoma H9, the human Burkitt lymphoma Raji, the fibroblast cell line GM0833, the B cell lymphoblastoma Peer, the T cell leukemia JM, and the B cell lymphoblastoma LTR228 were used and obtained primarily from the American Type Culture Collection (Rockville, Md.). The CD5-Rg (Aruffo et al, Proc. Natl. Acad. Sci. USA 89:10242 (1992)), ELAM1-Rg (Walz et al, Science 250:1132 (1990)), and CTLA4-Ig (Linsley et al, J. Exp. Med. 174:561 (1991)) have been previously described. The anti-CD6 mAb G3-6 (IgG) was from Dr. J. Ledbetter (Bristol-Myers Squib, Seattle, Wash.) (Ledbetter et al, Proc. Natl. Acad. Sci. USA 84:1384 (1987)); the anti-CD6 mAb MBG6 (IgM) was from Dr. A. McMichael (Oxford University, Oxford, U.K.) (Bastin et al, J. Clin. Exp. Immunol. 46:597 (1981)); the anti-CD6 mAb 2H1 was from Dr. C. Morimoto (Dana-Farber Cancer Institute, Boston, Mass.) (Morimoto et al, J. Immunol. 140:2165 (1988)); the anti-CD6 mAb T12 has been previously described (Reinherz et al, Cell 30:735 (1982)). The DNA restriction enzymes and the DNA linkers were obtained from New England Biolabs (Beverly, Mass.); RPMI, HBSS, FBS, and prestained molecular weight markers were obtained from GIBCO-BRL (Gaithersburg, Md.). Human epidermal keratinocytes (EK) were cultured from neonatal foreskins. Foreskins were incubated at 4° C. overnight in 2.5 mg/ml trypsin type III (Sigma, St. Louis, Mo.) in HBSS (GIBCO-BRL), the epidermis was removed, teased into single-cell suspension, seeded onto mitomycin C-treated 3T3 fibroblast feeder layers, and cultured as described (Hashimoto et al, J. Exp. Med. 145:259 (1983)).

Preparation of CD6-Rg. The plasmid encoding the CD6-Rg containing a full-length cDNA clone encoding CD6 (Aruffo et al, J. Exp. Med. 174:949 (1991)) was digested with the restriction enzyme EspI, treated with the Klenow fragment of DNA polymerase I, and ligated to BamHI linkers (New England Biolabs, Beverly, Mass.). The vector was then digested with the restriction enzymes NdeI and BamHI. The NdeI/BamHI DNA fragment containing the extracellular domain of CD6 was subcloned into a plasmid containing a cDNA fragment encoding the constant domains (hinge, CH2, and CH3) of human $IgG_1$. The CD6-Rg protein was prepared by transient expression in COS cells as previously described (Aruffo et al, Cell 61(7):1303 (1990)) and purified from the supernatant of COS cell transfectants by absorption to, and elution from, a protein A column (Repligen, Cambridge, Mass.).

CD-6 Rg cell binding studies. Typically, $5\times10^7$ cells/ml in HBSS/2% FBS/20 mM Hepes (wash/stain buffer) were incubated with 50 μg/ml of fusion protein. Adherent cells were detached from dishes with 0.5 mM EDTA in PBS (PBS/EDTA) and washed once, while nonadherent cells were washed once before incubation with the fusion protein for 1 hr on ice. The cells were subsequently washed three times and incubated with FITC-goat anti-human IgG (10 μg/ml, Tago, Burlingame, Calif.) for 1 hr on ice. The cells were washed three times, fixed with 1% paraformaldehyde in PBS, and analyzed by flow cytometry (Epics V, Coulter, Hialeah, Fla.).

This staining procedure was used to examine if the binding of CD6-Rg to HBL-100 cells was saturable. In those experiments the CD6-Rg and control fusion protein were used at the following concentrations: 10, 20, 30, 40, 50, 100, and 200 μg/ml. To investigate the sensitivity of CD6-Rg ligand(s) to trypsin, HBL-100 cells ($5\times10^7$) were treated with 0.05% trypsin/0.5 mM EDTA for 30 min at 37° C., washed three times with wash/stain buffer, incubated with CD6-Rg and analyzed by flow cytometry as described above. To examine the divalent cation requirement for CD6-Rg binding, CD6-Rg was incubated with HBL-100 cells in the presence of 15 mM EDTA, or, alternatively, the EDTA was added to HBL-100 cells which had been previously incubated with CD6-Rg and washed. For anti-CD6 blocking experiments CD6-Rg (50 μg/ml) was incubated with a 1:50, 1:100 , and 1:200 dilution of the 1 mg/ml anti-CD6 mAb G3-6 (IgG) or ascites containing the MBG6 mAb (IgM, from A. J. McMichael) or an isotype matched (IgM) antibody. To examine the cytokine-induced modulation of CD6-Rg binding to HBL-100 cells, cells were incubated with IL-1β, TNF-α (Genzyme, Boston, Mass.), and IFN-γ (Upstate Biotechnology Inc., Lack Placid, N.Y.) (10 ng/ml) individually, in pairwise combinations, or all together, for 48 hr at 37° C., 5% $CO_2$ prior to CD6-Rg binding studies.

Immunoprecipitation studies. For immunoprecipitation studies, cells were incubated with 120 μCi/ml of [6-$^3$H] glucosamine (NEN Dupont, Boston, Mass.) in glucose-free RPMI containing 10% normal RPMI and 10% dialyzed FBS for 48 hr at 37° C. and 5% $CO_2$. The cells were lifted from the culture dish with PBS/EDTA, washed in HBSS, and lysed in 20 mM Tris, pH 7.5, containing leupeptin, PMSF, and pepstatin (1 μg/ml, Boehringer Manheim, Indianapolis, Ind.), 0.05% sodium cholate, 2% NP-40 (lysis buffer). The lysates were spun to remove nuclei and precleared by incubating two times with 50 μg/ml of human IgG1 (Sigma) and 50 μl of protein A-Sepharose slurry (Repligen) for 30 min at 4° C. Cell lysates were then incubated with 50 μg/ml of CD6-Rg or CTLA4-Ig or 2 μg/ml of an anti-EGF receptor antibody (Oncogen Science, Uniondale, N.Y.) in the presence of either 2 mM $Ca^{2+}$ and $Mg^{2+}$ or 15 mM EDTA with 50 μl of protein A-Sepharose (Repligen), for 2–4 hr at 4° C. The protein A-Sepharose beads were then washed three times with lysis buffer. The immunoprecipitated proteins were analyzed by SDS-PAGE (8–10.5% gradient gel) followed by autoradiography.

Immunohistology. Murine (Balb/c) lymphoid and non-lymphoid tissues were removed and frozen in liquid nitrogen. Six-micrometer cryostat tissue sections were prepared, mounted on glass slides, and fixed with ice-cold acetone. The fixed sections were stained using 50 μg/ml of CD6-Rg or human IgG1 (Sigma) in a solution of PBS containing 1 mM $Ca^{2+}$ and $Mg^{2+}$, 10% BSA, and 10% normal goat serum (NGS) (staining buffer) for 1 hr at room temperature. The slides were washed three times in staining buffer and incubated with a 10 μg/ml of fluorescein-conjugated, affinity-purified goat anti-human IgG antibody (Tago) for 1 hr at room temperature. After washing three times with staining buffer, the slides were examined by fluorescence microscopy.

Results:

CD6 receptor globulin, CD6-Rg. The CD6-Rg fusion gene was constructed by fusing a cDNA fragment encoding the 400-amino acid extracellular domain of CD6 (Aruffo et al, J. Exp. Med. 174:949 (1991)), including its amino acid terminal signal sequence, onto a cDNA fragment encoding the hinge (H), CH2, and CH3 domains of human $IgG_1$ and subcloned into the mammalian expression vector CDM7B⁻ (Aruffo et al, Cell 61(7) :1303 (1990)) as described above. The cDNA fragment encoding the IgG constant domain contains three point mutations. These amino acid substitutions result in the impaired binding of IgG Fc domains to FcRI, II, and III.

The CD6-Rg protein used in this study was obtained by transient expression in COS cells and purified by absorption to, and elution from, a protein A column (Aruffo et al, Cell 61(7):1303 (1990)). CD6-Rg is expressed as a covlanet homodimer and is recognized by all anti-CD6 mAb tested in an ELISA assay (T12, 2H1, MBG6, and G3-6). The previously described CD5-Rg (Aruffo et al, Proc. Natl. Acad. Sci. USA 89:10242 (1992)), ELAM1-Rg (Walz et al, Science 250:1132 (1990)), and CTLA4-Ig (Linsley et al, J. Exp. Med. 174:561 (1991)) fusion proteins and/or human IgG1 were used as isotype matched controls in all the binding and immunoprecipitation studies.

Figure 8:
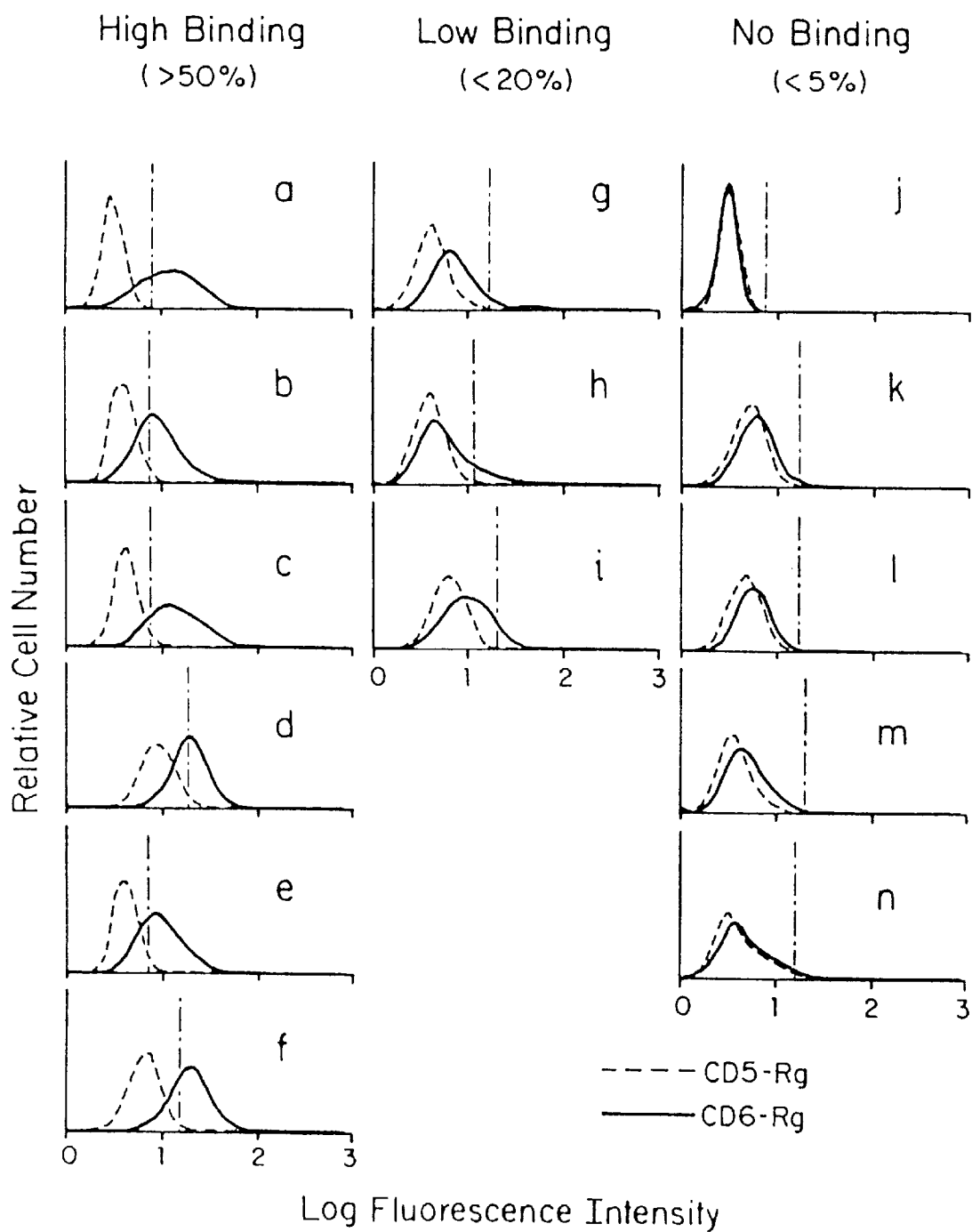
FIG. 8. CD6-Rg (=CD6-Ig) binds to a number of human-derived cell lines. Binding of CD6-Rg (solid line) and CD5-Rg (dashed line) to a number of human cell lines was examined by flow cytometry. The cell lines were grouped into three categories based on their ability to bind CD6-Rg high binding, low binding, and no binding. The percentage binding used to group cells into these three categories is based on the number of cells whose fluorescence intensity is greater than that of cells stained with the isotype matched CD5-Rg fusion protein (vertical dash-dot line). The human cell lines examined were: (a) HBL-100, (b) H3719, (c) H3606, (d) LCL8664, (e) GM0833, (f) IMR90, (g) Jurkat, (h) Peer, (i) HUT78, (j) HPB-ALL, (k) JM, (l) H9, (m) LTR228, and (n) Raji. A total of $10^4$ cells were analyzed in each experiment.

CD6-Rg binding to human and murine cells. The binding of CD6-Rg to a number of human and murine cell lines was examined by indirect immunofluorescence using flow cytometry. CD6-Rg bound to a subset of the cell lines examined (FIG. 8). Among the cell lines which showed the brightest fluorescence intensity following CD6-Rg staining were the human breast epithelial-derived cell line HBL-100, the human colon carcinoma-derived cell line H3719, the melanoma-derived cell line H3606, the EBV-transformed human B cell line LCL, and the human fibroblast cell lines GM0833 and IMR90. Among the cell lines exhibiting intermediate fluorescence intensity following CD6-Rg binding were the lymphoid cell lines Jurkat, Peer, and HUT78. A number of other lymphoid cell lines including HPBALL, JM, H9, LTR228, and Raji exhibited no binding to CD6-Rg. None of these cell lines exhibited significant binding to the control fusion protein CD5-Rg. The binding to HBL-100 cell line was further characterized.

Figure 10:
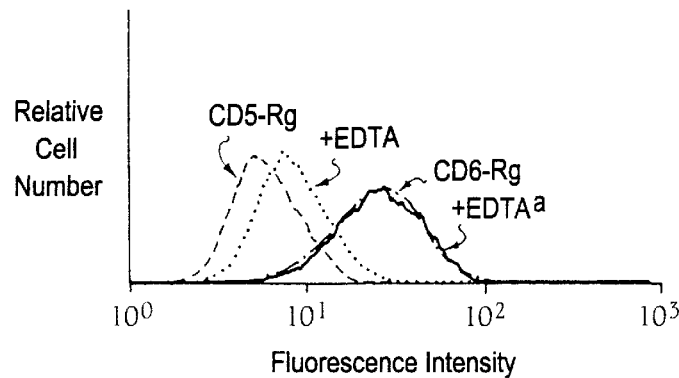
FIG. 10. CD6-Rg binding is divalent cation dependent. The binding of CD6-Rg to HBL-100 cells in the presence of EDTA (+EDTA, dotted line) was compared to the binding of CD6-Rg (dash-dot line) and CD5-Rg (dashed line) by flow cytometry. The effect of EDTA on CD6-Rg binding to HBL-100 cells was also examined after the CD6-Rg/HBL-100 complexes were allowed to form (+EDTA, solid line). A total of $10^4$ cells were examined in each experiment.
Figure 9A:
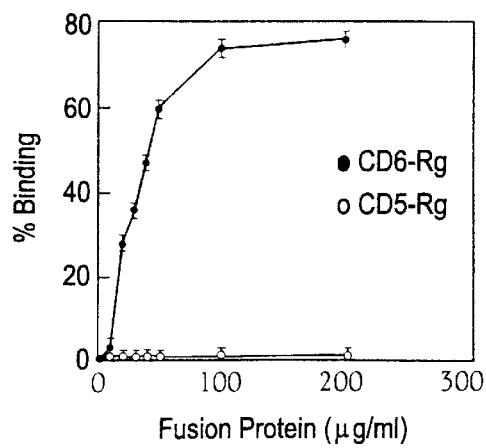
FIGS. 9A and 9B. CD6-Rg binding is saturable and trypsin sensitive.

Binding of increasing concentrations of CD6-Rg to the HBL-100 cell line showed that the interaction of CD6-Rg with this cell line was dose dependent and saturable (100 µg/ml, FIG. 9A). Treating these cells with trypsin abolished CD6-Rg binding (FIG. 9B), while neuraminidase or N-glycanase treatment only slightly decreased CD6-Rg binding. The binding of CD6-Rg to HBL-100 was in part EDTA sensitive when the chelator was added before the CD6-Rg/HBL-100 binding, but not after (FIG. 10). In addition CD6-Rg bound very weakly to this cell line in PBS; however, addition of either $Ca^{2+}$ or $Mg^{2+}$ (2 mM final concentration) resulted in strong CD6-Rg binding to HBL-100 cells.

Figure 11:
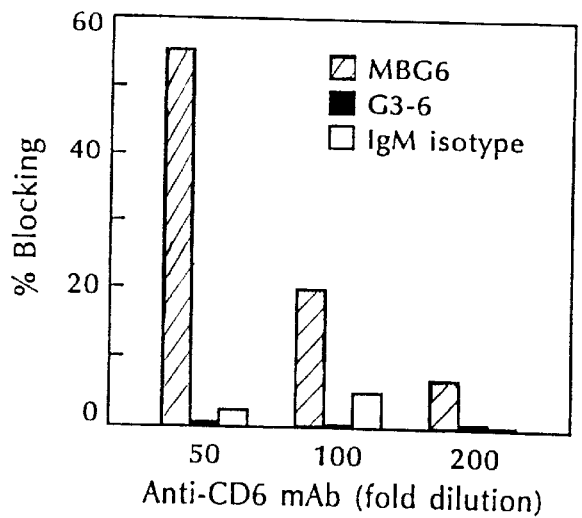
FIG. 11. CD6-Rg binding is blocked by an anti-CD6 mAb. The ability of two different anti-CD6 mAb (MBG6 and G3-6) and an irrelevant IgM mAb to block the binding of CD6-Rg to HBL-100 cells was examined by flow cytometry. In each case serial dilution of the antibodies was tested.

The ability of the anti-CD6 mAb MGB6 and G3-6 to block the binding of CD6-Rg to HBL-100 cells was examined. The MGB6 mAb was able to block CD6-Rg binding to HBL-100 in a concentration-dependent manner (FIG. 11), while the G3-6 mAb was unable to block CD6-Rg binding to HBL-100 cells at concentrations as high as 0.02 mg/ml (FIG. 11).

Figure 12A:
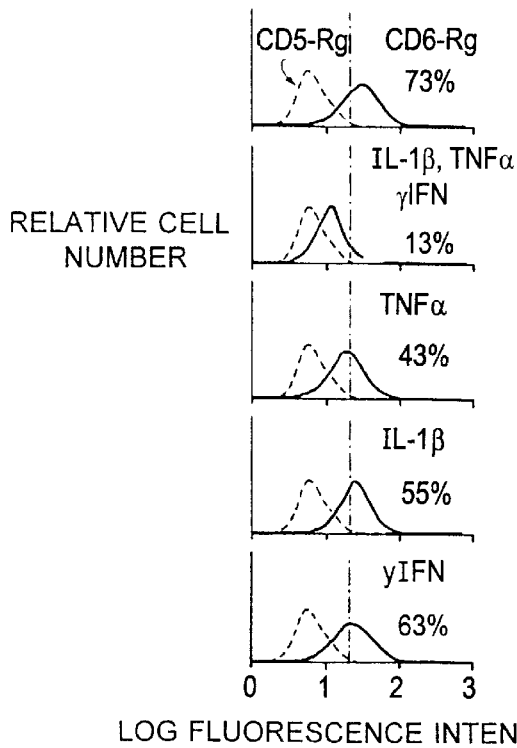
FIGS. 12A and 12B. CD6-Rg binding is modulated by cytokines. The biding of CD6-Rg (solid line) and CD5-Rg (dashed line) to untreated HBL-100 cells or HBL-100 cells treated with the indicated cytokines was examined by flow cytometry. The percentage of HBL-100 cells whose fluorescence intensity is to the right of an arbitrary marker (dash-dot line) following CD6-Rg binding is noted in each panel. The data shown in columns (FIG. 12A) and (FIG. 12B) represent two different experiments.
Figure 12B:
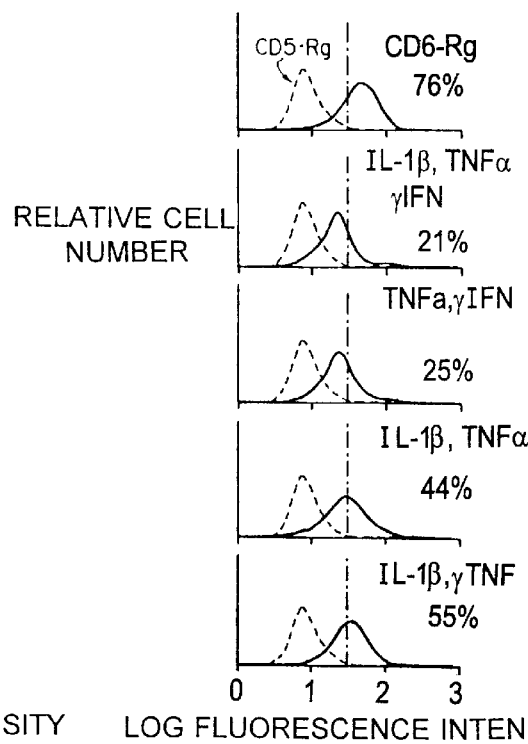

Effects of cytokines on CD6-Rg binding. Cytokines regulate the expression of a number of cell surface proteins. The effect of cytokines on the expression of the CD6-binding protein(s) expressed by HBL-100 cells was examined. Treatment of the cells with a mixture of IL-1β, TNFα, and IFN-γ resulted in the downregulation of CD6 ligand(s) expression (FIG. 12). Treatment with each of the cytokines alone or with pairwise combinations of the cytokines showed that a mixture of TNFα and IFN-γ was predominantly responsible for the downregulation of CD6 ligand(s) expression by these cells.

Figure 13:
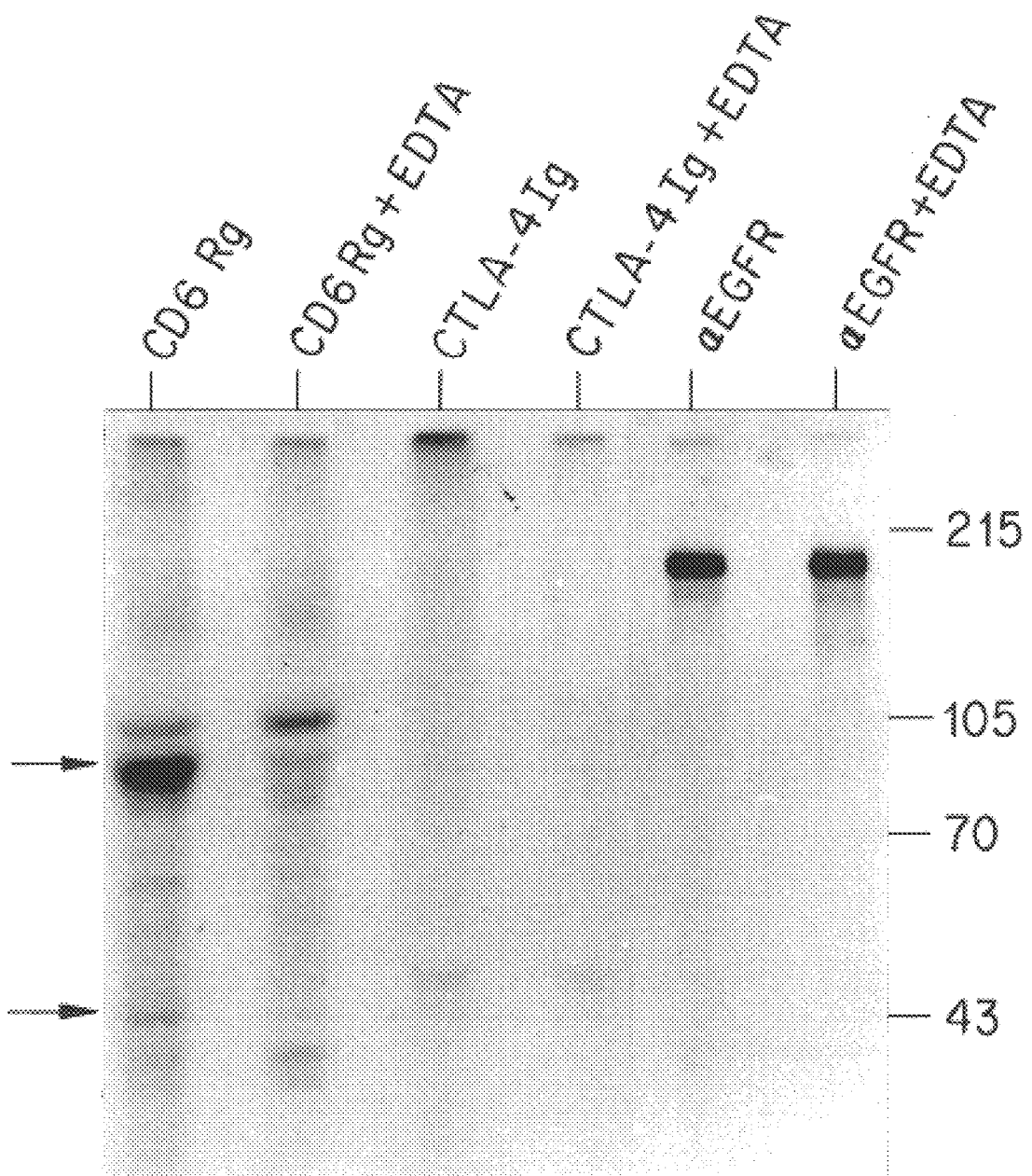
FIG. 13. Immunoprecipitation of CD6-Rg binding protein (s). HBL-100 cells were radiolabeled with [$^3$H]glucosamine. Protein(s) reactive with either CD6-Rg CTLA4-Ig, or an anti-EGF receptor mAb were immunoprecipitated from cell lysates in the absence or presence of EDTA and analyzed by SDS-PAGE. The arrows point to the two radiolabeled polypeptides which bound to CD6-Rg in the absence of EDTA. Molecular masses are given in kDa.

Immunoprecipitation of a CD6 ligand. The CD6-Rg fusion protein was used to immunoprecipitate the CD6 ligand(s) expressed by HBL-100 cells. Multiple attempts to immunoprecipitate the CD6 ligand(s) following 125I cell surface labeling or [$^{35}$S] methionine/cysteine metabolic labeling from both cell lines were unsuccessful. In contrast, [$^3$H]glucosamine labeled surface glycoproteins of ~90 and ~40 kDa were immunoprecipitated from HBL-100 cell lysates with CD6-Rg (FIG. 13). It is unclear if the ~40-kDa species is a unique protein or a degradation product of the ~90-kDa protein. Similarly, CD6-Rg was able to immunoprecipitate proteins of ~90 and ~40 kDa from [$^3$H] glucosamine-labeled H3606, a melanoma-derived cell line. CD6-Rg was unable to immunoprecipitate these proteins if EDTA was present in the cell lysate.

Figure 9B:
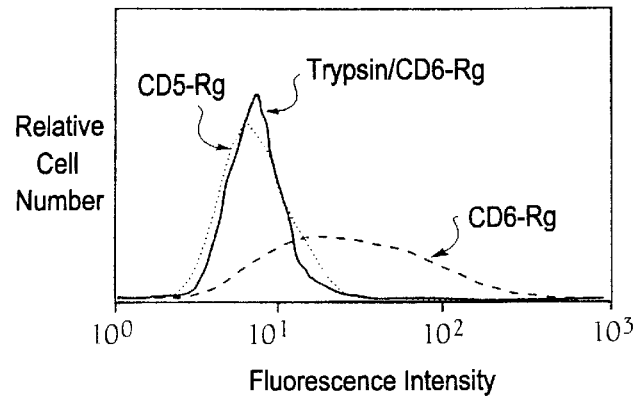

In addition, CD6-Rg but not CTLA4-Ig immunoprecipitated a polypeptide with a molecular mass of ~100 kDa from radiolabeled HBL-100 cell lysates in both the presence and the absence of EDTA (FIG. 13). This observation is consistent with cell binding studies which showed that CD6-Rg binding to HBL-100 cells was not completely blocked by EDTA (FIG. 10) but was completely abolished by pretreating the HBL-100 cells with trypsin (FIG. 9B). This ~100-kDa polypeptide was also immunoprecipitated from the H3606 lysates by the CD6-Rg fusion protein.

Figure 14A:
FIGS. 14A–14F. CD6-Rg binds to cells in lymphoid organs.
Figure 14B:
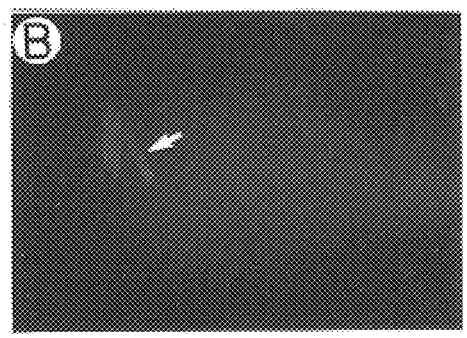
Figure 14C:
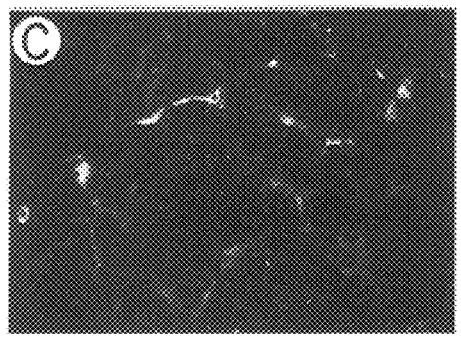
Figure 14D:
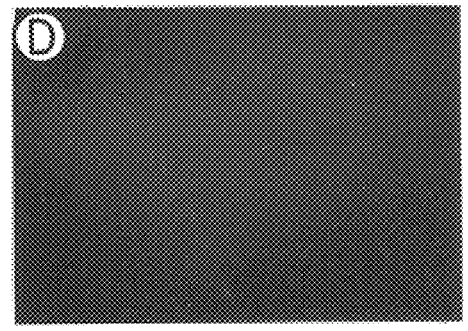
Figure 14E:
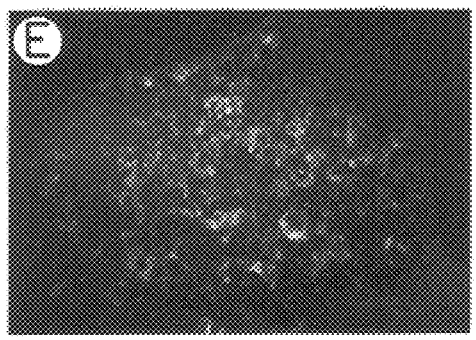
Figure 14F:
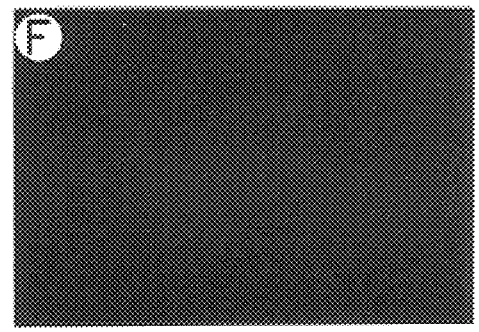

CD6-Rg Immunohistochemistry. To identify tissues which expressed high levels of CD6 ligand(s) a panel of tissue sections obtained from murine brain, skin, liver, kidney, heart, spleen, lymph node, thymus, and small intestine were examined for CD6-Rg binding. Reactivity was observed in the skin, lymph node, and thymus tissue sections (FIG. 14). In the skin bright punctate staining of the dermis as well as staining of hair follicles was observed (FIG. 14A); however, human $IgG_1$ also reacted with the hair follicle, suggesting that this interaction was not mediated by the CD6 portion of the molecule. In the thymus the predominant reactivity was observed in the cortex (FIG. 14C) while in the lymph node bright staining was seen along the intermediate sinus (FIG. 14E).

Figure 15:
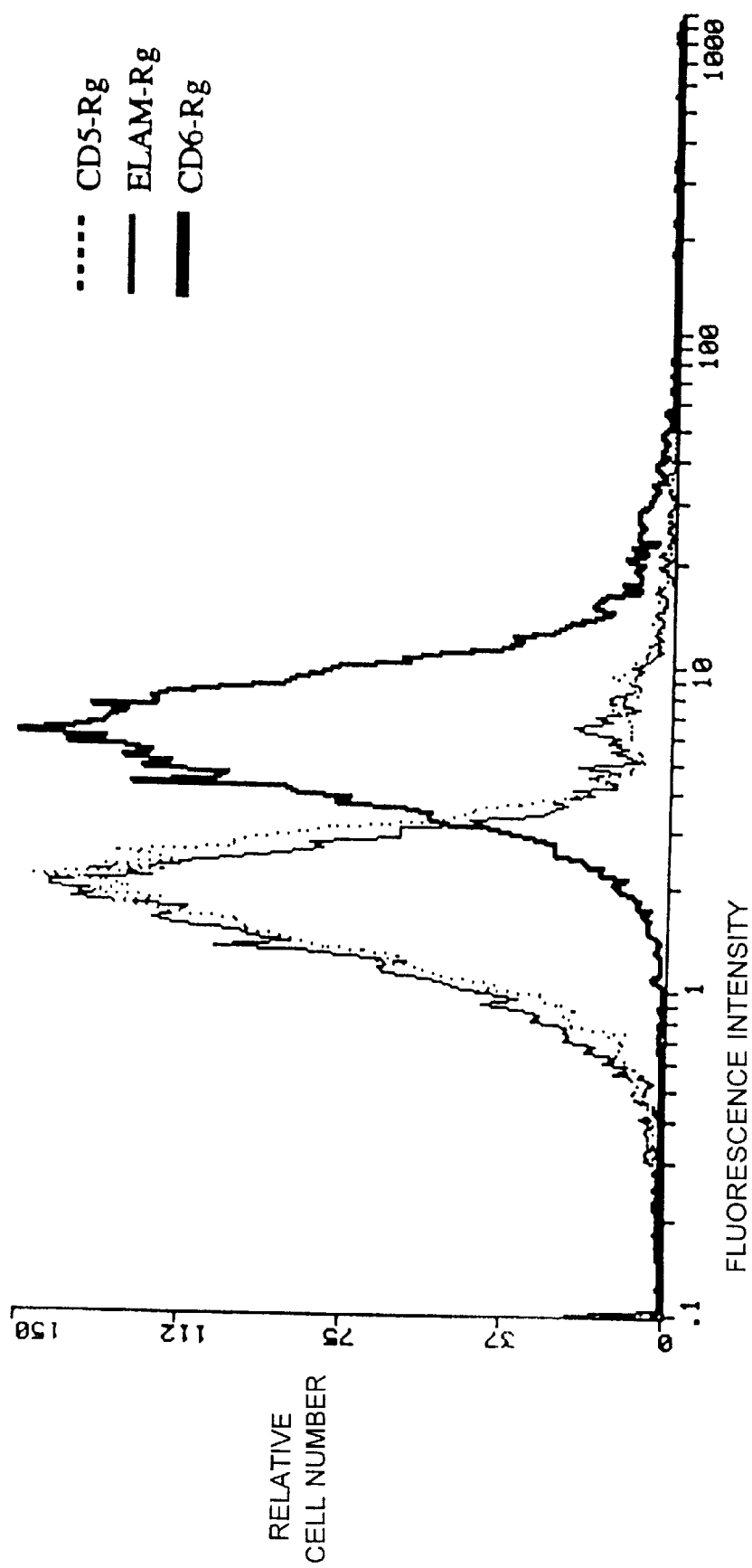
FIG. 15. Human epidermal keratinocytes express a surface ligand(s) for CD6. Shown are the reactivities of cultured epidermal keratinocytes with CD6-Rg, CD5-Rg, or ELAM1-Rg. Cells were incubated with 5 $\mu$g of fusion protein in PBS containing 2% BSA and washed. The fusion proteins were labeled with fluorescein conjugated goat antiserum to human IgG and assayed by flow cytometry.

Based on these observations, the binding of CD6-Rg to the murine thymic epithelial-derived cell line Z210 and to cultured human epidermal keratinocytes (EK) was examined. It was found that CD6-Rg bound to both Z210 and EK cells (FIG. 15). Binding to Z210 cells was trypsin sensitive, divalent cation-dependent, and modulated by cytokines in a similar manner to that observed with HBL-100 cells. The control fusion protein CD5-Rg did not bind to Z210 or EK cells (FIG. 15).

EXAMPLE III

Experimental details:

Cells and culture conditions. TE cells and thymic fibroblasts (TF) were cultured by an explant technique as described (Singer et al, Human Immunol. 13:161 (1985); Singer et al, J. Invest. Dermatol. 92:166, (1989)). Human thymus tissue was obtained from the Department of Pathology, Duke University Medical Center, as discarded tissue from children undergoing corrective cardiovascular surgery, and thymocytes prepared as described (Denninget al, J. Immunol. 139:2573 (1989)). COS-M6 cells (ATCC, Rockville, Md.) and HBL-100 cells (ATCC) were grown in DMEM containing 10% FCS, 1 mM sodium pyruvate, 0.025 µg/ml amphotericin B, 100 U/ml penicillin and 100 µg/ml streptomycin.

Monoclonal antibodies. Antibodies used in this study were: P3X63/Ag8 (control mAb; ATCC), 35.1 (anti-CD2; from J. Hansen, Seattle, Wash.), T12 (anti-CD6; from E. Reinherz, Boston, Mass.), Na1/34 (anti-CD1a; from A. McMichael, Oxford, England), A3D8 (anti-CD44; (Telen et al, J. Clin. Invest. 71:1878 (1983)), J4-81 and J3-119 (Pesando et al, J. Immunol. 137:3689 (1986)), phycoerythrin conjugated anti-CD4 (CD4-PE; Dako, Carpinteria, Calif.) cychrome conjugated anti-CD8 (CD8-Cy; Pharmingen, San Diego, Calif.), and the blind panel of 479 mAbs from the 5th International Workshop on Human Leukocyte Differentiation Antigens (Shaw, Concepts of cross-lineage (blind panel) analysis of expression of differentiation antigens. In: Leukocyte Typing, Schlossman et al, eds, Oxford University Press, Oxford (1994)).

Detection of cell surface antigens. Unfixed, cultured TE cells, TF, COS cells or HBL-100 cells were suspended in either PBS, TBS (0.9 M NaCl, 50 mM Tris-HCl pH 7.3; with or without 5 mM $CaCl_2$, 5 mM $MgCl_2$ or 5 mM $MnCl_2$) or DMEM (with or without 10 mM EDTA) containing 2% BSA and 0.1% $NaN_3$. Cells were incubated with CD6-Rg (Wee et al, Cell. Immunol. (1994)) or with CD5-Rg (Arrufo et al, Proc. Natl. Acad. Sci. USA 89:10242 (1992)), ELAM-Rg (Walz et al, Science 250:1132 (1990)), CTLA4-Rg recombinant fusion protein (Linsley et al, J. Exp. Med. 174:561 (1991)), or human IgG (Sigma, St. Louis, Mo.) as controls (100 µg/ml) for 30 min at 4° C. and washed with PBS containing 2% BSA and 0.1% $NaN_3$. Fluorescein conjugated goat anti-human $IgG_1$ (Kirkegaard & Perry Laboratories, Inc., Gaithersburg, Md.) was used as a secondary reagent. Cells were analyzed on either a Prifile II flow cytometer (Coulter Corp., Hialeah, Fla.) or a FACStar$^{Plus}$ flow cytometer (Becton-Dickinson, Inc., Mountain View, Calif.) and data was processed using the software program PC-Lysys. To determine trypsin sensitivity of fusion protein interactions, cells were incubated with 0.2% trypsin in PBS containing 1 mM EDTA for 30 min at 37° C. and washed extensively prior to reactivity with fusion proteins. Three color immunofluorescence studies were performed.

TE-thymocyte rosette binding assay. TE-thymocyte rosette binding assays were performed as described (Singer et al, Proc. Natl. Acad. Sci. USA 83:6588 (1986)). Thymocytes were separated into CD1$^+$ (immature, CD6$^{lo}$) or CD1$^-$ (mature, CD6$^{hi}$) subpopulations by indirect immunofluorescent staining with NaI/34 and goat anti-mouse IgG followed by fluorescence activated cell sorting using a FACStar$^{Plus}$ fluorescence activated cell sorter. Thymocyte subpopulations were >95% pure on reanalysis of sorted cells. Mabs used in assays of TE-thymocyte binding were used at or in excess of saturating binding titers.

COS cell transfection and binding studies. Stable lines of CD6-expressing COS cells were constructed by co-transfection of plasmid CD6-15 containing the CD6 gene under the control of a CMV promoter (Aruffo et al, J. Exp. Med. 174:949 (1991)) and the pSVneo plasmid containing the bacterial neomycin resistance gene driven by an SV40 promoter as described (Liao et al, J. Immunol. 151:6490, (1993)). COS cells expressing CD6 were identified in indirect immunofluorescence assays using mAb T12. CD6+ and CD6− cells were cloned using a Becton-Dickinson FACStar$^{Plus}$ fluorescence activated cell sorter.

CD6-expressing COS cells (COS-CD6) and control COS cells transfected with pSVneo (COS-neo) were used in suspension binding assays with TE cells. To differentiate between COS cells and TE cells, TE cells were metabolically labelled with 1 µM calcein AM (Molecular Probes, Eugene, Oreg.) for 15 min at 37° C. in PBS prior to harvest. Calcein AM-labelled cells are fluorescent and can be differentiated from non-labelled cells by fluorescence microscopy.

Screening of mAbs for inhibition of CD6-Rg binding to TE cells. Mabs from the blind panel of the 5th International Workshop on Human Leukocyte Differentiation Antigens and a panel of anti-integrin mabs were screened for reactivity to the surface of TE cells. Of the 154 mAbs that reacted with TE cells, 126 were used in this assay. TE cells (10$^5$) were incubated with ascites or purified mAb at a dilution of 1:100 for 15 min at 4° C. Either CD5-Rg (5µg) or CD6-Rg (5 µg) were added to this mixture and allowed to react for 2 hrs at 4° C. After washing with PBS containing 2% BSA, CD5-Rg and CD6-Rg were labelled with a fluorescein-conjugated antiserum specific for the Fc portion of human IgG (Sigma). To account for any cross-reactivity with murine Ig that may have occurred with fluorescein-conjugated anti-human IgG, binding was determined as the difference in fluorescence (ΔFL) between samples containing CD6-Rg and CD5-Rg. The ΔFL of samples preincubated with control mAb P3 represented 100% binding.

Antibody blocking studies. MAb J4-81 was purified from ascites using a protein G-sepharose column (Pierce, Rockford, Ill.) and biotinylated with sulfo-NHS-biotin (Pierce) as recommended by the manufacturer. Biotin-J4-81 (1 µg/ml) was bound to the surface of TE cells in the presence of variable doses of mAbs A3D8, J4-81 or J3-119. After incubation with FITC-conjugated streptavidin (Southern Biotechnology Associates, Inc., Birmingham, Ala.), cells were washed, fixed with 0.4% paraformaldehyde and analyzed by flow cytometry.

Immunoprecipitation and protein labelling conditions. TE cells were metabolically labelled with 120 µCi/ml $^3$H-glucosamine (New England Nuclear, Boston, Mass.), harvested and immunoprecipitated as previously described (Wee et al, Cell. Immunol. (1994)). TE cell surface proteins were labelled with 125I (New England Nuclear) using lactoperoxidase as previously described (Jones, Analysis of radiolabeled lymphocyte proteins by one- and two-dimensional polyacrylamide gel electrophoresis. In: Selected methods in cellular immunology. Mishell and Shiigi, eds. W. H. Freeman and Company, New York, pp. 398–440 (1980)).

Protein cross-linking. TE cells, surface labelled with $^{125}$I, were incubated with mAbs (1:100 ascites), purified immunoglobulin (200 µg/ml) or recombinant immunoglobulin fusion proteins (200 µg/ml) for 2–4 hours in DME/5% FBS. After extensive washing with cold PBS, bound immunoglobulins were cross-linked to cell surface proteins with 1 mM DTSSP (Pierce) in PBS for 60 min at 4° C. DTSSP was inactivated with 20 mM Tris-HCl (pH 8.0) and the cells were washed with cold PBS. Cells were lysed in PBS containing 1% NP-40, 1 mM PMSF, 0.1 mM TLCK and 0.1% $NaN_3$. Immunoglobulin complexes were purified with protein A-sepharose beads (Sigma). Prior to SDS-PAGE, protein complexes were solubilized with SDS loading buffer (2% SD, 10 mM Tris-HCl pH 7.4, 20% glycerol, bromphenol blue) containing 2% 2-mercaptoethanol (2-ME) to cleave the cross-linker. To confirm identity of proteins, purified protein complexes were treated with 0.2% trypsin in 1 mM EDTA for 30 min at 25° C. (Patel et al, Virology 149:174 (1986)) prior to solubilization and cross-linker cleavage. After electrophoresis of proteins in discontinuous SDS-polyacrylamide gels, the gels were fixed in 40% methanol, impregnated with Amplify$^R$ reagent (Amersham, Arlington Heights, Ill.) dried and exposed to autoradiography film or imaged using a PhorphorImager System (Molecular Dynamics, Sunnyvale, Calif.).

Immunohistology. Normal human tissues were obtained as discarded tissue from the Department of Pathology, Duke University Medical Center and frozen in liquid nitrogen. Indirect IF assays of mAb reactivity on acetone fixed tissue sections were performed as described (Haynes et al, J. Invest. Dermatol. 768:323 (1982)).

Figure 16A:
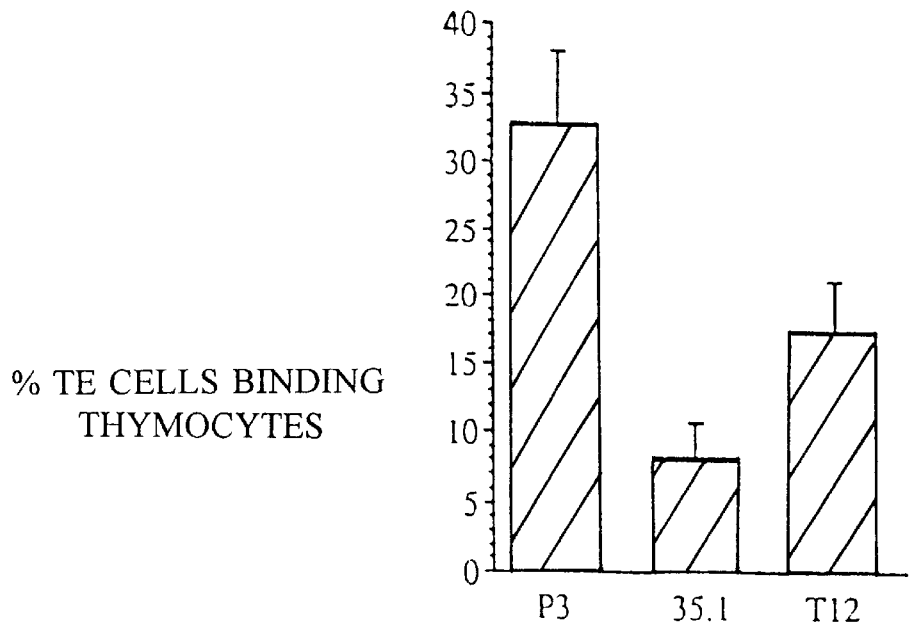
(FIGS. 16A and 16B) CD6-CD6 ligand interactions mediate TE-thymocyte binding. Shown is a summary of 5 separate TE-thymocyte binding experiments.
Figure 16B:
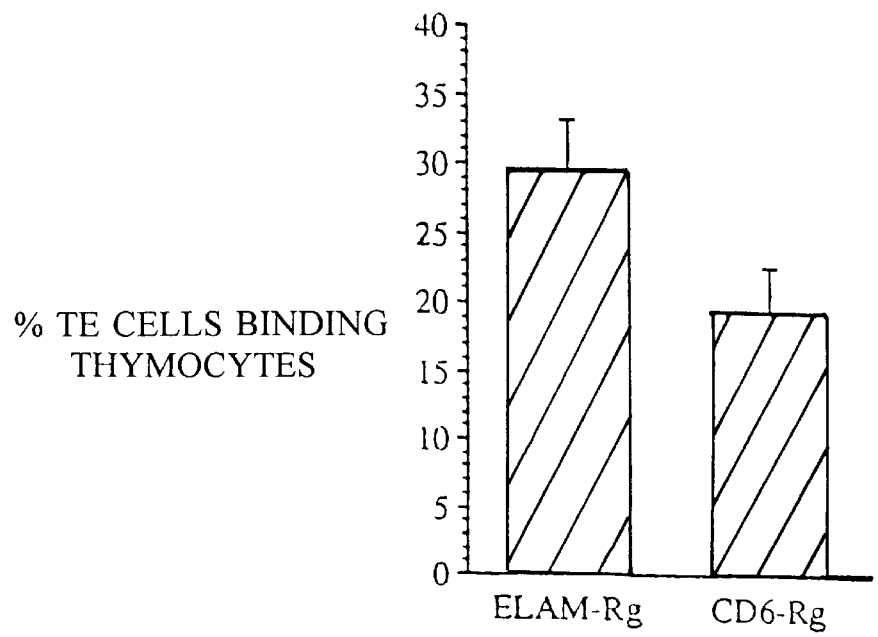

Results:

Effect of anti-CD6 antibodies and CD6-Rg on TE-thymocyte binding. The role of CD6 in the binding of thymocytes to TE cells was determined using a TE-thymocyte suspension binding assay. Both antibody to CD6 (T12) and recombinant CD6-immunoglobulin fusion protein (CD6-Rg) inhibited the binding of thymocytes to TE cells (FIG. 16). As previously reported (Patel and Haynes, Semin. Immunol. 5:283 (1993)), anti-CD2 mAb 35.1 (as a positive control) inhibited TE-thymocyte binding by 76±5% (p<0.003). Anti-CD6 antibody T12 inhibited TE-thymocyte binding by 49±9% (p<0.015). Similarly, the CD6 human Ig fusion protein, CD6-Rg, inhibited TE-thymocyte binding by 35±9% (p<0.05). Addition of a combination of saturating amounts of mAbs 35.1 and T12 to TE-thymocyte binding assays resulted in a level of inhibition of binding (74±10% inhibition) that was not significantly different from blocking by mAb 35.1 alone. Nonetheless, the data with anti-CD6 mAb and CD6-Rg suggested that CD6 may be an adhesion molecule that participates in the binding of thymocytes to TE cells, and that there may be a ligand for CD6 on human TE cells.

Figure 17A:
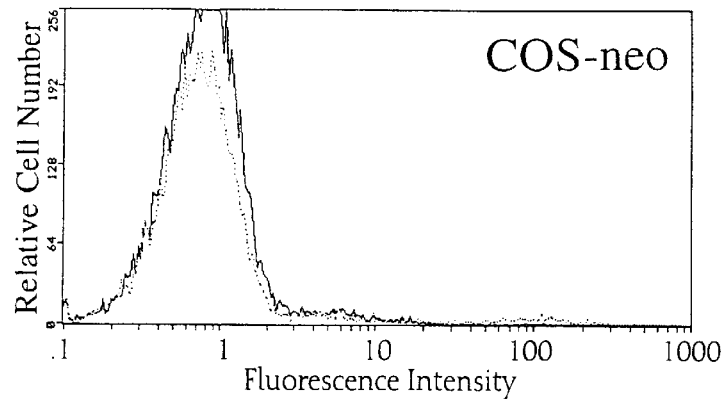
FIGS. 17A to 17C. Binding of COS-CD6 to TE cells is CD6-specific. Shown are histograms of CD6 expression on COS-neo (control) cells (FIG. 17A) and COS-CD6 cells (FIG. 17B) as determined by indirect immunofluorescence with mAb T12 and flow cytometry. Background fluorescence (control mAb P3) is depicted by a dotted line and CD6 expression is indicated by a solid line. The bar graph (FIG. 17C) depicts COS-neo and COS-CD6 binding to TE cells in the presence of either mAbs P3 or T12. Shown are the mean and SEM of three separate experiments.
Figure 17B:
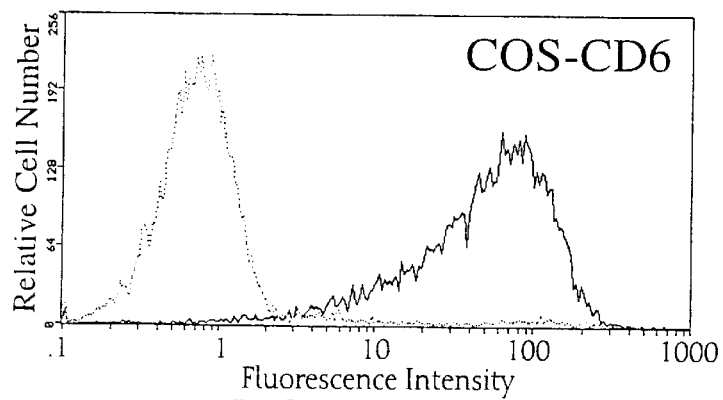
Figure 17C:
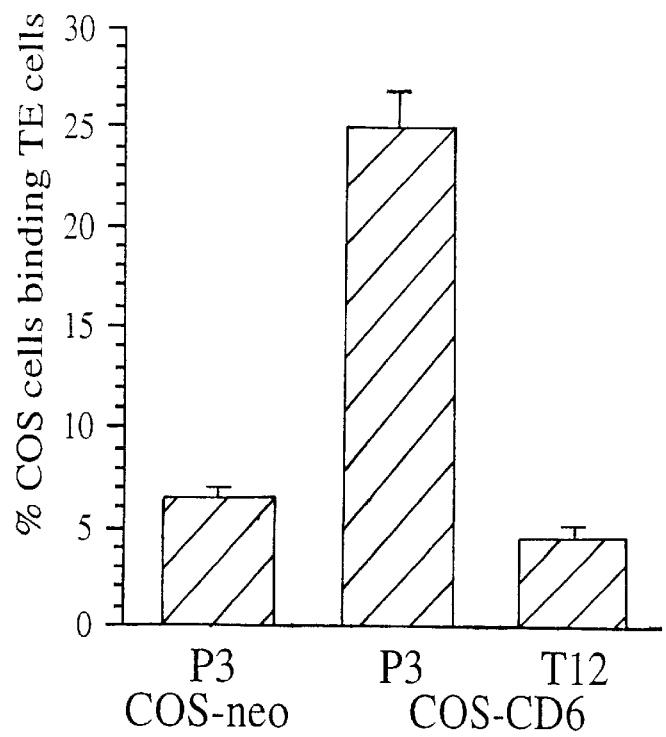
Figure 18A:
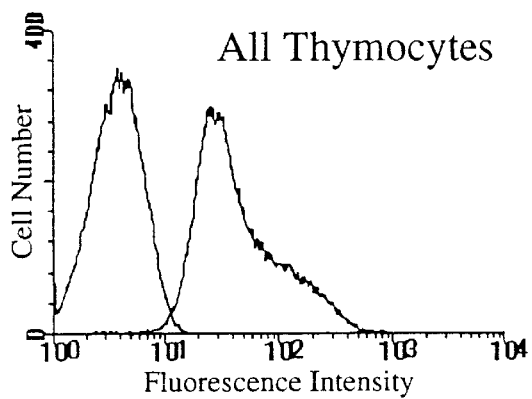
FIGS. 18A to 18D. Expression of CD6 on thymocyte subsets. Thymocytes were stained with mAb T12, fluorescein conjugated Fab fragments of goat anti-mouse IgG and a combination of CD4-PE and CD8-cychrome and analyzed on a FACStar$^{Plus}$ flow cytometer. Shown are data representative of experiments on 3 different thymuses with histograms of CD6 expression on all thymocytes (FIG. 18A), CD4+CD8+ (immature, DP) thymocytes (FIG. 18B), CD4+ CD8– (mature, SP4) (FIG. 18C) and CD4-CD8+ (mature, SP8) thymocytes (FIG. 18D). Background fluorescence (with control mAb P3) is shown in each histogram.
Figure 18B:
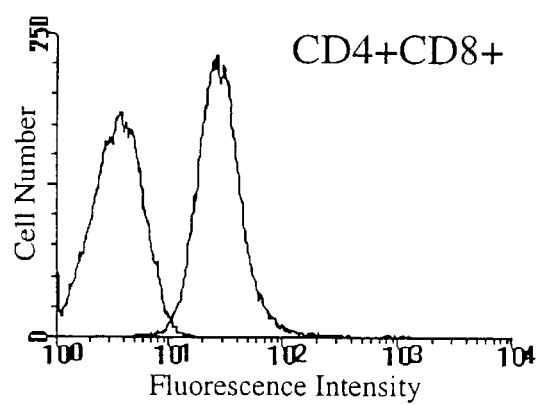
Figure 18C:
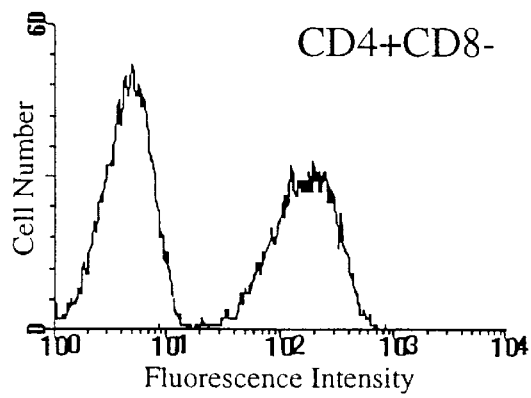
Figure 18D:
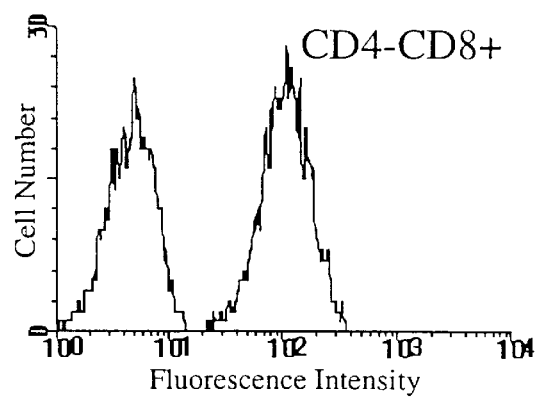

Binding of CD6-expressing COS cells to TE cells. Although inhibition of TE-thymocyte binding with both anti-CD6 antibody and CD6-Rg was suggestive that CD6 was an adhesion molecule, inhibition of TE-thymocyte binding may have occurred because of stearic hinderance. To confirm that CD6 was an adhesion molecule, stable transfectants of CD6-expressing COS cells (COS-CD6) were constructed (FIG. 17). COS cells transfected with pSVneo only (COS-neo) did not bind well to TE cells (6±1% COS-neo binding TE cells), whereas COS-CD6 did bind to TE cells (25±2% COS-CD6 binding TE cells, p<0.01) (FIG. 17). The specificity of the COS-CD6/TE binding was examined by testing for the inhibition of COS-CD6/TE binding by CD6 mAb T12. Compared to control mAb P3 and COS-neo cells (6±1% COS-neo binding TE), CD6 mAb T12 completely inhibited the binding of COS-CD6 to TE cells (5±1% COS-CD6 binding TE, p<0.01) to baseline levels of binding (FIG. 17), confirming that COS-CD6/TE binding was CD6-specific.

Figure 19:
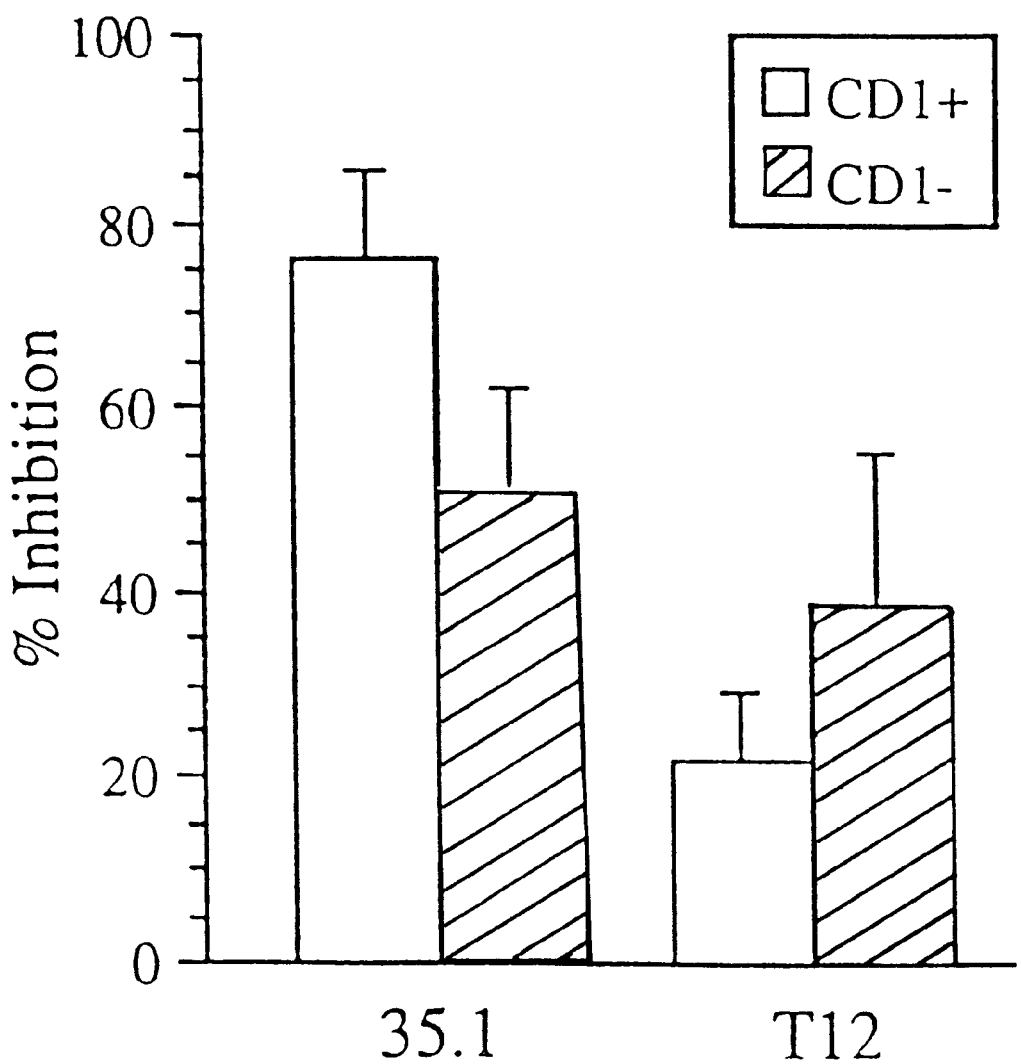
FIG. 19. CD6 mediates the binding of both mature and immature thymocytes to TE cells. CD1+ or CD1– thymocytes were incubated with TE cells in the presence of either control antibody (P3), anti-CD2 (35.1) or anti-CD6 (T12) and assayed for rosette formation. The average percentage inhibition of TE-thymocyte binding and SEM (relative to control antibody) by anti-CD2 and anti-CD6, from 3 separate experiments, is shown. Inhibition of CD1+ (immature) thymocyte binding to TE cells is depicted by open boxes and inhibition of CD1– (mature) thymocyte binding is depicted by filled boxes. The binding of both the mature and immature subsets of thymocytes to TEC is inhibited by anti-CD2 and anti-CD6 antibodies. The difference in inhibition of CD1+ vs. CD1– cells by anti-CD2 mAb 35.1 was statistically significant ($p<0.01$) but the difference in inhibition by anti-CD6 mAb T12 was not ($p<0.25$).

Effect of anti-CD6 mAb on the binding of thymocyte subsets to TE cells. The role of CD6 in the binding of subsets of thymocytes was determined by examining the expression of CD6 on thymocyte subsets, and by testing the binding of sorted mature versus immature thymocyte subsets to TE cells in the presence of CD6 mAbs. Expression of CD6 on thymocyte subsets was determined by three color immunofluorescence and flow cymetry (FIG. 18). While all thymocytes expressed CD6, immature CD4+CD8+ double positive (DP) thymocytes were CD6$^{lo}$ and the mature CD4+ CD8− or CD4−CD8+ single positive (SP) thymocytes were CD6$^{hi.}$ To determine the role of CD6 in the binding of thymocyte subsets to TE cells, thymocytes were separated into CD1+ and CD1− subsets by fluorescence activated cell sorting. CD1 was chosen because CD1+ thyocytes are the DP CD6$^{lo}$ cells and CD1− thymocytes are the SP CD6$^{hi}$ cells, and CD1 mAbs do not inhibit TE-thymocyte binding (Patel and Haynes, Semin. Immunol. 5:283 (1993)). Both CD1+ and CD1− thymocytes bound well to TE cells (45±4% and 54±6%, respectively, p=NS). CD2 mAb 35.1 inhibited the binding of immature thymocytes (77±9% inhibition) to a greater degree than that of mature thymocytes (52±11% inhibition) (p<0.01). CD6 mAb T12 also inhibited the binding of both immature (22±7% inhibition) and mature (39±17% inhibition) thymocytes to TE cells (p<0.25) (FIG. 19).

Figure 20A:
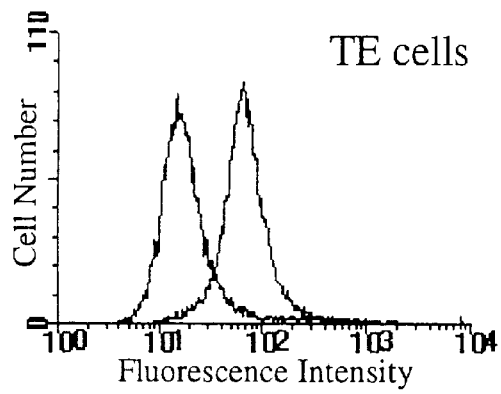
FIGS. 20A to 20F. Thymic epithelial cells and thymic fibroblasts express a trypsin-sensitive surface ligand for CD6. Shown are representative histograms depicting the reactivities with CD6-Rg of thymic is epithelial cells (FIG. 20A), thymic fibroblasts (FIG. 20B), and thymocytes (FIG. 20C). Also shown in each panel are background levels of fluorescence with control fusion protein CD5-Rg. The binding of CD6-Rg to TE cells in either divalent cation containing media (–EDTA) (FIG. 20D), trypsin-treated TE cells in media (trypsin) (FIG. 20E) or TE cells in PBS+10 mM EDTA (EDTA) (FIG. 20F) was tested. Shown are histograms of a representative experiment (from >10 performed) depicting CD6-Rg binding to TE cells as determined by indirect IF and flow cytometry.
Figure 20B:
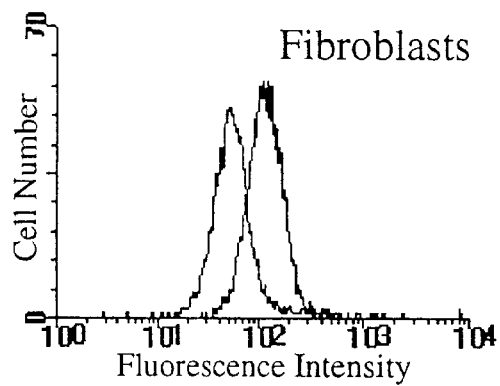
Figure 20C:
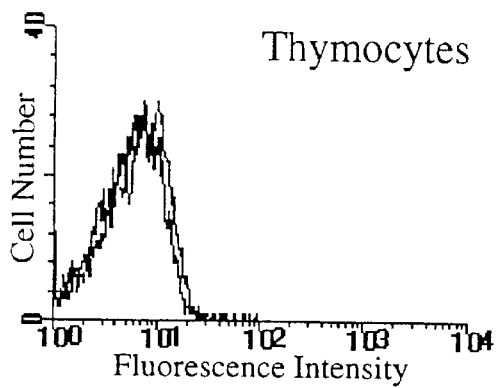
Figure 20D:
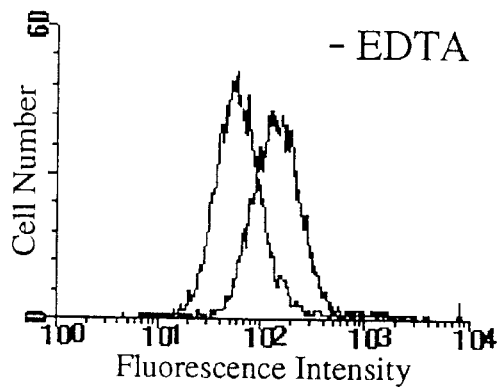
Figure 20E:
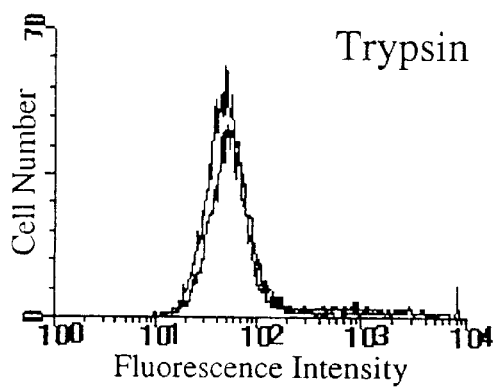
Figure 20F:
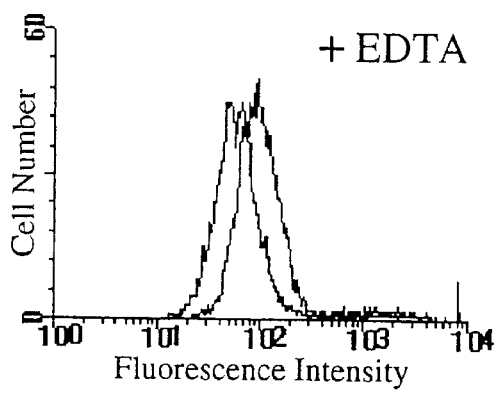
Figure 21A:
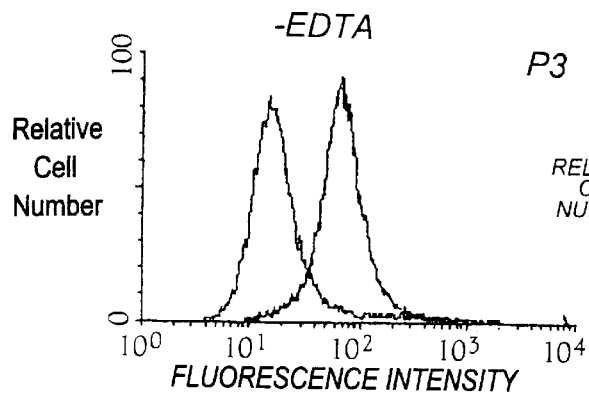
FIGS. 21A to 21H. Effect of preincubation of J4-81 and J3-119 on CD6-Rg binding to TE cells. Shown are histograms of CD6-Rg binding to the surface of human TE cells, as detected by indirect IF and flow cytometry, in the presence of mAbs P3 (control), J4-81 or J3-119 in media containing divalent cations (–EDTA) (FIG. 21A, FIG. 21C and FIG. 21E, respectively) or no divalent cations (+EDTA) (FIG. 21B, FIG. 21D and FIG. 21F, respectively). The binding of control human IgG is shown in each panel.
Figure 21B:
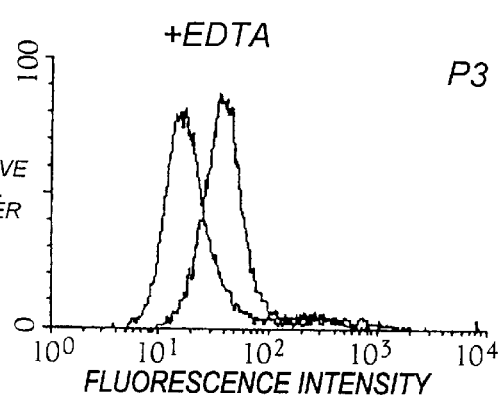
Figure 21C:
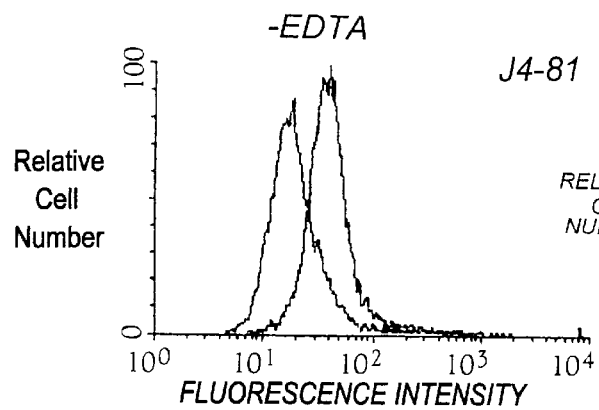
Figure 21D:
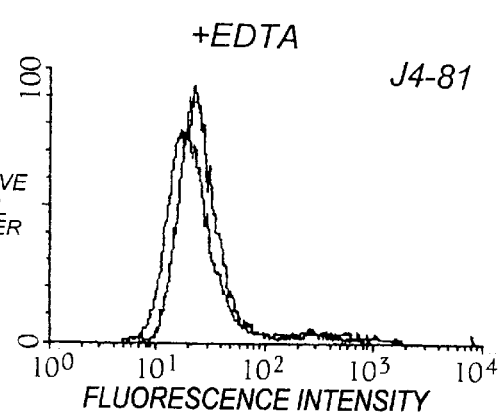
Figure 21E:
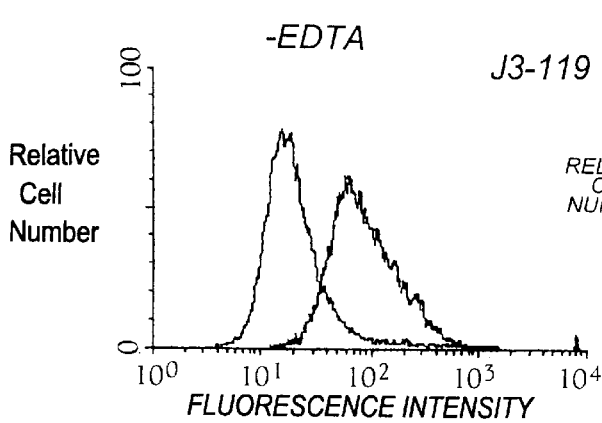
Figure 21F:
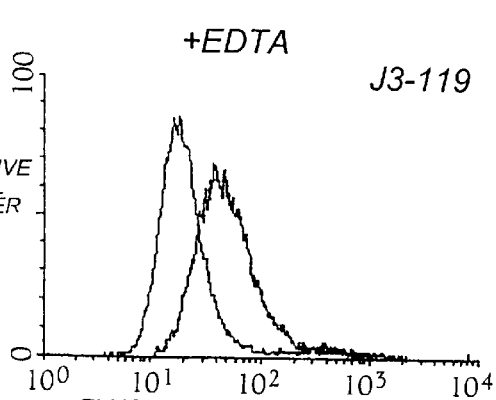
Figure 21G:
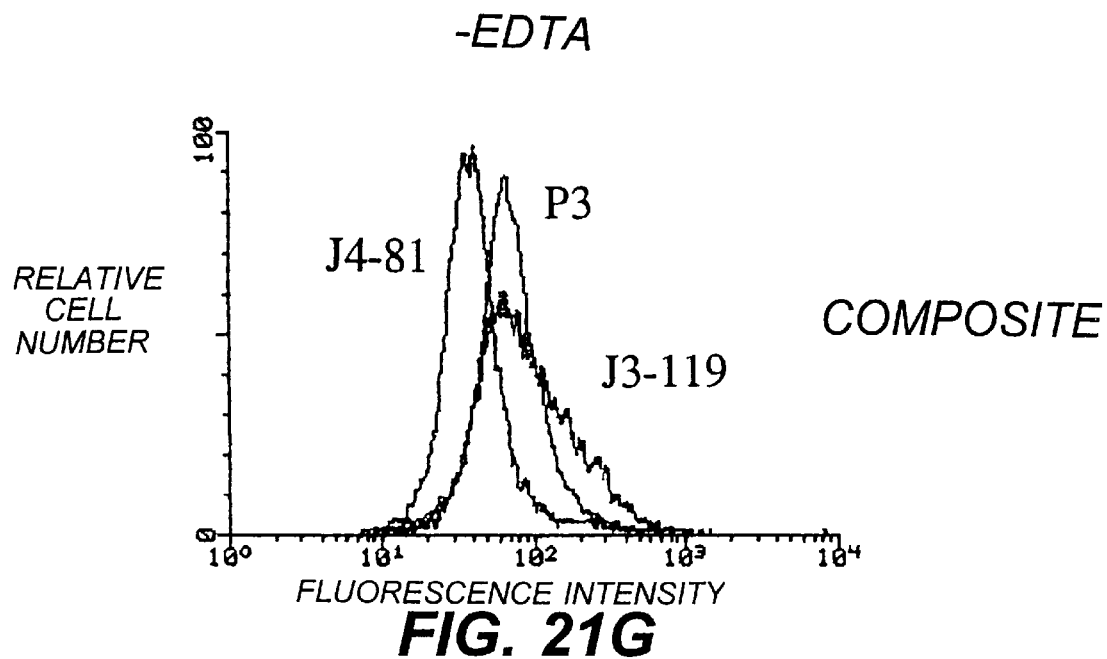
Figure 21H:
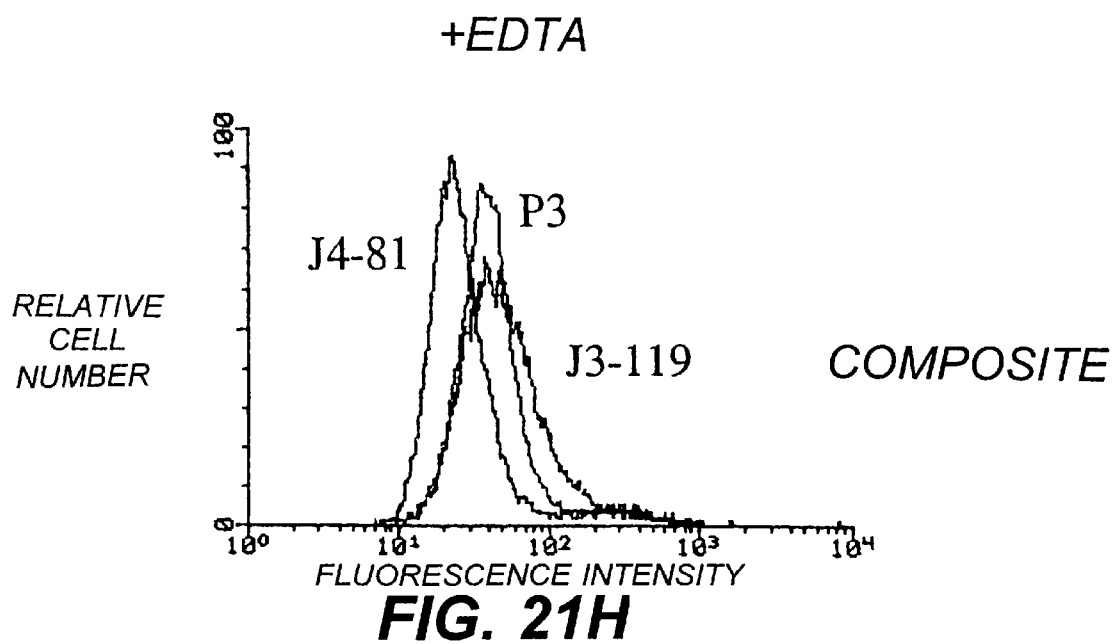

CD6-Rg binding to cells of the thymic microenvironment. The ability of CD6-Rg fusion protein to bind to TE cells, thymic fibroblasts and to thymocytes was determined by indirect IF and flow cytometry. CD6-Rg bound to the surface of TE cells as well as to thymic fibroblasts, but not to thymocytes (FIG. 20A). Binding of CD6-Rg to TE cells was trypsin-sensitive and partially dependent upon divalent cations (FIG. 20B). CD6-Rg bound well to TE cells in a buffer containing DME and 5% FBS, but in the presence of 10 mM EDTA, binding of CD6-Rg to TE cells was inhibited by 54±4% (N=5, p<0.001, FIG. 20B). To further evaluate the divalent cation-dependence of CD6-Rg binding, CD6-Rg binding was determined in buffers containing 5 mM $CaCl_2$, 5 mM $MgCl_2$ or 5 mM $MnCl_2$. While both $CaCl_2$ and $MnCl_2$ enhanced the binding of CD6-Rg to TE cells (144±5%, p=0.01, and 318±22%, P<0.01, respectively), $MgCl_2$ did not affect CD6-Rg binding (94±2%, p=NS).

Antibody-mediated inhibition of CD6-Rg binding to TE cells. To begin to identify the CD6 ligand(s), a panel of 479 mAbs from the 5th International Workshop on Human Leukocyte Differentiation Antigens was screened for reactivity to the surface of TE cells by indirect immunofluorescence and flow cytometry (Shaw, Concepts of cross-lineage (blind panel) analysis of expression of differentiation antigens. In: Leukocyte Typing, Schlossman et al, eds, Oxford University Press, Oxford (1994)). Of the 154 mAbs that reacted with the surface of TE cells, 126 mAbs were used in assays to inhibit the binding of CD6-Rg to TE cells. Of the 122 mAbs that did not react with the secondary antiserum, only one (J4-81) inhibited the binding of CD6-Rg to TE cells. MAb J4-81 inhibited the binding of CD6-Rg to TE cells by 60±7% (N=10, p<0.001) and to the breast cell line HBL-100 by 40±3%. (N=3, p<0.02) (Table 4), which has also been shown to bind CD6-Rg (Wee et al, Cell. Immunol. (1994)). In flow cytometry assays, both TE cells and HBL-100 cells reacted strongly with mAb J4-81.

TABLE 4

MAb inhibition of CD6-Rg binding to TE and HBL-100 cells.

| Cell Type | mAb | Δ Fluorescence* | % Binding‡ | % inhibition§ |
|---|---|---|---|---|
| TE cells | P3 | 52 | 100 | 0 |
| | CD9 | 60 | 115 | −15 |
| | CD24 | 48 | 92 | 8 |
| | CD40 | 48 | 92 | 8 |
| | CD46 | 57 | 110 | −10 |
| | CD51 | 46 | 88 | 12 |
| | CD54 | 44 | 85 | 15 |
| | CD58 | 45 | 87 | 13 |
| | CD59 | 52 | 100 | 0 |
| | CD63 | 53 | 102 | −2 |
| | CD66 | 56 | 108 | −8 |
| | J4-81 | 21 | 40 | 60 |
| HBL-100 | P3 | 58 | 100 | 0 |
| | J4-81 | 34 | 59 | 41 |

*Δ Fluorescence = Fluorescence (CD6-Rg) − Fluorescence (CD5-Rg). Shown is the binding of CD6-Rg compared to control (CD5-Rg) in the presence of selected mAbs that bind well to the surface of TE cells.
‡% Binding = 100 [ΔFL (experimental mAb) − ΔFL (P3)]/ΔFL (P3).
§% Inhibition = 100 [ΔFL (P3) − ΔFL (experimental mAb)]/ΔFL (P3).

Figure 22:
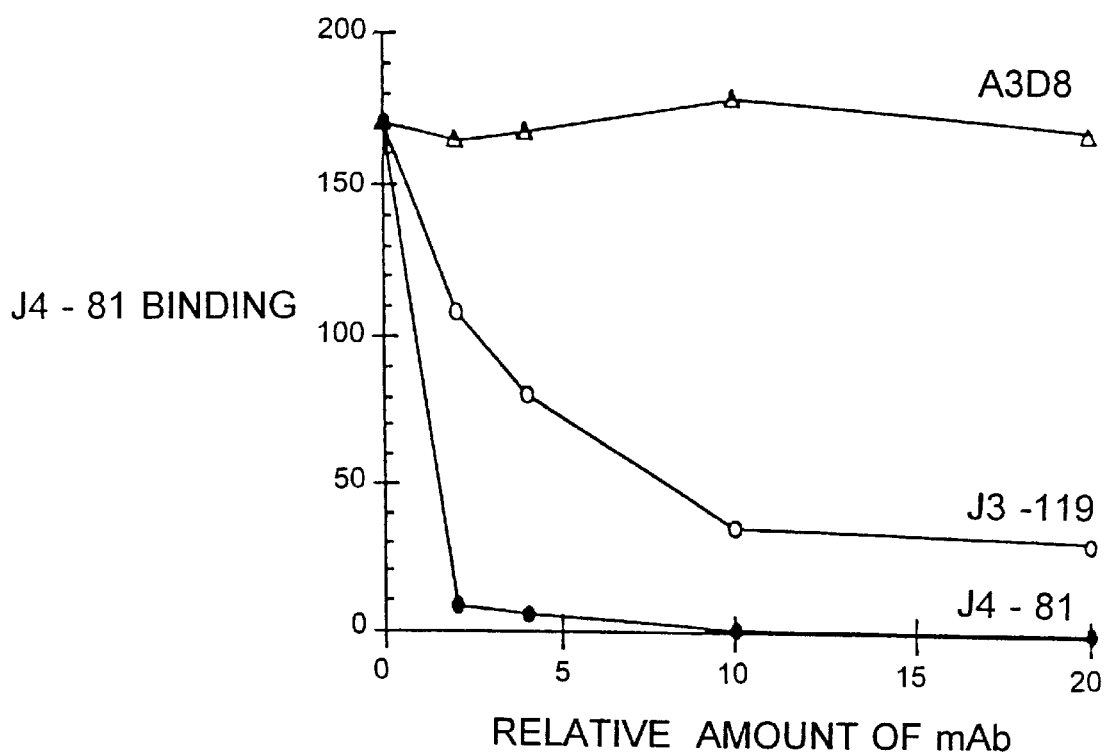
FIG. 22. MAb J3-119 blocks the binding of biotinylated J4-81 to the surface of TE cells. Shown is the specific binding of biotinylated J4-81 (in fluorescence units minus background) in the presence of increasing concentrations of mAbs A3D8, J3-119 and J4-81. Diluted ascites (1:50, 1:100, 1:250 and 1:500) was used and relative amount of mAb is presented as the inverse of the dilution$\times 10^{3\cdot}$ MAb A3D8, which binds strongly to the surface of TE cells did not alter the binding of J4-81 while both J3-119 and non-biotinylated J4-81 inhibited the binding of biotinylated J4-81. Data are representative of 2 experiments.

MAb J3-119, reported to react with a second epitope on the molecule detected by J4-81 (Pesando et al, J. Immunol. 137:3689 (1986)), enhanced the binding of CD6-Rg to TE cells (FIG. 21) by 48±5% (N=6, P<0.005), and to HBL-100 cells by 45±11% (N=3, p<0.1). To confirm that mAb J3-119 recognized the same protein as mAb J4-81, the ability of mAb J3-119 to block the binding of biotinylated J4-81 to TE cells was tested. While mAb A3D8 to CD44 (which binds well to the surface of TE cells had no effect on J4-81 binding, both J4-81 and J3-119 mAbs inhibited the binding of biotinylated J4-81 (99% and 82%, respectively) (FIG. 22). Moreover, mAb J4-81 modulated surface expression on B cells of the antigen detected by J3-119 (Pesando et al, J. Immunol. 137:3689 (1986)).

To further establish that mAb J4-81 recognized a ligand for CD6, the ability of J4-81 to inhibit the CD6-specific binding of COS-CD6 cells to TE cells was tested. MAb J4-81 significantly inhibited the binding of TE cells to COS-CD6 cells (87±1%, N=3, p<0.001), thus confirming that J4-81 recognized a CD6 ligand.

Figure 23:
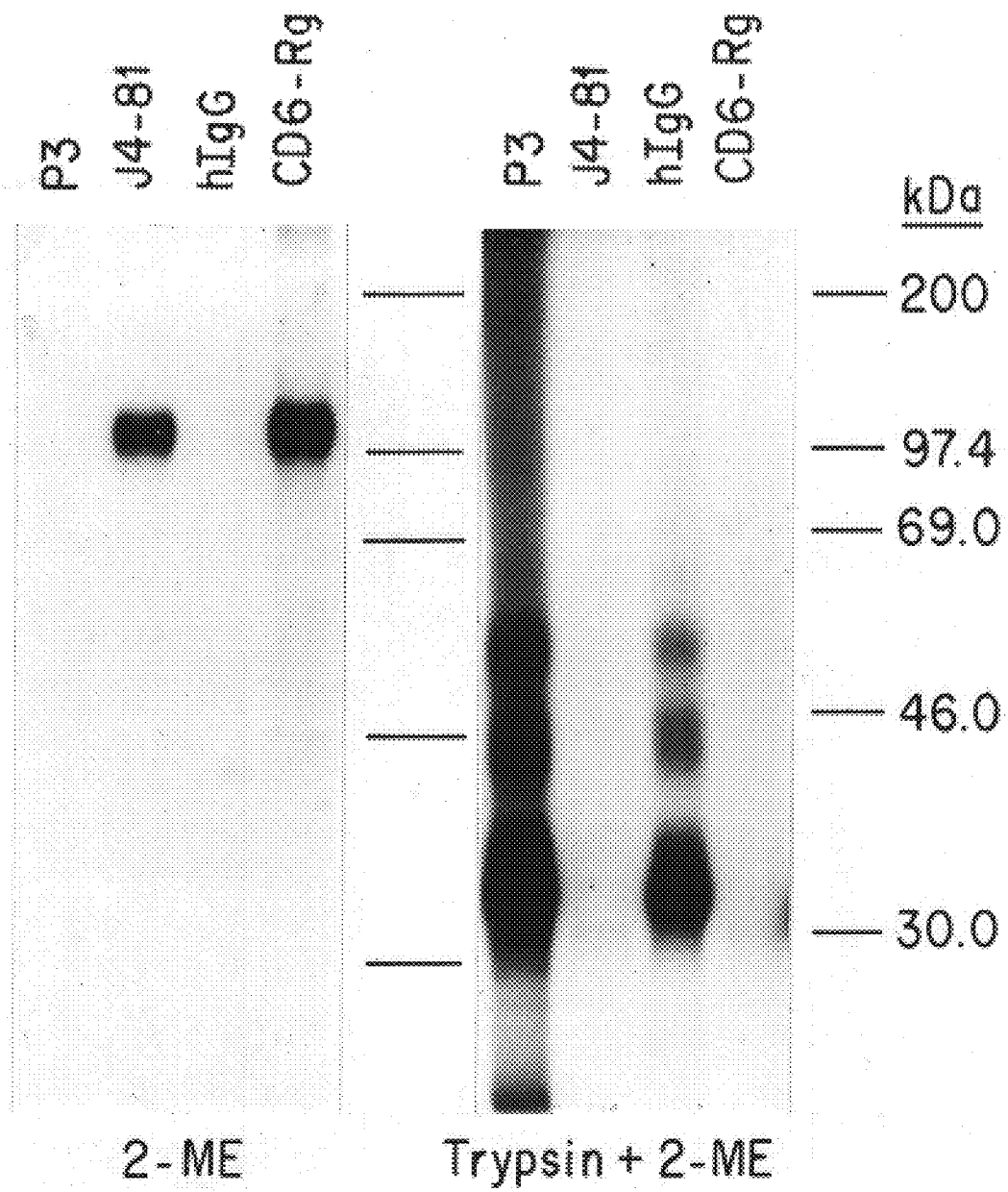
FIG. 23. MAb J4-81 and CD6-Rg bind to the same 100 kDa glycoprotein on the surface of human TE cells. Shown are autoradiographs of $^{125}$I-labelled TE cell surface proteins cross-linked to either mAb P3 (control), mAb J4-81, hIgGI (human Fc control), or CD6-Rg. The cross-linked proteins were treated with either 2-ME alone (to cleave the cross-linker) or trypsin and 2-ME prior to electrophoresis. Both CD6-Rg and mAb J4-81 bound to 100 kDa proteins with identical trypsin digestion patterns. Data are representative of 2 separate experiments.

MAb J4-81 and CD6-Rg bind 100 kDa TE cell proteins that are identical. To identify the TE cell surface protein(s) that bound to CD6-Rg, a strategy was devised whereby CD6-Rg interactions with CD6 ligand(s) on surface $^{125}$I labelled TE cells were stabilized with DTSSP, a cleavable homobifunctional cross-linking reagent reactive with free amino groups, and CD6-Rg containing complexes were purified using protein A-sepharose beads. Using this strategy, CD6-Rg specifically reacted with a 100 kDa TE cell surface protein (FIG. 23). MAb J4-81 cross-linked to $^{125}$I labelled TE cells also yielded an 100 kDa protein that migrated with the 100 kDa protein recognized by CD6-Rg (FIG. 23). Trypsin digestion studies showed that the 100 kDa protein identified by J4-81 had an identical trypsin digestion pattern to the 100 kDa protein identified by CD6-Rg (FIG. 23), indicating that both proteins were identical. MAb J4-81 also specifically immunoprecipitated an 100 kDa protein from extracts of TE cells metabolically labelled with $^3$H-glucosamine.

The 100 kDa CD6 ligand is a divalent cation-independent ligand for CD6. The immunoprecipitation studies (above) showed that CD6-Rg was able to immunoprecipitate a 100 kDa protein in the presence and absence of divalent cations. Thus, the 100 kDa protein may be a divalent cation-independent CD6 ligand. Further, J4-81 only partially inhibited the binding of CD6-Rg to TE cells in the presence of divalent cations, suggesting that there may be more than one ligand for CD6. MAb J4-81 nearly completely inhibited (80±10% inhibition, p<0.1) CD6-Rg binding to TE cells in the presence of EDTA (FIG. 21), confirming that the protein recognized by JA-81 is primarily involved in divalent cation-independent CD6-CD6 ligand interactions. In contrast, mAb J3-119 enhanced CD6-Rg binding by 47±7%. (p<0.1) in the absence of divalent cations (FIG. 21).

Figure 24A:
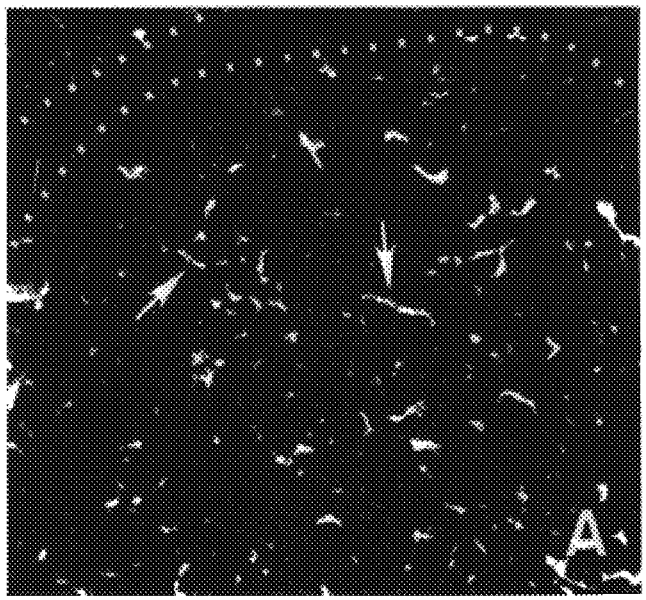
FIGS. 24A and 24B. Expression of CD6L-100 or ALCAM in postnatal human thymus. Shown are photomicrographs (representative of experiments on 5 thymuses) of frozen sections of 2 month human thymus stained by indirect IF with mAb J4-81.
Figure 24B:
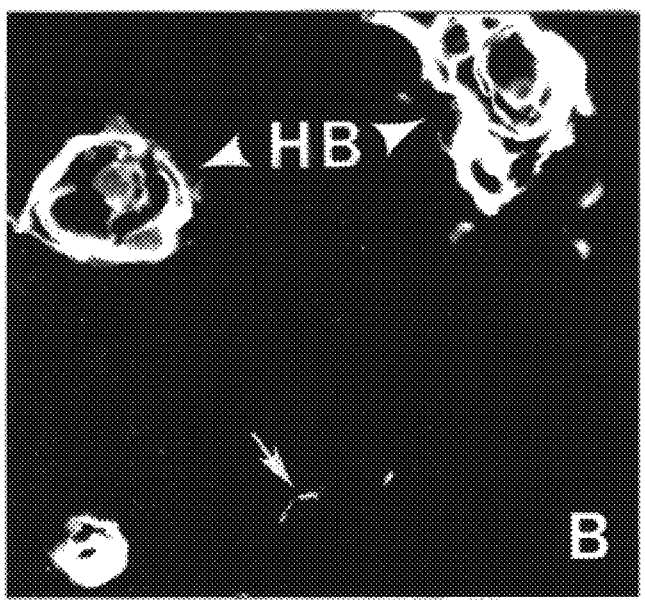

Tissue distribution of mAb J4-81 reactivity. The tissue distribution of the 100 kDa glycoprotein recognized by J4-81 was examined on frozen sections of a variety of human tissues by indirect IF (Table 5). The reactivity of mAb J4-81 with human tissues and cell lines was broad. While CD6 was expressed on thymocytes in postnatal human thymus, the 100 kDa CD6 ligand was expressed on cortical and medullary TE cells and Hassall's bodies (FIG. 24). In tissues other than thymus, J4-81 reacted with epidermal keratinocytes, gut epithelium, breast epithelium, pancreatic acinar and islet cells, hepatocytes, renal tubular epithelium, neurons of the cerebral cortex, and fibroblasts.

TABLE 5

Reactivity of mAb J4-81 in sections of normal human tissues.

| Tissue (Number Tested) | J4-81 Reactivity |
| --- | --- |
| Thymus (5) | Hassall's bodies, epithelium, fibroblasts |
| Spleen (2) | Scattered mononuclear cells |
| Lymph Node (1) | Scattered mononuclear cells |
| Tonsil (2) | Pharyngeal epithelium, lymphocytes |
| Appendix (1) | Fibroblasts, lymphoid cells, epithelium |
| Colon (2) | Fibroblasts, epithelium |
| Esophagus (2) | Basal epithelium |
| Breast (2) | Epithelium, fibroblasts |
| Liver (2) | Hepatocytes, Kupfer cells, fibroblasts |
| Pancreas (2) | Acinar and islet cells |
| Kidney (2) | Fibroblasts, subset of tubules, Bowman's capsule |
| Skin (2) | Perivascular fibroblasts, epithelium |
| Brain (2) | Neurons |

The cell types reacting with mAb J4-81 in each of the tissue types are listed.

EXAMPLE IV

Experimental details:

Cells lines, tissue culture, antibodies. TE cells were cultured by an explant technique as described (Singer et al, Human Immunol. 13:161 (1985); Singer et al, J. Invest. Dermat. 92:166, (1989)). COS cells, breast carcinoma HBL-100, B cell lymphoma cell lines Ramos, Raji and Daudi, T cell lymphoma cell lines CEM and MOLT4, erythroleukemia cell line K562, and monocyte-like cell lines HL60 and U937 were obtained from ATCC (Rockville, Md.) and maintained under standard tissue culture conditions in Iscove's Modified Dulbecco's Medium plus 10% fetal bovine serum. NK-like cell line YT was obtained from E. Podack (Univ. of Miami Sch. of Medicine). Antibodies used in this study were J4-81 (Pesando et al, J. Immunol. 137:3689 (1986)) as ascites, Leu4 (anti-CD3)-phycoerythrin (Becton Dickinson, San Jose, Calif.), G3-6 (anti-CD6 from J. Ledbetter, Bristol-Myers Squibb), anti-L6 (Bristol-Myers Squibb, ATCC), T12 (anti-CD6, ATCC), and P3 (ATCC).

Binding of TE cells to COS cell transfectants expressing CD6. COS-CD6 and COS-neo cells were prepared by co-transfecting a plasmid encoding CD6 (Aruffo et al, J. Exp. Med. 174:949 (1991)), and the pSVneo plasmid (Liao et al, J. Immunol. 151:6490 (1993)). Following G418 selection, CD6+cells were cloned using a Becton-Dickinson FACStar$^{PLUS}$ fluorescence activated cell sorter. COS-neo and COS-CD6 TE cells were used in a suspension binding assay. To differentiate between COS cells and TE cells, TE cells were labeled with 1 μM calcein AM (Molecular Probes, Eugene, Oreg.) for 15 min. at 37° C. in PBS prior to harvest. Calcein AM-labeled cells are fluorescent and can be differentiated from unlabeled cells by fluorescence microscopy. Adhesion was quantitated by scoring the percentage of COS-CD6 cells that were conjugated with TE cells. For blocking adhesion, antibodies T12, J4-81, and P3 were used at or in excess of saturating binding titers.

Cloning and characterization of the gene for the antigen recognized by mAb J4-81. J4-81 immunoaffinity purification of ALCAM from HBL-100 cells (~3×10$^9$) was performed as described (Bowen et al, J. Immunol. 151:5896 (1993)). The purified protein and CNBr fragments were analyzed in a pulsed-liquid protein sequencer by previously described methods (Maresh et al, Arch. Biochem. Biophys. 311:95 (1994)). Amino-terminal sequences were screened against the SwissProt data base using Genetics Computer Group (GCG) sequence-analysis software. Chicken BEN probes were synthesized by PCR from a chicken embryo cDNA library (Clontech), random prime labeled with $^{32}$P-dCTP, and used to screen a PHA activated human T cell cDNA library. A partial cDNA clone was isolated; 200 bp of the 5' end of this cDNA was used to isolate a clone containing the entire coding region from a HL60 cDNA library. Database searches with the cDNA derived peptide sequence of ALCAM were performed using the BLAST program, alignments and consensus sequence derivation of the four highest scoring hits were performed using the Pileup and Pretty programs from the GCG sequence analysis software.

Northern analysis. Peripheral blood mononuclear cells (PBMC) were isolated from whole blood with lymphocyte separation medium (Organon Teknika, Durham, N.C.) according to the manufacturer's instructions. PBMC were stimulated with 1 μg/ml phytohemagglutinin (PHA; Boehringer Mannheim Indianapolis, Ind.). Total cellular RNA was prepared with TRIzol reagent (Gibco BRL, Gaithersburg, Md.). Monocytes were isolated from PBMC's by adherence to plastic for 2.5 h. The RNA's were fractionated on a denaturing formaldehyde gel; 25 μg of RNA was loaded for all samples except for monocytes, where 15 μg was loaded. RNA was transferred to nitrocellulose TC (Schleicher and Schuell, Keene, N.H.) and probed with a random primed $^{32}$P-dCTP labeled ALCAM or GAPDH cDNA. Filters were exposed to film at −70° C. and developed.

PHA blast preparation, staining. PBMC were isolated and activated with PHA as described above and stained on selected days with mAb J4-81 ascites (1:200) or CD6-Rg (50 μg/ml) followed by a FITC labeled second antibody and anti-CD3-PE; cytofluorometric analysis of J4-81 staining T cells was performed on a FACScan (Becton Dickinson, San Jose, Calif.) by gating on CD3 positive cells.

Chromosomal mapping of the gene encoding ALCAM.

Two overlapping cDNA clones of the human ALCAM gene containing 2.2 kb and 1.9 kb inserts in CDM7 were used as probes for fluorescence in situ hybridization (FISH) as described (Milatovich et al, Genomics 11:1040 (1991)). The probe was labeled with biotin-dUTP by nick-translation and was hybridized at a concentration of 500 ng/50μl per slide to pre-treated and denatured metaphase chromosomes from a human PHA-stimulated lymphocyte culture. Salmon sperm DNA served as carrier but no human genomic DNA was used as competitor. After incubation, washing, signal detection with avidin-FTIC (Vector Laboratories) and one round of amplification with biotinylated goat anti-avidin D antibody (Vector Laboratories), chromosomes were counterstained with propidium iodide and analyzed under an Axiophot (Zeiss) epifluorescence microscope as described (Milatovich et al, Genomics 11:1040 (1991)). Hybridization signals were considered specific only when the signal was observed on both chromatids of a chromosome. Results were recorded by digital imaging using a cooled charge-coupled device (CCD) camera (Photometrics PM512) and displayed in pseudo-colors.

Construction of ALCAM-Rg. ALCAM-Rg was constructed by PCR technology similarly to CD6-Ig (Aruffo et al, Proc. Natl. Acad. Sci. USA 89:2292 (1992)). ALCAM cDNA in pCDM8 was used as a template. A forward oligonucleotide primer (GGCCAGATATACGCGTTGACATT) (SEQ ID NO:8) encompassing an MluI site in the CMV promoter of pDCM8 and a reverse primer (TGTATCATGTGGATCCGCCTGGTCATTCACCTTTT-CTCT) (SEQ ID NO:9) containing a BamHI site and specific for the nucleotides encoding the extracellular membrane proximal residues of ALCAM were used to synthesize a fragment that encoded a DNA fragment encoding truncated ALCAM. This PCR product was digested with MluI and BAMHI and ligated to a vector (PCDM7) that was similarly digested and encoding the hinge, CH1 and CH2 domains of human IgG1. This resulted in a chimeric gene encoding the extracellular region of ALCAM fused to the Fc portion of human IgG1. Protein was produced by transient expression of ALCAM-Rg in COS cells and purified by absorption to and elution from protein A Sepharose. Briefly, plasmid DNA was transfected into COS cells by the DEAE-dextran chloroquine method. 18–24 hours later, the 10% FBS Dulbecco's modified Eagle's medium was replaced by serum-free media after a rinse wash with PBS. The cell culture was maintained 7–10 days before it was harvested. Briefly, the supernatant containing the fusion protein was centrifuged at 2500 rpm or 20 min and filtered through a 0.45 μm Millipore filter. The supernatant was passed over a Protein A Sepharose column at a flow rate of 1.00 ml/min. The bound fusion protein was eluted with pH 3.5, 0.1 M citric acid and was immediately neutralized with pH 9.0, 1.0 M Tris. The fusion protein was dialyzed against PBS and concentrated with a Certicor concentrator (Amicon).

Binding of CD6-Rg to ALCAM expressing COS cells and binding of ALCAM-Rg to CD6 expressing COS cells. COS cells were either transfected with parent vector CDM8 or with cDNA clones encoding CD6 or ALCAM by the DEAE-dextran method (Aruffo et al, Proc. Natl., Acad., Sci., USA 84:8573 (1987)). Three days post-transfection the cells were detached with PBS/0.5 mM EDTA, washed with PBS, and resuspended in PBS/1% BSA/0.1% NaN$_3$ (PBA) containing the following concentrations of mab's or fusion proteins: J4-81 (aALCAM) 1:200 dilution of ascites, G3-6 (aCD6) 5 μg/ml, CD6-Rg 50 μg/ml, and ALCAM-Rg 25 μg/ml. After 30 min. on ice, cells were washed twice with PBA and resuspended in PBA containing either goat anti-mouse or human IgG-FITC for 30 min. on ice. The cells were washed twice in PBA, once with PBS, fixed in PBS/1 formaldehyde, and analyzed by flow cytometry.

Figure 25A:
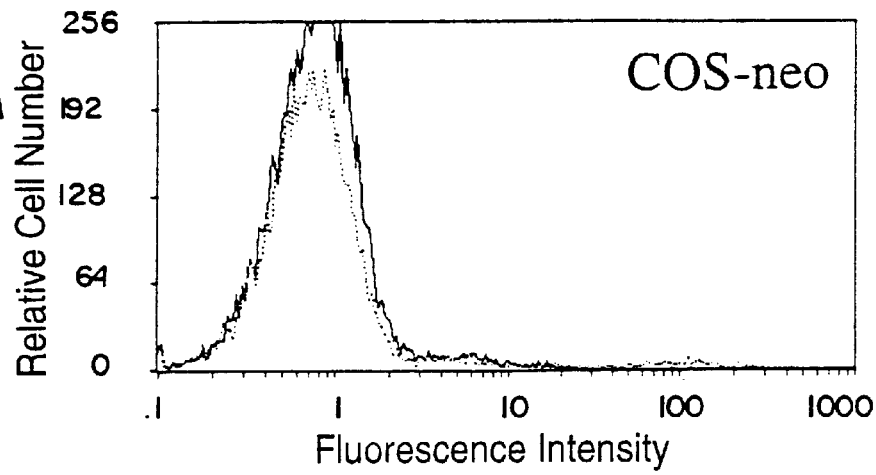
FIGS. 25A to 25C. Binding of COS-CD6 to TE cells is CD6-specific.
Figure 25B:
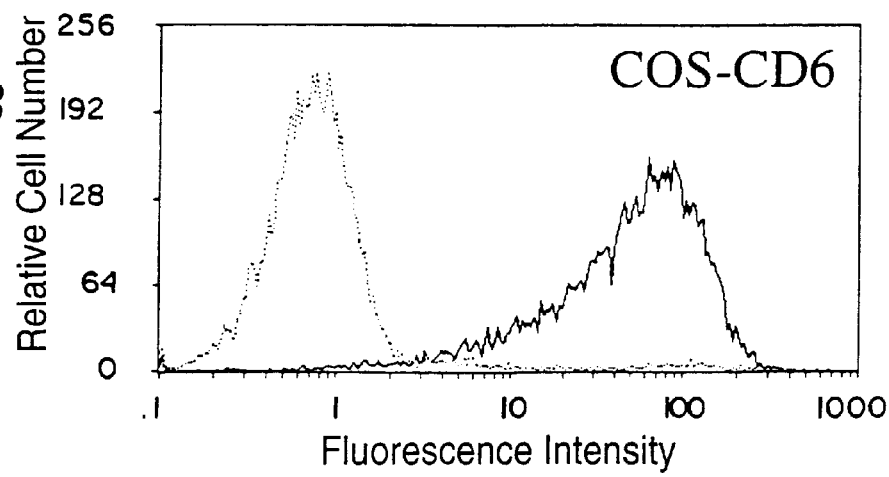
Figure 25C:
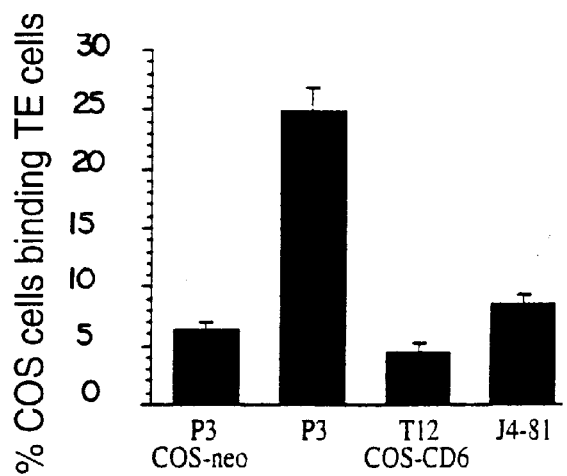

Results:

CD6 on transfected COS cells promotes TE cell adhesion. To examine directly the role of CD6 in thymocyte-TE cell adhesion, a stable COS cell transfectant expressing CD6 was prepared. COS cells expressing CD6 (COS-CD6) supported TE cell adhesion while COS cells transfected with the parent vector alone (COS-neo) did not (FIG. 25). The adhesion of TE cells to COS-CD6 cells was inhibited by pretreating the COS-CD6 cells with anti-CD6 mAb T12 or by pretreating TE cells with J4-81 mAb (FIG. 25B), indicating that CD6 mediated adhesion to TE cells involves the molecule recognized by mAb J4-81.

Cloning and characterization of the antigen recognized by mAb J4-81 (activated leukocyte-cell adhesion molecule (ALCAM)). A J4-81 affinity column was used to purify the protein from HBL-100, a breast carcinoma cell line that expressed high levels of a CD6 ligand (Wee et al, Cell. Immunol. 158:353 (1994)) and the antigen recognized by J4-81 (Patel et al, J. Exp. Med. (1994)). Amino acid sequences obtained from intact protein and internal peptide fragments were found to have substantial homology with the chicken neural adhesion molecule BEN/SC-1/DM-GRASP (Pourquie et al, Proc. Natl. Acad. Sci. USA 89:5261 (1992)); Tanaka et al, Neuron 7:535 (1991)); Burns et al, Neuron 7:209 (1991)), which was also reported to be expressed by activated chicken leukocytes (Corbel et al, Cell Immunol. 141:99 (1992)). DNA fragments corresponding to chicken BEN were obtained by PCR and used to screen a PHA activated human T cell cDNA library. A single clone that did not contain the complete coding region was isolated. A 200 bp PCR fragment derived from the 5' region of this clone was used to isolate a ~1.9 kb cDNA clone that contained the complete coding sequence from an HL60 cDNA library (the nucleotide sequence has been deposited in GenBank, accession #L38608). The two cDNA clones exhibit polymorphisms at three nucleotide positions in the region of overlap, two of which result in differences at the protein level (G to A from HL60 to the T cell clone at position 836 results in the substitution of N231 by S;C to T from HL60 to the T cell clone at position 965 results in the substitution of M274 by T).

The predicted amino acid sequence of the human homologue of chicken BEN (ALCAM), a type I membrane protein, consists of a 27 amino acid (aa) N-terminal hydrophobic signal peptide, followed by 500 aa extracellular domain, a 24 aa hydrophobic transmembrane domain, and a 32 aa cytoplasmic domain (see FIG. 29). Glycosylation of ALCAM probably accounts for much of the difference between the predicted molecular weight of ~65 kDa and the 100–105 kDa molecular weight observed by immunoprecipitation (Patel et al, J. Exp. Med. (1994)); Pesando et al, J. Immunol. 137:689 (1986)). Comparison of the aa sequence of ALCAM with others in the data base showed that it was homologous to neurolin (Lawssing et al, Differentiation 56:21 (1994)), a protein expressed by neural axons of the goldfish visual system (38% identity/55% similarity), RAGE (Neeper et al, J. Biol. Chem. 267:14998 (1992)), a receptor for advanced glycation end products (28/43%), and MUC18 (Lehmann et al, Proc. Natl. Acad. Sci. USA 86:9891 (1989)), a cell surface protein whose expression correlates with the metastatic potential of melanoma cells (23/49%) (FIG. 26A).

Figure 26B:
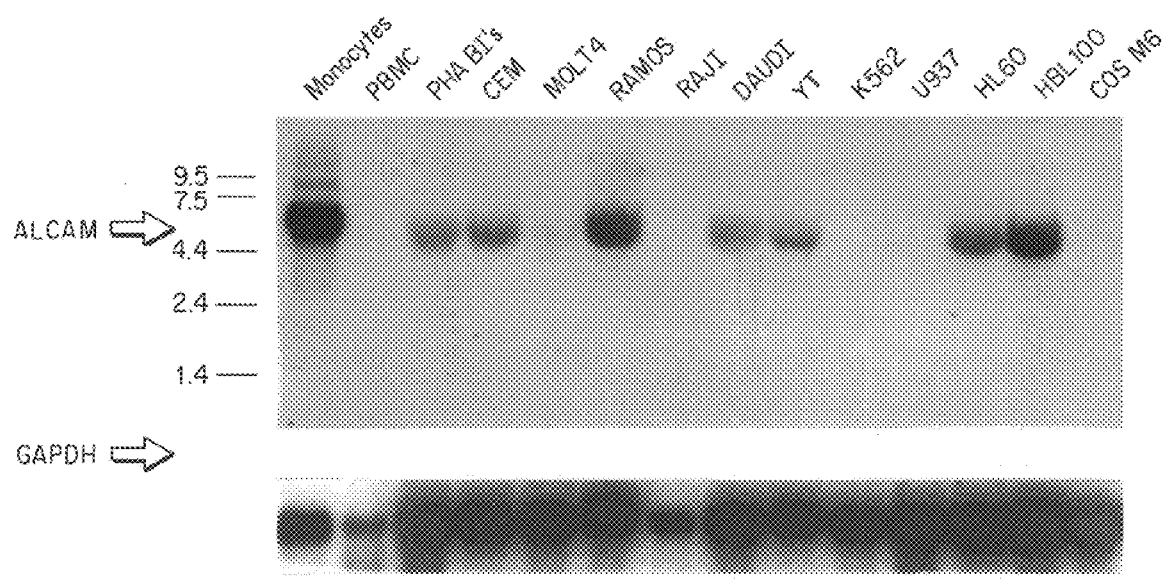

ALCAM is expressed by activated leukocytes. By Northern blot analysis an ALCAM cDNA probe hybridized with a ~5.2 kb mRNA expressed by mitogen activated peripheral blood mononuclear cells (PBMC) and a number of T cell, B cell, monocytic, and tumor derived cell lines; activated monocytes showed two additional minor species of ~10 and 8.5 kb (FIG. 26B). ALCAM mRNA was not detected in unactivated PBMC. To examine if the presence of ALCAM transcripts in activated T cells corresponded to the expression of a J4-81 and CD6-Rg binding protein, PBMC were activated with PHA and aliquots of the bulk culture were examined by flow cytometry for 10 days. Expression of a J4-81 and CD6 binding protein on T cells was observed two days after activation, was maximal at three days, and declined to undetectable levels eight days after activation (FIG. 26C). The binding of J4-81 and CD6-Rg to activated T cells exhibits the same expression kinetics, indicating that these two molecules recognize the same molecular target.

Figure 27:
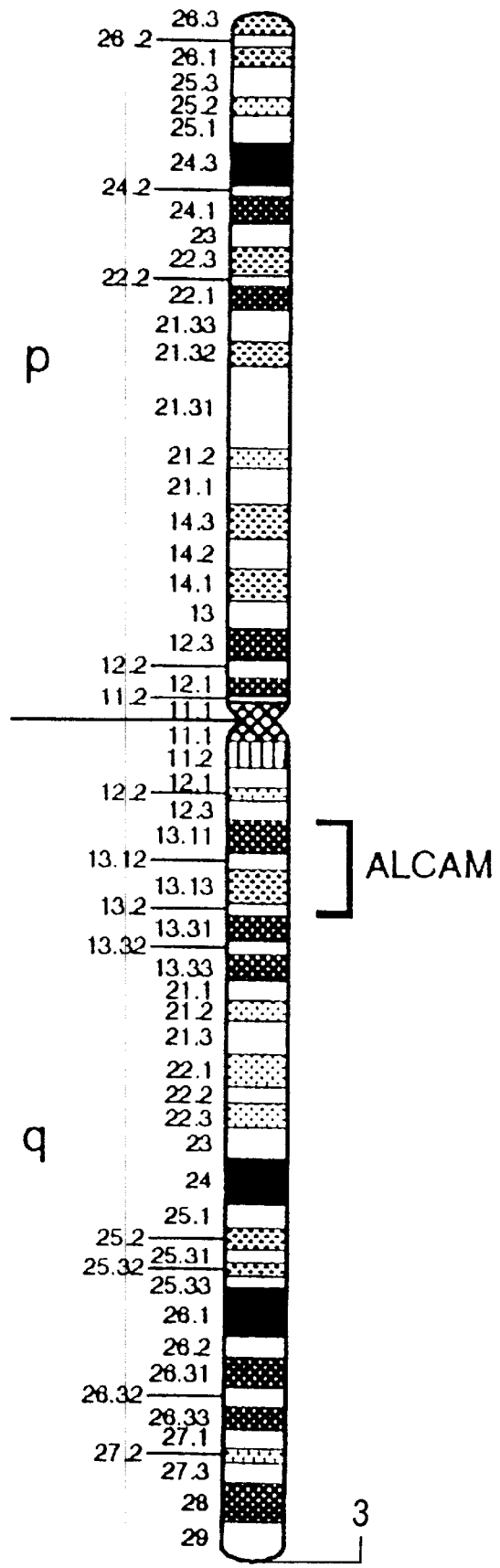
FIG. 27. Human chromosomal mapping. Fluorescence in situ hybridization (FISH) of cDNA probes to R-banded chromosomes generated signals on both chromatids (indicated by arrows) on chromosome 3 at bands q13.1–q13.2. The region is shown by brackets on a G-banding ideogram.

Assignment of human ALCAM gene to chromosome bands 3q13.1–q13.2. Fluorescence in situ hybridization experiments using ALCAM cDNA clones as probes localized the gene to a single site on the proximal long arm of human chromosome 3. Of 25 metaphase spreads analyzed, exhibited a specific fluorescent signal on both chromatids at this site, and 13 of 20 had signal on both chromosome 3 homologues. The chromosomes were identified by an R-banding pattern produced by the incorporation of BrdU after synchronization of the cell culture. The ALCAM signal was assigned to bands 3q13.1–q13.2 (FIG. 27).

ALCAM is a CD6 ligand. To directly examine if the ALCAM cDNA clone isolated from HL60 cells directs the expression of a protein which binds J4-81 and CD6-Rg, the cDNA was transfected into COS cells. Three days posttransfection, the COS cells were examined for their ability to bind to J4-81 (aALCAM) or CD6-Rg by flow cytometry. As shown in FIG. 28A, COS cells expressing ALCAM were able to bind to both J4-81 and CD6-Rg. To further confirm that ALCAM is a CD6 ligand, a chimeric gene encoding ALCAM-Rg was constructed. This protein was expressed as a covalent homodimer with a molecular mass of ~200 kDa and was recognized by mAb J4-81. To demonstrate the binding of ALCAM-Rg to CD6, COS cells were transfected with a cDNA clone encoding CD6 (Aruffo et al, J. Exp. Med. 174:949 (1991)) and examined by flow cytometry three days later. COS cells transfected with CD6 bound both G3-6 (aCD6) and ALCAM-Rg (FIG. 28B). These results demonstrate that CD6 and ALCAM are a receptor/ligand pair.

Chicken BEN has been reported to mediate homotypic adhesion (Pourquie et al, Proc. Natl. Acad. Sci. USA 89:5261 (1992)); Tanaka et al, Neuron 7:535 (1991)); Burns et al, Neuron 7:209 (1991)). ALCAM-Rg was able to bind COS cells that expressed ALCAM, indicating that ALCAM mediates both homophillic and heterophillic adhesion.

EXAMPLE V

Production of anti-human ALCAM monoclonal antibodies. A 6–8 week old female BALB/c mouse (Taconic, Germantown, N.Y.) was immunized with a purified, recombinant fusion protein consisting of the extracellular domain of human ALCAM fused to the hinge, CH2, and CH3 domains of murine IgG2a. Primary immunization was administered intraperitoneally as a 100 μl emulsion of 50 μg protein in Ribi adjuvant (R-730, Ribi ImmunoChem Research, Inc., Hamilton, Mont.). Two identical immunizations were performed on days 19 and 29. On day 63, 50 μg of protein in 100 μl of PBS was administered intravascularly. Three days later, cells were harvested from the spleen and all identifiable lymph nodes, and fused at a 3:1 ratio of leukocytes:myeloma cells with X63-Ag8.653 myeloma cells (Kearney et al, J. Immunol. 123:1548 (1979)) according to the method of Lane (J. Immunol. 81:223 (1985)). The cell suspension was seeded into 15 96-well culture plates at a density of $1.44 \times 10^5$ cells/well in the presence of hybridoma growth medium [Iscove's Modified Dulbecco's Medium (IMDM) supplemental with 10% fetal calf serum, 2 mM L-glutamine, 100 U/ml penicillin, 100 μg/ml streptomycin, 10% cloning factor (BM-Condimed H1; Boerhinger Mannheim, Indianapolis, Ind.), and HAT (100 μM hypoxanthine; 0.4 μM aminopterin; 16 μM thymidine)].

Screening of hybridoma supernatants. Hybridoma supernatants were screened on day 10 using an antigen capture based ELISA that employed a horseradish peroxidase (HRP) conjugated goat anti-mouse IgG second step reagent (Zymed Laboratories, South San Francisco, Calif.) for the detection of bound mAb. Briefly, 50 ng of fusion protein diluted in 50 mM sodium bicarbonate, pH 9.6, was adsorbed overnight at room temperature to wells of 96 well Immulon II microtiter plates (Dynatech Laboratories, Chantilly, V.A.). The wells were washed three times with PBS/0.5% Tween-20; unreactive sites were blocked with specimen diluent (Genetic Systems, Seattle, Wash.) for 1 h (this and all subsequent incubations were at room temperature). The plate was washed three times and hybridoma supernatants were added for 1 h and then washed three times. The HRP conjugated second reagent, diluted 1:1000 in specimen diluent, was added to the wells for 1 h and then washed three times. EIA chromagen diluted 1:100 in EIA substrate buffer (Genetic Systems, Seattle, Wash.) was added, allowed to develop for approximately 15 min., and stopped with 1 N $H_2SO_4$. The plates were read at OD450/630 on a BioTek microtiter plate reader (BioTek Instruments, Winooski, N.H.).

Those supernatants that reacted with ALCAM Rg but not a similarly constructed irrelevant Rg fusion protein were further evaluated for their ability to bind to the T cell lymphoma cell line, HPB-ALL, which expressed ALCAM. Approximately $5 \times 10^5$ cells were treated with 100 μl of supernatant for 1 h on ice, washed 3× with PBA (PBS/1% BSA/0.1% sodium azide) and then treated for 30 min. on ice with a 1:50 dilution of goat anti-murine IgG-FITC (BioSource International, Camarillo, Calif.) in PBA. The cells were then washed 2× with PBA, 1× with PBS, fixed with PBS/2% formaldehyde, and analyzed by flow cytometry with a FACScan (Becton Dickinson, Mountain View, Calif.).

Those hybridomas that produced mAb that recognized the HPB-ALL cells were then cloned by limiting dilution in a 96 well microtiter plate in hybridoma growth medium lacking HAT. The supernatants were similarly evaluated by ELISA and FACS analysis as described above.

Characterization of anti-ALCAM hybridomas/monoclonal antibodies. Hybridoma clones were expanded and the supernatants were subjected to Protein G Sepharose affinity chromatography to obtain purified antibody. Antibody was eluted with 0.1 M sodium citrate, pH 3.0, neutralized with 1/10 volume IM Tris, pH 9.0, and dialyzed against PBS. Antibodies were concentrated with a Centricon 30 concentrator (Amicon, Beverly, Mass.) and quantitated by OD280 absorbance to determine antibody concentration.

EXAMPLE VI

Determination of antibody domain specificity. ALCAM is encoded by 5 extracellular Ig like domains: 2 amino-terminal V set domains followed by 3 C2 set domains. To determine the domain specificity of the monoclonal antibodies, a series of ALCAM Rg fusion proteins that were truncated starting with the carboxy-terminal domains were constructed (described below). The fusion proteins were expressed in COS cells and purified by Protein A Sepharose affinity chromatography. The ALCAM fusion proteins (ALCAM-, ALC WCC-, ALC VVC-, ALC VV-, ALC V-) and the irrelevant fusion protein CD6 Rg were adsorbed to Immulon I (Dynatech Laboratories, Chantilly, V.A.) 96 well microtiter plates at 60 ng/well as described above. The plates were processed as above for the screening ELISA, but purified antibody diluted in specimen diluent was added at 50 ng/well. Human IgG adsorbed, HRP conjugated donkey anti-murine IgG (Jackson Immunoresearch, Malvern, Pa.) diluted 1:2000 in specimen diluent was used to detect antibody binding to the fusion proteins.

The results of this experiment are summarized in Table 6. Also included in this assay was the above described anti-ALCAM mAb, J4-81. From this type of analysis, a prediction as to the domain specificity of the monoclonal antibodies can be made. HAL 151.2.1 recognized V1, while J4-81 appears to recognize V2 of ALCAM, as do HAL 31.1, 33.1, 62.1, 81, and 143. HAL 192 recognizes Cl, HAL 20.1, 47.1, and 145 recognize C2 and HAL 8.2 recognizes C3.

TABLE 6

Characterization of Domain Specificity of anti-ALCAM mAb

| mAb | CD6 | ALCAM | ALC VVCC | ALC VVC | ALC VV | ALC V | Domain Specificity* |
|---|---|---|---|---|---|---|---|
| HAL 8.2 | − | + | +[]m- | +[]m- | +[]m- | +[]m- | C3? |
| HAL 20.1 | − | + | + | +[]m- | − | − | C2 |
| HAL 31.1 | − | + | + | + | + | − | V2 |
| HAL 33.1 | − | + | + | + | + | − | V2 |
| HAL 47.1 | − | + | + | +[]m- | − | − | C2 |
| HAL 62.1 | − | + | + | + | + | − | V2 |
| HAL 81 | − | + | + | + | + | +[]m- | V1-2 |
| HAL 114.3 | − | + | + | + | − | − | C1 |
| HAL 143 | − | + | + | + | + | − | V2 |
| HAL 145 | − | + | + | − | − | − | C2 |
| HAL 151.2.1 | − | + | + | + | + | + | V1 |
| HAL 192 | − | + | + | + | − | − | C1 |
| J4-81 | − | + | + | + | + | − | V2 |
| J3-119 | − | + | + | + | + | − | V2 |

*Presumed domain specificity was determined by an ELISA that measured the binding of anti-ALCAM to immobilized ALCAM fusion proteins.

The monoclonal antibodies were then isotyped by a similar assay as already described. ALCAM Rg was adsorbed to Immulon I plates and treated with the monoclonal antibodies as above. Antibody binding was determined with the mIgG isotype specific HRP conjugated secondary reagents (Pharmingen, San Diego, Calif.) at the following dilutions: IgG1:15,000, IgG2a 1:100, IgG2b 1:2,000, and IgG3 1:250. The substrate was allowed to develop for 45 min. before stopping with $H_2SO_4$. Readings at OD450/630 were taken. HAL 8.2, 31.1, 33.3, 62.1, 81, 114.3, 145, and J4-81 are IgG1, HAL 20.1 and 151.2.1 are IgG2a, and HAL 47.1, and 143, are IgG2b.

Hybridomas producing the following monoclonal antibodies were deposited at the American Type Culture Collection, Rockville, Md. on Jun. 18, 1996 and assigned the indicated accession numbers:

| Antibody | Accession No. |
|---|---|
| HAL 8.2 | HB 12139 |
| HAL 47.1 | HB 12137 |
| HAL 62.1 | HB 12138 |
| HAL 143 | HB 12141 |
| HAL 114.3 | HB 12136 |
| HAL 151.2.1 | HB 12140. |

EXAMPLE VII

Construction of ALCAM domain truncation fusion proteins. The construction of the ALCAM Rg fusion protein is decribed above. Complementary DNA fragments encoding single or multiple domains of ALCAM (FIG. 30) were obtained by PCR (polymerase chain reaction). The sets of primers used for the individual fragments were as follows: (1) FP3/VVCC-R, (2) FP3/VVC-R, (3) FP3/VV-R, (4) FP3/V-R. The sequences of the primers are: FP3 gtacgggcca-gatatacgcgttgacattgatta (SEQ ID NO:10), VVCC-R agtgtc-tataggatccttgccttctacaatgagagt (SEQ ID NO:11), VVC-R agtgtctataggatccaaatccaaatagtgaactgt (SEQ ID NO:12), VV-R agtgtctataggatcctctgtaggatagtaaatatc (SEQ ID NO:13), V-R agtgtctataggatccagtgctttgcttacaatttcagg (SEQ ID NO:14). The template used for the synthesis was ALCAM cDNA in pCDM8. The reactions were carried out by standard PCR protocols using Taq polymerase (Boerhinger Mannheim, Indianapolis, Ind.) according to the manufacturer's instructions. The cycles were as follows: 1×94° C./3 min., 55° C./2 min., 72° C./3 min.; 30×94° C./1.5 min., 55° C./2 min., 72° C./2.5 min., and 1×72° C./3 min. The PCR products were digested with MLU1 and BAMH1 restriction enzymes and cloned into a vector containing the hinge, CH2 and CH3 domains of human IgG1 that had been similarly digested with the same enzymes. COS cells were transfected with the vectors and the fusion proteins were purified by adsorption to and elution from Proteins A Sepharose as described above for antibody purification.

All documents cited above are hereby incorporated in their entirety by reference.

One skilled in the art will appreciate from a reading of this disclosure that various changes in form and detail can be made without departing from the true scope of the invention.

What is claimed is:

1. A hybridoma having ATCC accession number HB 12136, HB 12137, HB 12138, HB12139, HB 12140, or HB 12141.

2. A monoclonal antibody produced by a hybridoma having ATCC accession number HB 12136, HB 12137, HB 12138, HB 12139, HB 12140 or HB 12141, or an antigen binding fragment of said monoclonal antibody produced by said hybridoma having ATCC accession number HB 12136, HB 12137, HB 12138, HB 12139, HB 12140 or HB 12141.

3. A monoclonal antibody produced by a hybridoma having ATCC accession number HB 12136, HB 12137, HB 12138, HB 12139, HB 12140 or HB 12141.

* * * * *